US010626414B2

(12) United States Patent
Gallei et al.

(10) Patent No.: US 10,626,414 B2

(45) Date of Patent: Apr. 21, 2020

(54) SWINE INFLUENZA VACCINE

(71) Applicant: Boehringer Ingelheim Vetmedica GmbH, Ingelheim am Rhein (DE)

(72) Inventors: Andreas Gallei, Wedemark (DE); Alice Mundt, Isernhagen (DE); Veljko Nikolin, Hannover (DE)

( * ) Notice: Subject to any disclaimer, the term of this patent is extended or adjusted under 35 U.S.C. 154(b) by 0 days.

(21) Appl. No.: 15/706,896

(22) Filed: Sep. 18, 2017

(65) Prior Publication Data

US 2018/0080044 A1 Mar. 22, 2018

(30) Foreign Application Priority Data

Sep. 20, 2016 (EP) .................................... 16189767

(51) Int. Cl.

| | |
|---|---|
| ***C12N 15/86*** | (2006.01) |
| ***A61K 39/145*** | (2006.01) |
| ***A61K 39/12*** | (2006.01) |
| *A61K 39/00* | (2006.01) |

(52) U.S. Cl.

CPC .............. *C12N 15/86* (2013.01); *A61K 39/12* (2013.01); *A61K 39/145* (2013.01); *A61K 2039/5256* (2013.01); *A61K 2039/54* (2013.01); *A61K 2039/541* (2013.01); *A61K 2039/544* (2013.01); *A61K 2039/545* (2013.01); *A61K 2039/552* (2013.01); *A61K 2039/60* (2013.01); *A61K 2039/70* (2013.01); *C12N 2710/16043* (2013.01); *C12N 2710/16743* (2013.01); *C12N 2760/16122* (2013.01); *C12N 2760/16134* (2013.01); *C12N 2760/16171* (2013.01)

(58) Field of Classification Search

None

See application file for complete search history.

(56) References Cited

U.S. PATENT DOCUMENTS

| | | | | |
|---|---|---|---|---|
| 3,857,423 | A | 12/1974 | Ronca, Jr. | |
| 5,616,326 | A | 4/1997 | Spibey | |
| 5,820,868 | A | 10/1998 | Mittal et al. | |
| 5,851,521 | A | 12/1998 | Branellec et al. | |
| 6,090,393 | A | 7/2000 | Fischer | |
| 6,110,735 | A | 8/2000 | Chartier et al. | |
| 6,127,175 | A | 10/2000 | Vigne et al. | |
| 6,156,567 | A | 12/2000 | Fischer | |
| 6,193,983 | B1 * | 2/2001 | Crabb | A61K 39/245 424/184.1 |
| 6,225,111 | B1 * | 5/2001 | Cochran | A61K 39/245 435/320.1 |
| 6,261,807 | B1 | 7/2001 | Crouzet et al. | |
| 6,294,377 | B1 | 9/2001 | Haddada et al. | |
| 6,420,170 | B1 | 7/2002 | Perricaudet et al. | |
| 6,669,942 | B2 | 12/2003 | Perricaudet et al. | |
| 7,037,723 | B1 | 5/2006 | Heilbronn | |
| 7,744,900 | B2 | 6/2010 | Dubensky, Jr. et al. | |
| 8,119,396 | B2 | 2/2012 | Eloit et al. | |
| 2001/0014319 | A1 | 8/2001 | Denefle et al. | |
| 2002/0006395 | A1 | 1/2002 | Perricaudet et al. | |
| 2002/0090716 | A1 * | 7/2002 | Markham | C12N 15/86 435/235.1 |
| 2003/0096787 | A1 | 5/2003 | Perricaudet et al. | |
| 2003/0100116 | A1 | 5/2003 | Kremer et al. | |
| 2004/0109873 | A1 | 6/2004 | Neubauer et al. | |
| 2011/0091490 | A1 | 4/2011 | Okazaki et al. | |
| 2011/0110892 | A1 | 5/2011 | Desrosiers | |
| 2011/0236419 | A1 | 9/2011 | Audonnet et al. | |
| 2018/0080043 | A1 | 3/2018 | Mundt et al. | |
| 2018/0080044 | A1 * | 3/2018 | Gallei | A61K 39/12 |
| 2018/0080045 | A1 | 3/2018 | Gallei et al. | |
| 2018/0080047 | A1 | 3/2018 | Mundt et al. | |

FOREIGN PATENT DOCUMENTS

| | | |
|---|---|---|
| EP | 0512017 B1 | 6/1997 |
| EP | 1118670 A1 | 7/2001 |
| EP | 0736100 B1 | 3/2002 |
| EP | 0979101 B1 | 10/2010 |

(Continued)

OTHER PUBLICATIONS

Combadiere et al. (Pathologie Biologie. 2010; 58: e79-e86).*

Said et al. (Veterinary Microbiology. 2011; 154; 113-123).*

Thormann et al. (Virus Research. 2012; 169: 203-211).*

Sequence alignment of instant SEQ ID 26 with Geneseq database access No. AZG98675; 2011.*

Sequence alignment of instant SEQ ID No. 1 with 2004 Geneseq database access No. ADP74214 by Neubauer et al in USPgPub 2004109873.*

Sequence alignment of instant SEQ ID No. 2 with 2004 Geneseq database access No. ADP74214 by Neubauer et al in USPgPub 2004109873.*

Sequence alignment of SEQ ID 14 with 2004 Geneseq database access No. ADP74211 by Neubauer et al in USPgPub 2004109873.*

(Continued)

*Primary Examiner* — Shanon A. Foley

(74) *Attorney, Agent, or Firm* — Judy Jarecki-Black

(57) ABSTRACT

The present invention relates to Equine Herpes Virus (EHV) vectors comprising at least one exogenous antigen encoding sequence relating to a pathogen infecting food producing animals, wherein said exogenous antigen encoding sequence is inserted into an insertion site, preferably ORF70, and said exogenous antigen encoding sequence is operably linked to a promoter sequence, preferably the promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof. Furthermore, the present invention relates to methods for immunizing a food producing animal comprising administering to such food producing animal an immunogenic composition comprising embodiments of the present invention. Moreover, the present invention relates to methods for the treatment or prophylaxis of clinical signs caused by swine influenza virus in a food producing animal.

30 Claims, 28 Drawing Sheets

Specification includes a Sequence Listing.

(56) References Cited

FOREIGN PATENT DOCUMENTS

| | | | |
|---|---|---|---|
| WO | 199111525 | A2 | 8/1991 |
| WO | 199522607 | A1 | 8/1995 |
| WO | 199800166 | A1 | 1/1998 |
| WO | 200008165 | A1 | 2/2000 |
| WO | 0142481 | A2 | 6/2001 |
| WO | 2007081336 | A1 | 7/2007 |
| WO | 2007115059 | A2 | 10/2007 |
| WO | 2018054822 | A1 | 3/2018 |
| WO | 2018054837 | A1 | 3/2018 |
| WO | 2018054840 | A1 | 3/2018 |
| WO | 2018057441 | A1 | 3/2018 |

OTHER PUBLICATIONS

Sequence alignment of instant SEQ ID No. 3 with 2004 Geneseq database access No. ADP74214 by Neubauer et al in USPgPub 200410987.*
Sequence alignment of instant SEQ ID No. 4 with 2004 Geneseq database access No. ADP74214 by Neubauer et al in USPgPub 200410987.*
Von Einem et al. (Virology. 2007; 362: 151-162).*
Hussey et al. (Veterinary Research. 2011; 42: 23).*
Ma et al. (PLoSONE. 2012; 7 (4): e34425).*
Badr et al. (Archives of Virology. 2018; 163: 599-607).*
Telford et al., "The DNA sequence of equine herpesvirus-4." Journal of General Virology, vol. 79, 1998, pp. 1197-1203.
Trapp et al. "Potential of Equine Herpesvirus 1 as a Vector for Immunization." Journal of Virology, vol. 79, No. 9, May 2005, pp. 5445-5454.
Van De Walle et al., "Analysis of the Herpesvirus Chemokine-binding Glycoprotein G Residues Essential for Chemokine Binding and Biological Activity." The Journal of Biological Chemistry, vol. 384, No. 9, Feb. 27, 2009, pp. 5968-5976.
Van Olphen et al., "Generation of infectious genome of bovine adenovirus type 3 by homologous recombination in bacteria." Journal of Virological Methods, vol. 77, 1999, pp. 125-129.
Von Einem et al. "In vitro and in vivo characterization of equine herpesvirus type 1 (EHV-1) mutants devoid of the viral chemokine-binding glycoprotein G (gG)." Virology, vol. 362, 2007, pp. 151-162.
Xue et al., "Vaccination with a modified-live bovine viral diarrhea virus (BVDV) type 1a vaccine completely protected calves against challenge with BVDV type 1b strains." Vaccine, vol. 29, 2011, pp. 70-76.
Yang et al., "Complete protection of cats against feline panleukopenia virus challenge by a recombinant canine adenovirus type 2 expressing VP2 from FPV." Vaccine, vol. 26, 2008, pp. 1482-1487.
Zhang et al., "Oral vaccination of dogs (*Canis familiaris*) with baits containing the recombinant rabies-canine adenovirus type-2 vaccine confers long-lasting immunity against rabies." Vaccine, vol. 26, 2008, pp. 345-350.
Babiuk et al, "Adenoviruses as vectors for delivering vaccines to mucosal surfaces." Journal of Biotechnology, vol. 83, 2000, pp. 105-113.
Bangari et al. "Development of nonhuman adenoviruses as vaccine vectors." Vaccine, vol. 24, No. 7, Feb. 2006, pp. 849-862.
Bouet-Cararo et al., "Canine adenoviruses elicit both humoral and cell-mediated immune responses against rabies following immunisation of sheep." Vaccine, vol. 29, 2011, pp. 1304-1310.
Bru et al., "An Update on Canine Adenovirus Type 2 and Its Vectors." Viruses, vol. 2, 2010, pp. 2134-2153.
Brun et al., "Antigen delivery systems for veterinary vaccine development Viral-vector based delivery systems." Vaccine, vol. 26, 2008, pp. 6508-6528.
Chapman et al., "Effect of intron a human cytomegalovirus (Towne) immediate-early gene on heterologous expression in mammalian cells." Nucleic Acids Research, vol. 19, No. 14, 1991, pp. 3979-3986.
Chartier et al. "Efficient Generation of Recombinant Adenovirus Vectors by Homologous Recombination in *Escherichia coli*." Journal of Virology, vol. 70, No. 7, Jul. 1996, pp. 4805-4810.
Chengalvala et al, "Adenovirus vectors for gene expression." Current Opinion in Biotechnology, vol. 2, No. 5, Oct. 1991, pp. 718-722.
Dai et al., "Cellular and humoral immune responses to adenoviral vectors containing factor IX gene: Tolerization of factor IX and vector antigens allows for long-term expression." Proceedings of the National Academy of Sciences, vol. 92, Feb. 1995, pp. 1401-1405.
De Turiso et al., "Recombinant Vaccine for Canine Parvovirus in Dogs." Journal of Virology, vol. 66, No. 5, May 1992, pp. 2748-2753.
Dong et al., "Systematic Analysis of Repeated Gene Delivery into Animal Lungs with a Recombinant Adenovirus Vector." Human Gene Therapy, vol. 7, No. 3, Feb. 10, 1996, pp. 319-331.
Fallaux et al., "New Helper Cells and Matched Early Region 1-Deleted Adenovirus Vectors Prevent Generation of Replication-Competent Adenoviruses." Human Gene Therapy, vol. 9, Sep. 1, 1998, pp. 1909-1917.
Fischer et al., "Vaccination of puppies born to immune dams with a canine adenovirus-based vaccine protects against a canine distemper virus challenge." Vaccine, vol. 20, 2002, pp. 3485-3497.
Ghosh-Choudhury et al., "Human adenovirus cloning vectors based on infectious bacterial plasmids." Gene, vol. 50, Nos. 1-3, 1986, pp. 161-171.
Haj-Ahmad et al., "Development of a helper-independent human adenovirus vector and its use in the transfer of the herpes simplex virus thymidine kinase gene." Journal of Virology, vol. 57, No. 1, Jan. 1986, pp. 267-274.
Henderson et al., "Oral immunization of raccoons and skunks with a canine adenovirus recombinant rabies vaccine." Vaccine, vol. 27, 2009, pp. 7194-7197.
Hsu et al., "Efficacy of adenovirus-vectored respiratory syncytial virus vaccines in a new ferret model." Vaccine, vol. 12, No. 7, 1994, pp. 607-612.
Hu et al., "Experimental immunization of cats with a recombinant rabies-canine adenovirus vaccine elicits a long-lasting neutralizing antibody response against rabies." Vaccine, vol. 25, 2007, pp. 5301-5307.
Hu et al., "Prevention of rabies virus infection in dogs by a recombinant canine adenovirus type-2 encoding the rabies virus glycoprotein." Microbes and Infection, vol. 8, 2006, pp. 1090-1097.
Huang et al., "Glycoprotein G deletion mutants of equine herpesvirus 1 (EHV1; equine abortion virus) and EHV4 (equine rhinopneumonitis virus)." Archives of Virology, vol. 150, 2005, pp. 2583-2592.
Imler, Jean-Luc, "Adenovirus vectors as recombinant viral vaccines." Vaccine, vol. 13, No. 13, 1995, pp. 1143-1151.
International Search Report and Written Opinion for PCT/EP2017/073438 dated Feb. 27, 2018.
International Search Report and Written Opinion for PCT/EP2017/073473 dated Jan. 31, 2018.
International Search Report and Written Opinion for PCT/EP2017/073481 dated Dec. 7, 2017.
International Search Report and Written Opinion for PCT/US2017/051964 dated Nov. 20, 2017.
Kapoor et al., "A nonessential glycoprotein is coded by early region E3 of adenovirus type 7." Virology, vol. 112, No. 2, Jul. 30, 1981, pp. 780-784.
Kelly et al., "Use of Nondefective Adenovirus-Simian Virus 40 Hybrids for Mapping the Simian Virus 40 Genome." Journal of Virology, vol. 12, No. 3, Sep. 1973, pp. 643-652.
Kremer et al., "Canine Adenovirus Vectors: an Alternative for Adenovirus-Mediated Gene Transfer." Journal of Virology, vol. 74, No. 1, 2000, pp. 505-512.
Levrero et al., "Defective and nondefective adenovirus vectors for expressing foreign genes in vitro and in vivo." Gene, vol. 101, No. 2, May 30, 1991, pp. 195-202.

(56) References Cited

OTHER PUBLICATIONS

Li et al., "A single immunization with a recombinant canine adenovirus expressing the rabies virus G protein confers protective immunity against rabies in mice." Virology, vol. 356, 2006, pp. 147-154.
Linné Tommy, "Differences in the E3 regions of the canine adenovirus type 1 and type 2." Virus Research, vol. 23, Nos. 1-2, Apr. 1992, pp. 119-113.
Liu et al., "Efficacy and safety of a live canine adenovirus-vectored rabies virus vaccine in swine." Vaccine, vol. 26, 2008, pp. 5368-5372.
Lubeck et al., "Immunogenicity and efficacy testing in chimpanzees of an oral hepatitis B vaccine based on live recombinant adenovirus." Proceedings of the National Academy of Sciences USA, vol. 86, No. 17, Sep. 1989, pp. 6763-6767.
Ma et al., "An Equine Herpesvirus Type 1 (EHV-1) Expressing VP2 and VP5 of Serotype 8 Bluetongue Virus (BTV-8) Induces Protection in a Murine Infection Model." PLoS ONE, vol. 7, No. 4, Apr. 2012, e34425, pp. 1-9.
Massie et al., "New adenovirus vectors for protein production and gene transfer." Cytotechnology, vol. 28, 1998, pp. 53-64.
Miittal et al., "Pathology and immunogenicity in the cotton rat (*Sigmodon hispidus*) model after infection with a bovine adenovirus type 3 recombinant virus expressing the firefly luciferase gene." Journal of General Virology, vol. 77, 1996, pp. 1-9.
Morin et al., "Recombinant adenovirus induces antibody response to hepatitis B virus surface antigen in hamsters." Proceedings of the National Academy of Sciences, USA, vol. 84, Jul. 1987, pp. 4626-4630.
Morrison et al., "Generation of E3-Deleted Canine Adenoviruses Expressing Canine Parvovirus Capsid by Homologous Recombination in Bacteria." Virology, vol. 293, 2002, pp. 26-30.
Nagesha et al., "Analysis of the nucleotide sequence of five genese at the left end of the unique short region of the equine herpesvirus 4 genome." Archives of Virology, vol. 128, 1993, pp. 143-154.
Natuk et al., "Immunogenicity of Recombinant Human Adenovirus—Human Immunodeficiency Virus Vaccines in Chimpanzees." AIDS Research and Human Retroviruses, vol. 9, No. 5, May 1993, pp. 395-404.
Prevec et al., "Use of Human Adenovirus-based Vectors for Antigen Expression in Animals." Journal of General Virology, vol. 70, 1989, pp. 429-434.
Reddy et al., "Development of porcine adenovirus-3 as an expression vector." Journal of General Virology, vol. 80, 1999, pp. 563-570.
Said et al., "An equine herpesvirus 1 (EHV-1) vectored H1 vaccine protects against challenge with swine-origin Influenza virus H1N1." Veterinary Microbiology, vol. 154, 2011, pp. 113-123.
Said et al., "Recombinant equine herpesvirus 1 (EHV-1) vaccine protects pigs against challenge with influenza A (H1N1)pmd09". Virus Research, vol. 173, 2013, pp. 371-376.
Said, Abdelrahman, "Development of a vectored equine herpesvirus type 1 (EHV-1) vaccine against pandemic Influenza A virus (09/H1N1)." Inaugural-Dissertation, Berlin, 2013, Journal-Nr: 3637, pp. 1-83. [Accessed at: http://www.diss.fu-berlin.de/diss/servlets/MCRFileNodeServlet/FUDISS_derivate_000000013293/Said_online.pdf retrieved on Mar. 8, 2017].
Saito et al., "Construction of nondefective adenovirus type 5 bearing a 2.8-kilobase hepatitis B virus DNA near the right end of its genome." Journal of Virology, vol. 54, No. 3, Jun. 1985, pp. 711-719.
Shibata et al., "Nucleotide Sequence of E1 Region of Canine Adenovirus Type 2." Virology, vol. 172, 1989, pp. 460-467.
Spibey et al., "Identification and nucleotide sequence of the early region 1 from canine adenovirus types 1 and 2." Virus Research, vol. 14, No. 3, Nov. 1989, pp. 241-255.
Spibey et al., "Molecular Cloning and Restriction Endonuclease Mapping of Two Strains of Canine Adenovirus Type 2." Journal of General Virology, vol. 70, 1989, pp. 165-172.
Tartaglia et al., "Protection of Cats against Feline Leukemia Virus by Vaccination with a Canarypox Virus Recombinant, ALVAC-FL." Journal of Virology, vol. 67, N. 4, Apr. 1993, pp. 2370-2375.

* cited by examiner

FIG. 2

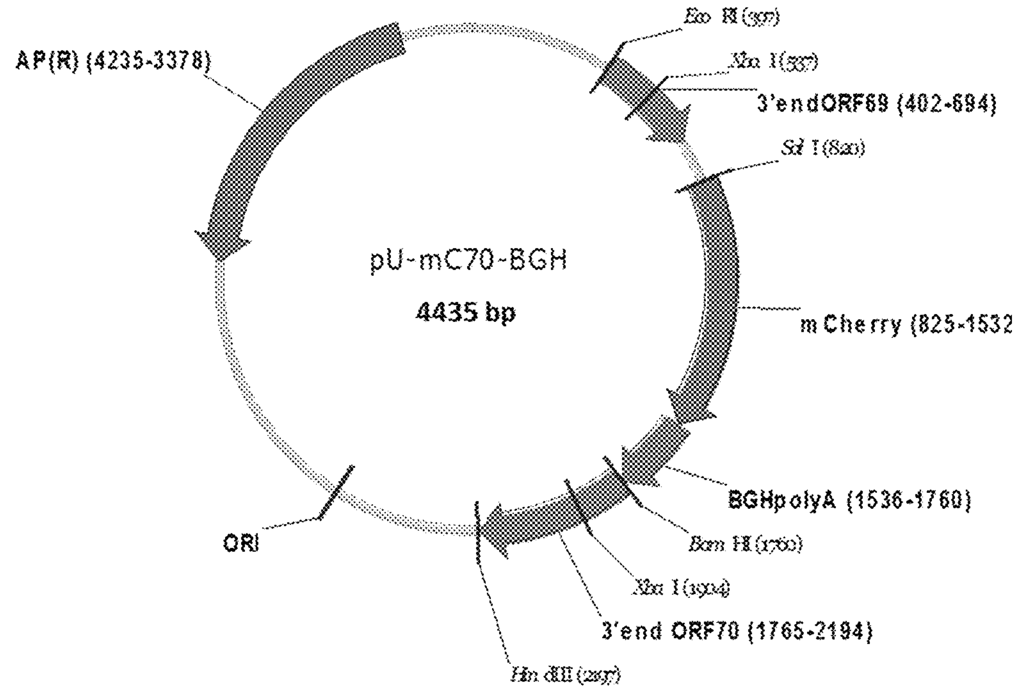

3'end ORF69 viral genomic DNA sequence flanking the insertion site upstream
3'end ORF70 viral genomic DNA sequence flanking the insertion site downstream
BGHpolyA polyadenylation sequence
ORI origin of replication of plasmid vector
Apr Ampicillin-resistance gene Betalactamase
BamHI, EcoRI, HindIII, SalI, XbaI indicate restriction endonuclease cleavage sites FIG. 3
A
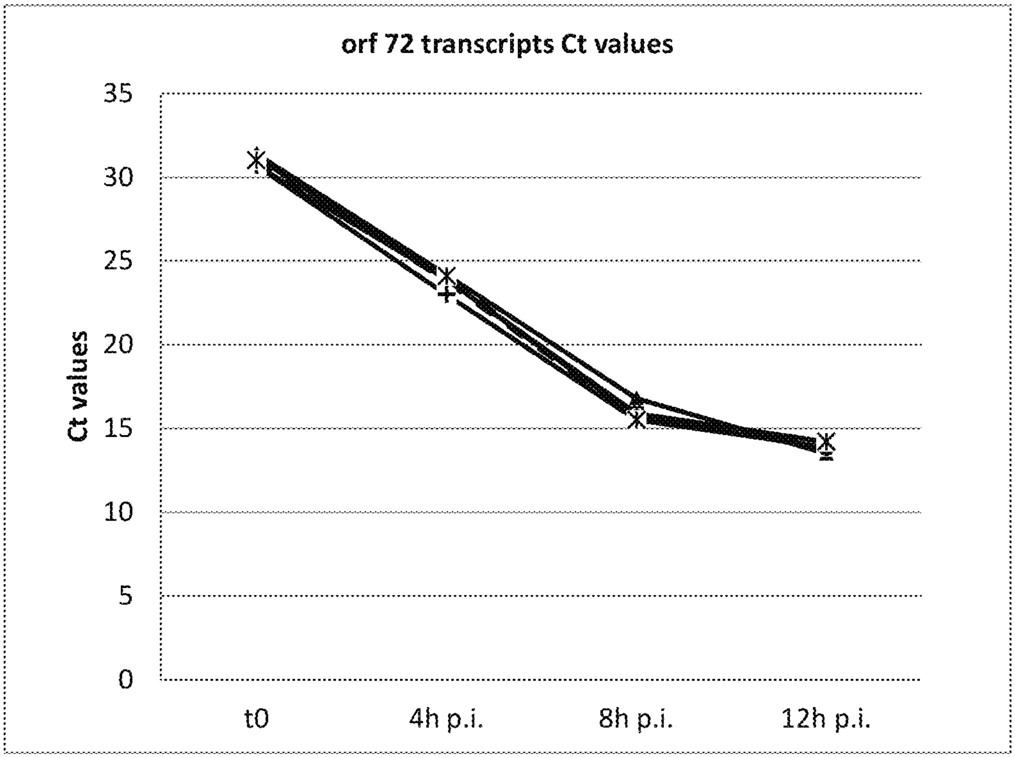
B
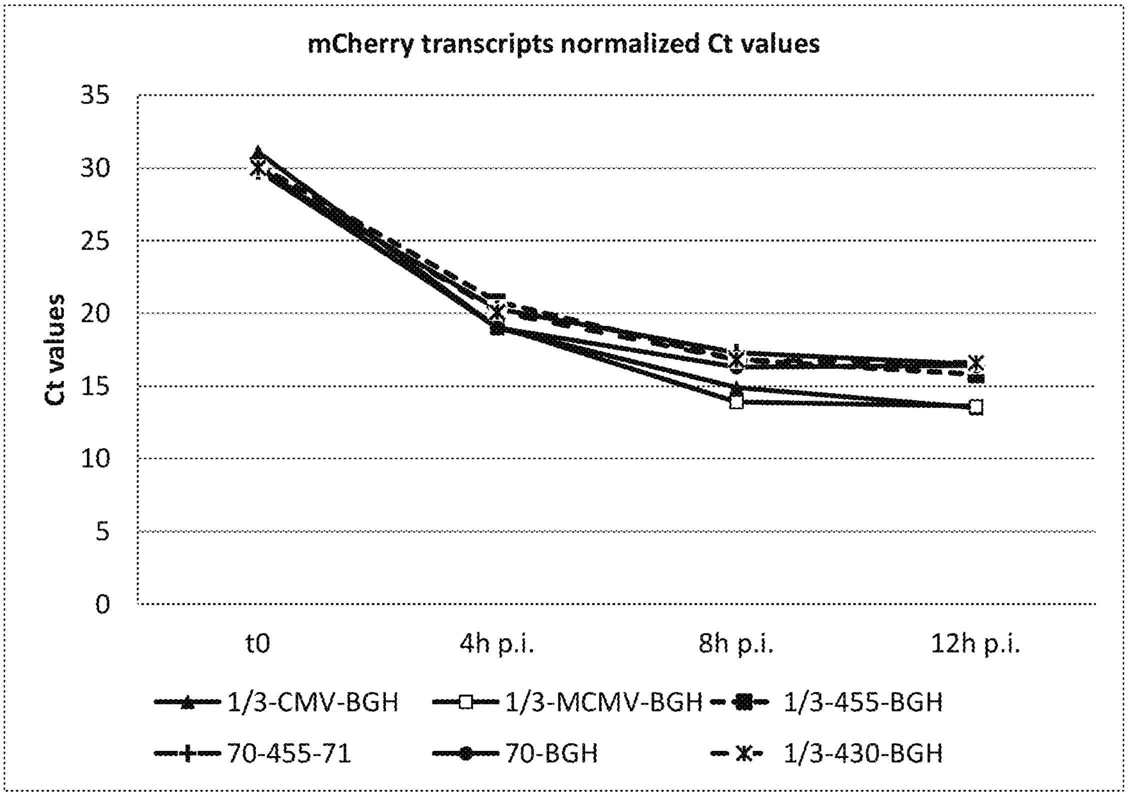

| | 1/3-CMV-BGH (V) | 1/3-MCMV-BGH (V) | 1/3-455-BGH (V) | 70-455-71 (V) | 70-egGp-BGH (V) | 1/3-430-BGH (V) | | 1/3-CMV-BGH (P) | 1/3-MCMV-BGH (P) | 1/3-455-BGH (P) | 70-455-71 (P) | 70-egGp-BGH (P) | 1/3-430-BGH (P) |
|---|---|---|---|---|---|---|---|---|---|---|---|---|---|
| 4 h p.i. | 5.46 | 5.17 | 4.95 | 5.19 | 5.43 | 5.96 | | 11.2 | 11.1 | 9.4 | 9.9 | 11.2 | 10.1 |
| 8 h p.i. | 7.77 | 10.42 | 8.06 | 9.05 | 9.06 | 9.9 | | 15.3 | 16.3 | 13.4 | 12.9 | 13.9 | 13.4 |
| 12 h p.i. | 8.04 | 10.67 | 8.39 | 9.93 | 9.48 | 9.1 | | 16.7 | 16.6 | 14.4 | 13.7 | 13.8 | 13.6 |

FIG. 5

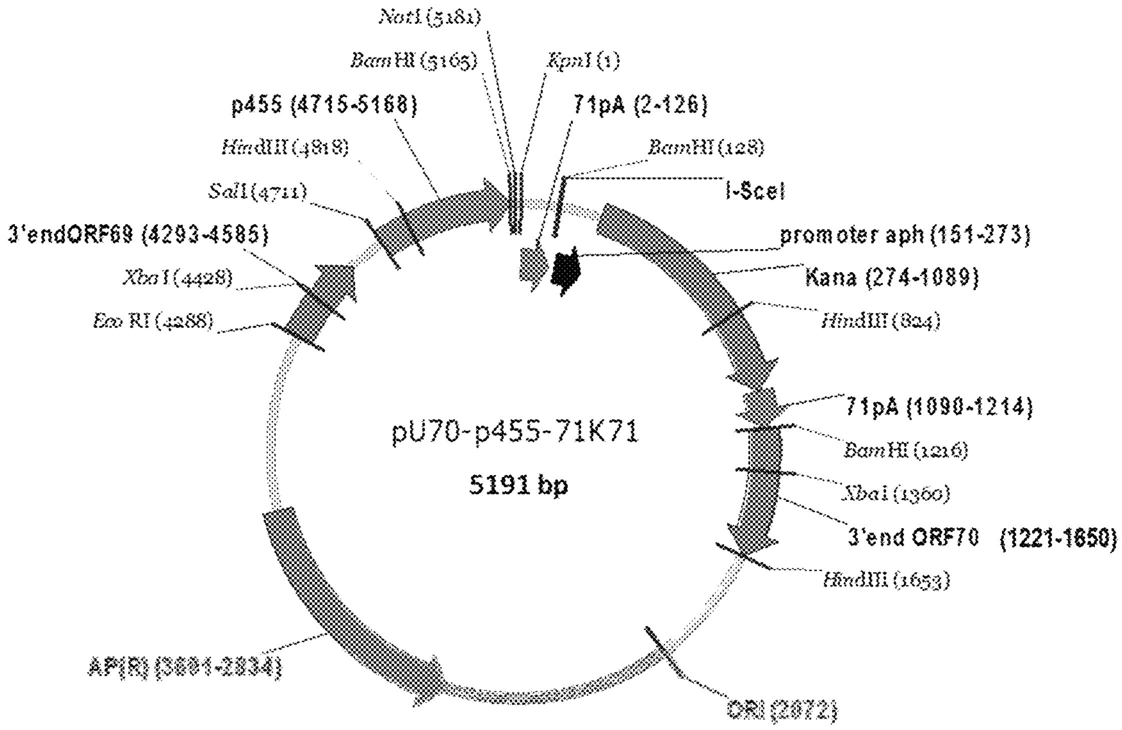

3'end ORF69 viral genomic DNA sequence flanking the insertion site upstream
3'end ORF70 viral genomic DNA sequence flanking the insertion site downstream
p455 promoter driving expression of transgene
71pA polyadenylation sequence
I-Sce1 cleavage site for I-Sce1
promoter aph prokaryotic promoter driving expression of Kanamycin-resistence gene
Kana Kanamycine resistance orf
ORI origin of replication of plasmid vector
Apr Ampicillin-resistance gene
EcoRI, SalI, NotI, HindIII, KpnI, BamHI, XbaI indicate restriction endonuclease cleavage sites

FIG. 6

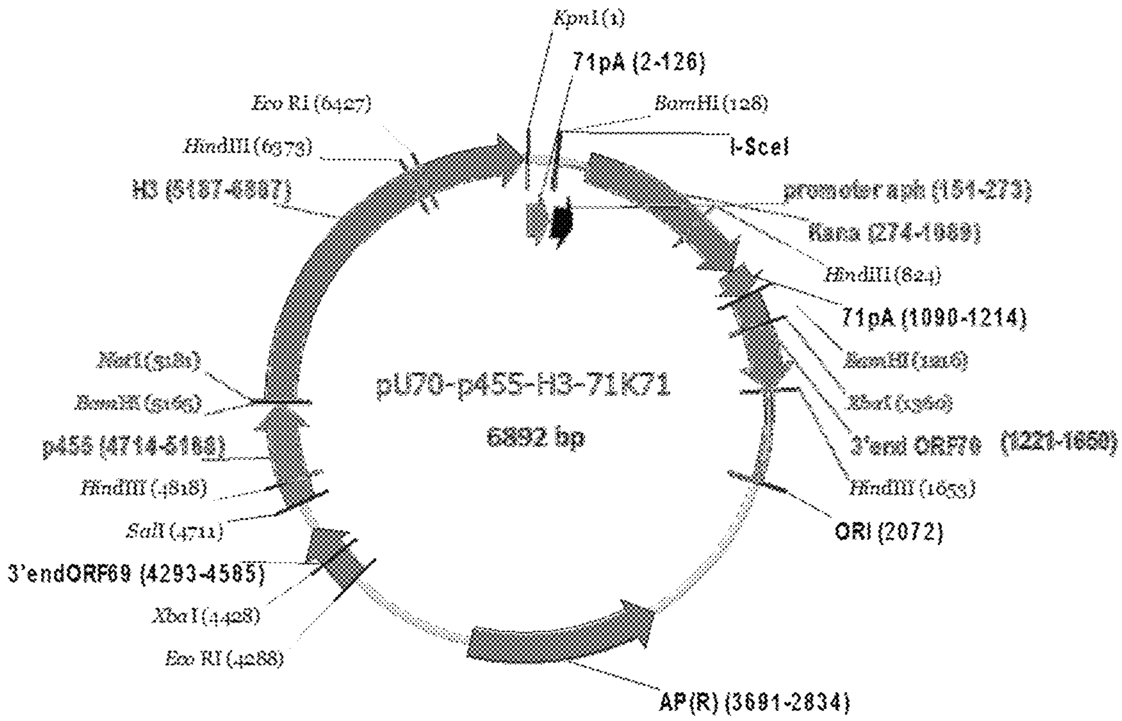

3'end ORF69 viral genomic DNA sequence flanking the insertion site upstream
3'end ORF70 viral genomic DNA sequence flanking the insertion site downstream
p455 promoter driving expression of transgene
H3 transgene (IAV hemagglutinin)
71pA polyadenylation sequence
I-Sce1 cleavage site for I-Sce1
promoter aph prokaryotic promoter driving expression of Kanamycin-resistence gene
Kana Kanamycine resistance orf
ORI origin of replication of plasmid vector
Apr Ampicillin-resistance gene
EcoRI, SalI, NotI, HindIII, KpnI, BamHI, XbaI indicate restriction endonuclease cleavage sites rEHV-1 RacH-SE70-455-H3

Anti-H3 monoclonal antibody

FIG. 10
A.
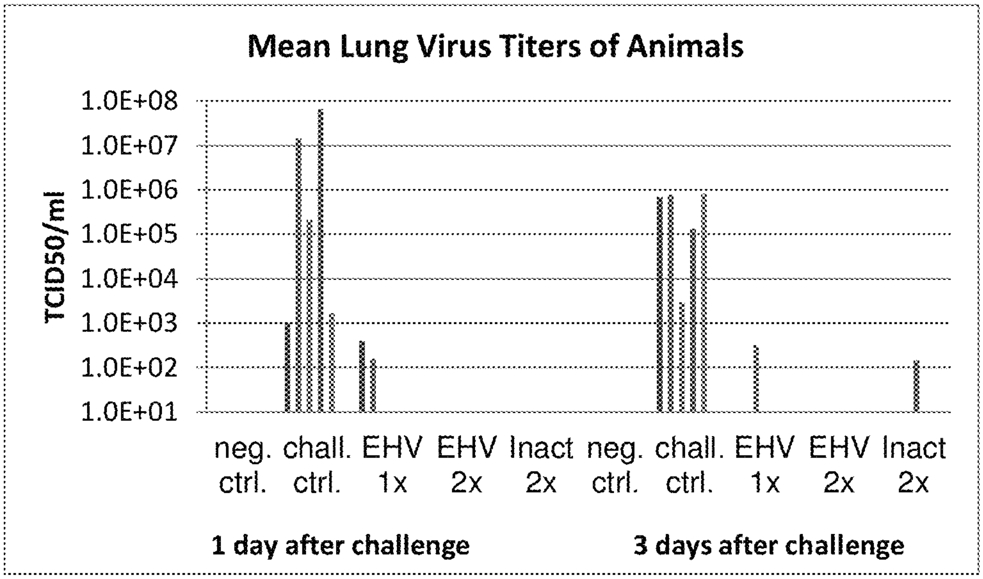
B.
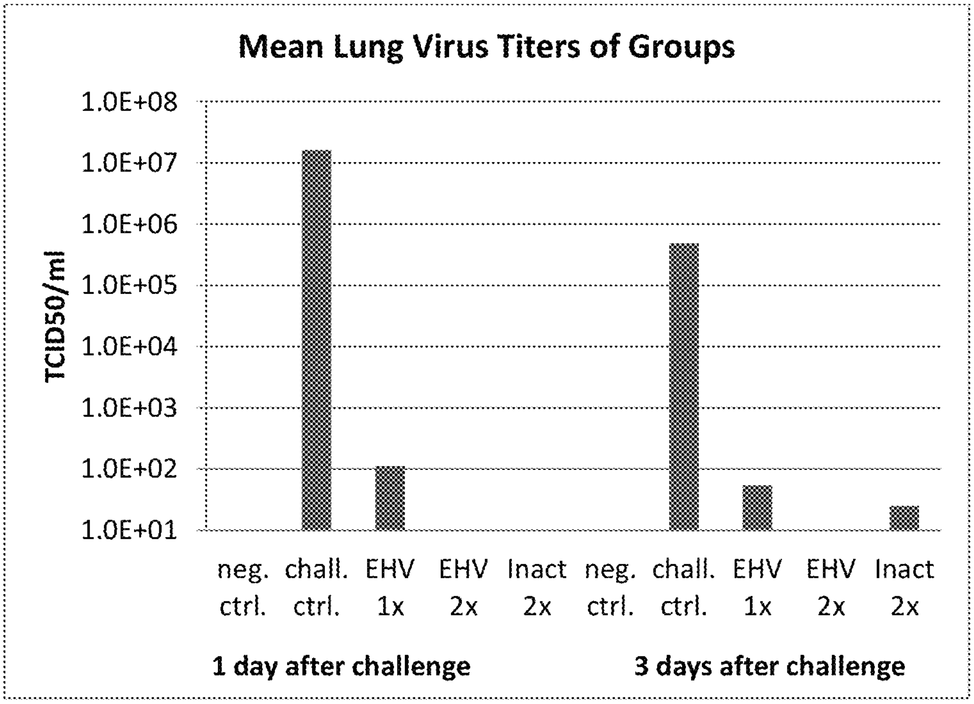

FIG. 11

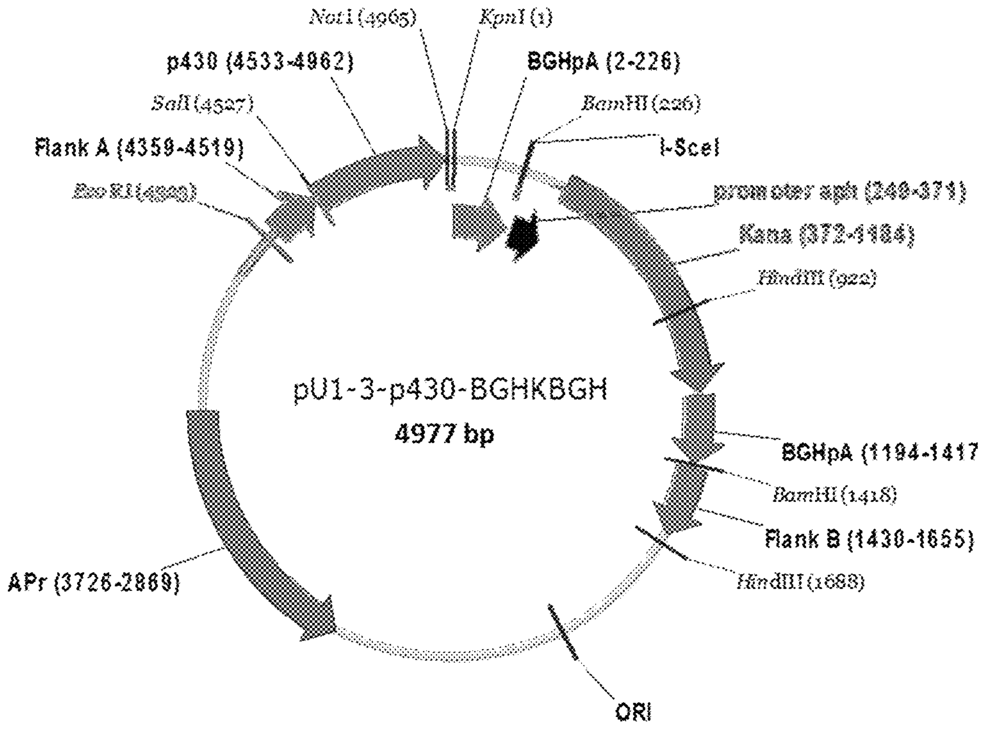

| | |
|---|---|
| **Flank A** | viral genomic DNA sequence flanking the insertion site upstream |
| **Flank B** | viral genomic DNA sequence flanking the insertion site downstream |
| **p430** | promoter driving expression of the transgene |
| **BGHpA** | polyadenylation sequence |
| **I-Sce1** | cleavage site for I-Sce1 |
| **promoter aph** | prokaryotic promoter driving expression of Kanamycin-resistence gene |
| **Kana** | Kanamycine resistance orf |
| **ORI** | origin of replication of plasmid vector |
| **Apr** | Ampicillin-resistance gene |

EcoRI, SalI, NotI, HindIII, KpnI, BamHI indicate restriction endonuclease cleavage sites

FIG. 12

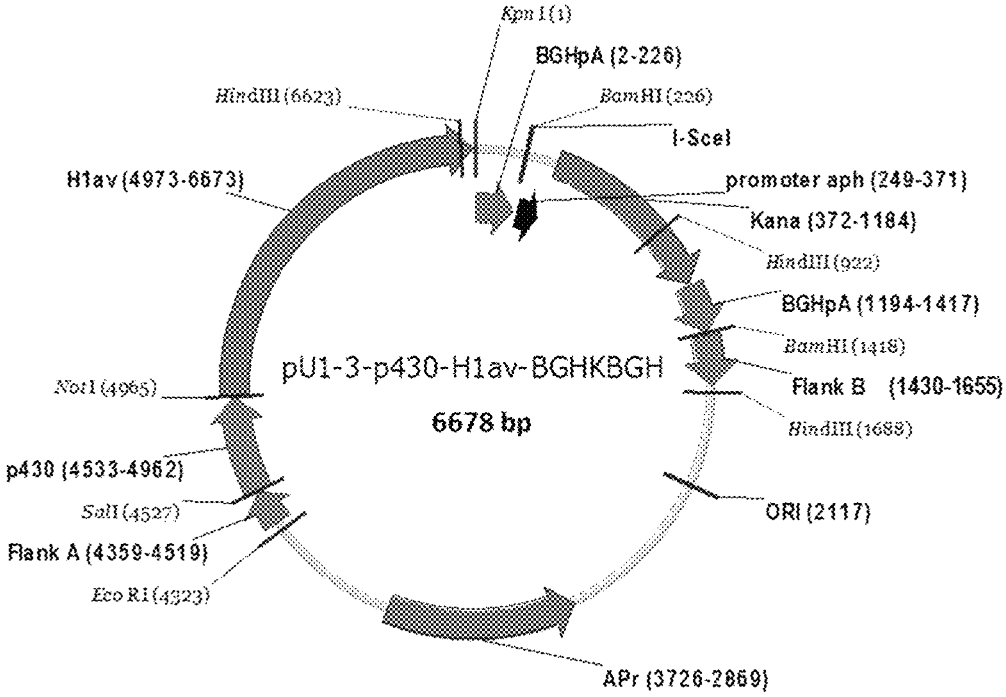

| | |
|---|---|
| **Flank A** | viral genomic DNA sequence flanking the insertion site upstream |
| **Flank B** | viral genomic DNA sequence flanking the insertion site downstream |
| **p430** | promoter driving expression of the transgene |
| **H1av** | transgene (IAV hemagglutinin) |
| **BGHpA** | polyadenylation sequence |
| **I-Sce1** | cleavage site for I-Sce1 |
| **promoter aph** | prokaryotic promoter driving expression of Kanamycin-resistence gene |
| **Kana** | Kanamycine resistance orf |
| **ORI** | origin of replication of plasmid vector |
| **Apr** | Ampicillin-resistance gene |

EcoRI, SalI, NotI, HindIII, KpnI, BamHI indicate restriction endonuclease cleavage sites

H1av = rEHV-1 RacH-SE1/3-430-H1av
SE = rEHV-RacH-SE (control)
mock = uninfected cells (control)

FIG. 21
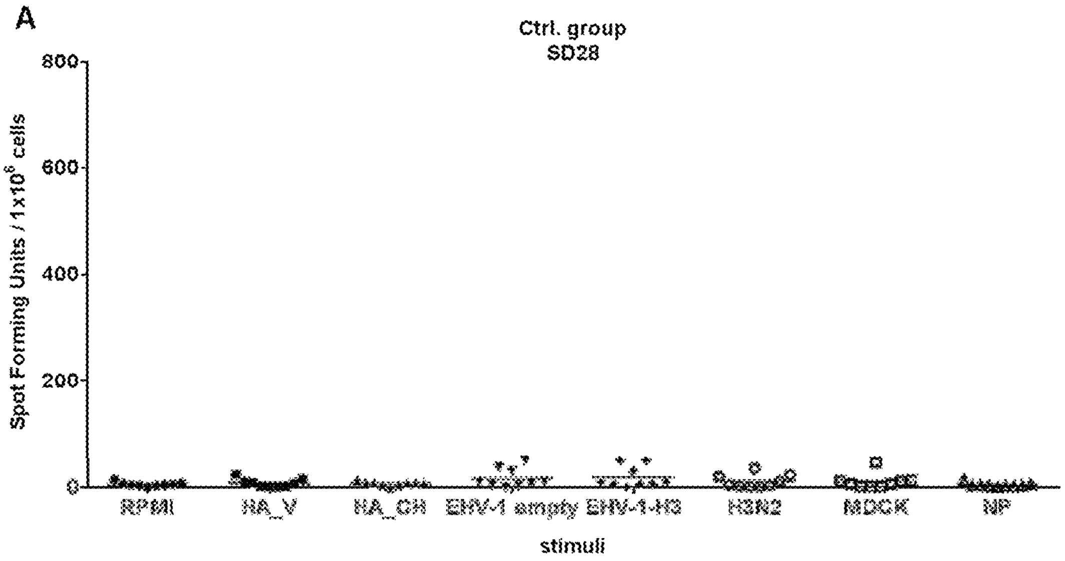
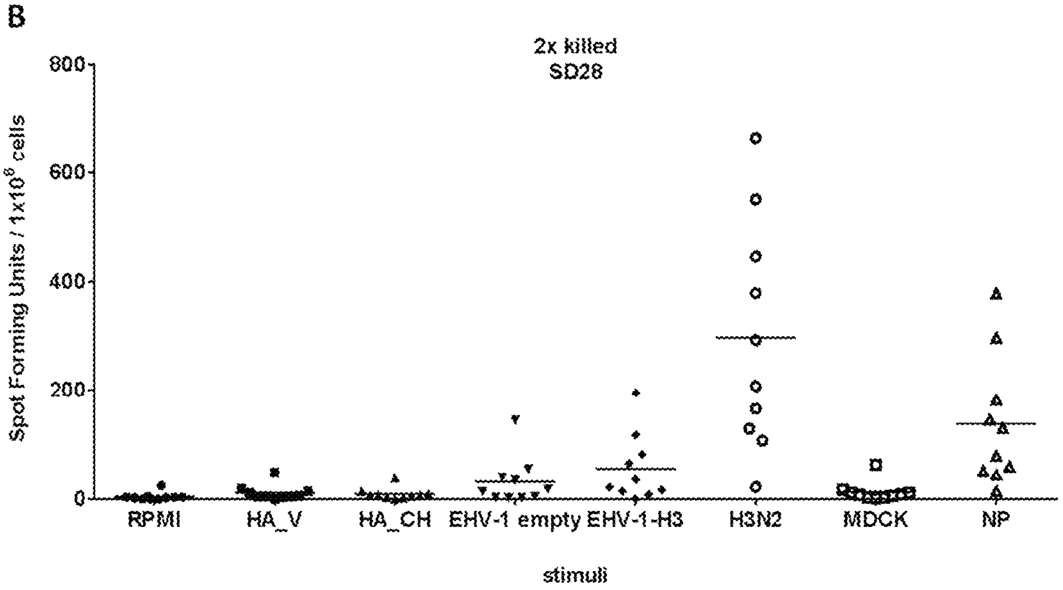

FIG. 22

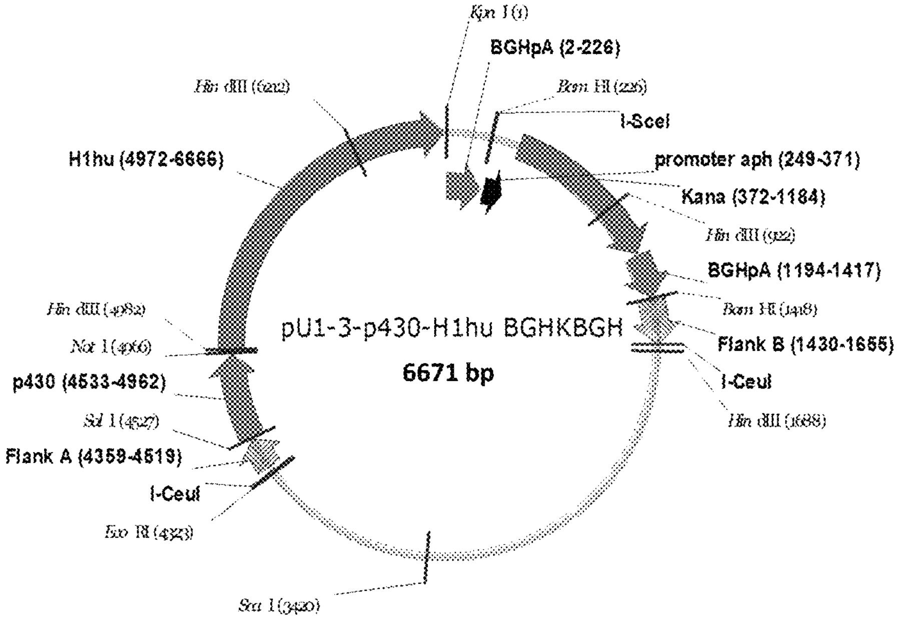

| | |
|---|---|
| **Flank A** | viral genomic DNA sequence flanking the insertion site upstream |
| **Flank B** | viral genomic DNA sequence flanking the insertion site downstream |
| **p430** | promoter driving expression of the transgene |
| **H1hu** | transgene (IAV hemagglutinin) |
| **BGHpA** | polyadenylation sequence |
| **I-Sce1** | cleavage site for I-Sce1 |
| **I-Ceu 1** | cleavage site for I-Ceu1 |
| **promoter aph** | prokaryotic promoter driving expression of Kanamycin-resistence gene |
| **Kana** | Kanamycine resistance orf |

ScaI, EcoRI, SalI, NotI, HindIII, KpnI, BamHI indicate restriction endonuclease cleavage sites

FIG. 23

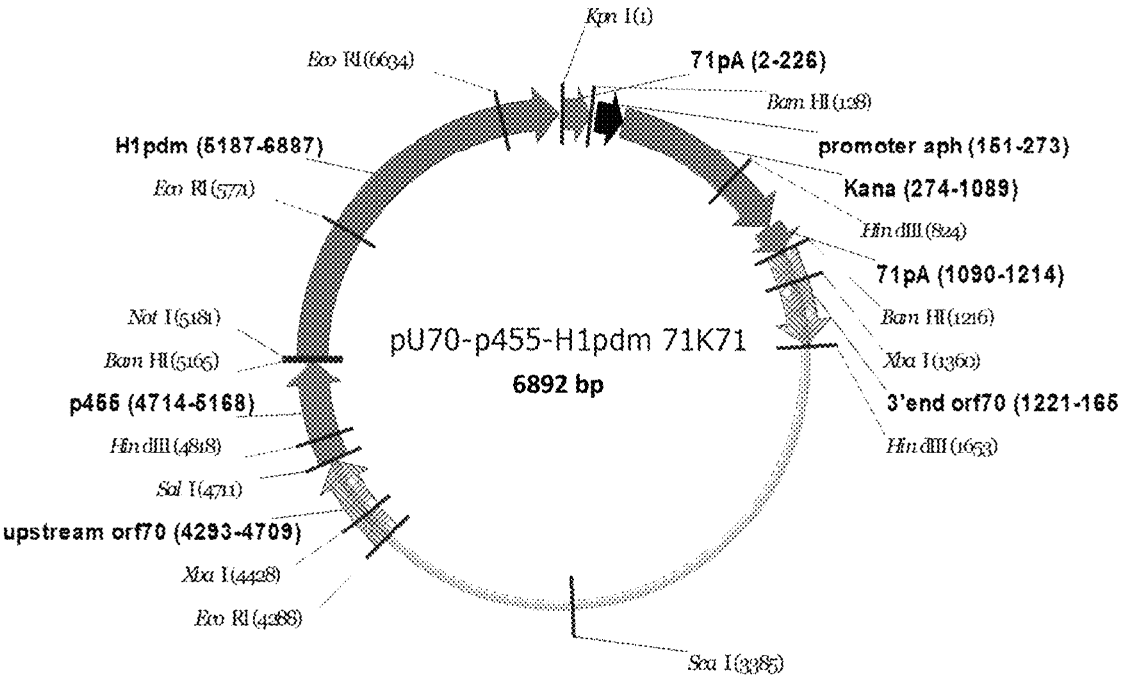

| | |
|---|---|
| **3'end ORF69** | viral genomic DNA sequence flanking the insertion site upstream |
| **3'end ORF70** | viral genomic DNA sequence flanking the insertion site downstream |
| **p455** | promoter driving expression of transgene |
| **H1pdm** | transgene (IAV hemagglutinin) |
| **71pA** | polyadenylation sequence |
| **I-Sce1** | cleavage site for I-Sce1 |
| **promoter aph** | prokaryotic promoter driving expression of Kanamycin-resistence gene |
| **Kana** | Kanamycine resistance orf |

ScaI, EcoRI, SalI, NotI, HindIII, KpnI, BamHI, XbaI indicate restriction endonuclease cleavage sites

SEQUENCE LISTING

```
<160> NUMBER OF SEQ ID NOS: 29

<210> SEQ ID NO 1
<211> LENGTH: 600
<212> TYPE: DNA
<213> ORGANISM: Equine herpesvirus 4

<400> SEQUENCE: 1

gcagactttg gagcagcaca atttccggtt gtggacccca tggaccttgg tttggctggt      60

accgtggaaa ctaacgctcc ggaagttttg gccagagcaa aatacaattc gaaggtagac     120

atatggagcg ccggaatagt tctgtttgaa atgctcgcat atccatcaac tctatttgag     180

gacccgccga gtaccccaca agagtatgta aaaagctgtc attctcaact actgagaata     240

atatcaaagc taaagataaa ccctgaggag tttccacggg aaccagagtc taggctcgtg     300

cgcggataca tcgaatacgc cagcctagag cgtaagccac atacgcgcta tccttgcttc     360

cagcgcgtga acctacacat tgacggggaa tttttgatcc ataaaatgct agcgttcaat     420

gctgcgatgc gcccatccgc agaagagttg ttgtcctacc caatgtttat gaatctgtag     480

gatgactaac agatttgggg tggagacggc gtgggcgata ctgtataaag ttgtactact     540

taccagccca gtcagtgtgc tgtagtgcca ccacctgtaa agctgtgata agctgcagtt     600


<210> SEQ ID NO 2
<211> LENGTH: 600
<212> TYPE: DNA
<213> ORGANISM: Equine herpesvirus 4

<400> SEQUENCE: 2

agctggggga gtttgtacta tagtgtatta catgcggctt gcaataactg cctggtttat      60

gtttcgcaac attcaagcag acatgctacc gctaaacact ttgcaacaat tttttattgg     120

gtgtttggcc tttggtagaa ctgtcgcgtt tttggtggta gcatatacta ccttatttat     180

acgctccgag ctgtttttca gcatgctagc acccaacgcc gagcgagagt atataactcc     240

catcattgcc cacaagctta tgccacttat tagcgtccgc tctgccgttt gcttagtcat     300

aatatctacc gccgtttacg cagcagacgc tatctgcgac acaattggat ttgcgatacc     360

gcgcatgtgg atgtgtattt taatgagatc aacctccatg aagcgtaact agggggcctc     420

ccactgaggc actaccggct tagcagctga ctaacacagt ataaaacgtg agaagaaatc     480

agtctcatgc gccattagcg ctaggctagt tagcgtggag gaccggagcg ctaccgccag     540

cagtttcatc cgcctggtta cgggtttgtt aacacctacc ggtgttttac cgctaccata     600


<210> SEQ ID NO 3
<211> LENGTH: 430
<212> TYPE: DNA
<213> ORGANISM: Equine herpesvirus 4

<400> SEQUENCE: 3
```

-continued

```
tctatttgag gacccgccga gtaccccaca agagtatgta aaaagctgtc attctcaact      60

actgagaata atatcaaagc taaagataaa ccctgaggag tttccacggg aaccagagtc     120

taggctcgtg cgcggataca tcgaatacgc cagcctagag cgtaagccac atacgcgcta     180

tccttgcttc cagcgcgtga acctacacat tgacggggaa tttttgatcc ataaaatgct     240

agcgttcaat gctgcgatgc gcccatccgc agaagagttg ttgtcctacc caatgtttat     300

gaatctgtag gatgactaac agatttgggg tggagacggc gtgggcgata ctgtataaag     360

ttgtactact taccagccca gtcagtgtgc tgtagtgcca ccacctgtaa agctgtgata     420

agctgcagtt                                                            430
```

<210> SEQ ID NO 4
<211> LENGTH: 449
<212> TYPE: DNA
<213> ORGANISM: Equine herpesvirus 4

<400> SEQUENCE: 4

```
ttggtggtag catatactac cttatttata cgctccgagc tgtttttcag catgctagca      60

cccaacgccg agcgagagta tataactccc atcattgccc acaagcttat gccacttatt     120

agcgtccgct ctgccgtttg cttagtcata atatctaccg ccgtttacgc agcagacgct     180

atctgcgaca caattggatt tgcgataccg cgcatgtgga tgtgtatttt aatgagatca     240

acctccatga agcgtaacta gggggcctcc cactgaggca ctaccggctt agcagctgac     300

taacacagta taaaacgtga gaagaaatca gtctcatgcg ccattagcgc taggctagtt     360

agcgtggagg accggagcgc taccgccagc agtttcatcc gcctggttac gggtttgtta     420

acacctaccg gtgttttacc gctaccata                                       449
```

<210> SEQ ID NO 5
<211> LENGTH: 20
<212> TYPE: DNA
<213> ORGANISM: Artificial Sequence
<220> FEATURE:
<223> OTHER INFORMATION: primer no 1130 specific for orf72

<400> SEQUENCE: 5

```
tgtctacctt caagcttatg                                                  20
```

<210> SEQ ID NO 6
<211> LENGTH: 17
<212> TYPE: DNA
<213> ORGANISM: Artificial Sequence
<220> FEATURE:
<223> OTHER INFORMATION: primer no 1131 specific for orf72

<400> SEQUENCE: 6

```
ctagcgcagt cgcgttg                                                     17
```

<210> SEQ ID NO 7
<211> LENGTH: 18
<212> TYPE: DNA
<213> ORGANISM: Artificial Sequence
<220> FEATURE:
<223> OTHER INFORMATION: primer no. 1079 specific for mCherry

<400> SEQUENCE: 7

```
gcgaggagga taacatgg                                                    18
```

<210> SEQ ID NO 8
<211> LENGTH: 18

<212> TYPE: DNA
<213> ORGANISM: Artificial Sequence
<220> FEATURE:
<223> OTHER INFORMATION: primer no. 1080 specific for mCherry

<400> SEQUENCE: 8
acccttggtc accttcag 18

<210> SEQ ID NO 9
<211> LENGTH: 22
<212> TYPE: DNA
<213> ORGANISM: Artificial Sequence
<220> FEATURE:
<223> OTHER INFORMATION: Artificial sequence nucleic acid PCR primer 1017 for the orf70 insertion region

<400> SEQUENCE: 9
aggctcgtgc gcggatacat cg 22

<210> SEQ ID NO 10
<211> LENGTH: 22
<212> TYPE: DNA
<213> ORGANISM: Artificial Sequence
<220> FEATURE:
<223> OTHER INFORMATION: Artificial sequence nucleic acid PCR primer 1018 for the orf70 insertion region

<400> SEQUENCE: 10
ttcggggctg ttagactcct cc 22

<210> SEQ ID NO 11
<211> LENGTH: 22
<212> TYPE: DNA
<213> ORGANISM: Artificial Sequence
<220> FEATURE:
<223> OTHER INFORMATION: Artificial sequence nucleic acid PCR primer 1007 for the orf1/3 insertion region

<400> SEQUENCE: 11
ccaactcgcc gccatgagac cc 22

<210> SEQ ID NO 12
<211> LENGTH: 22
<212> TYPE: DNA
<213> ORGANISM: Artificial Sequence
<220> FEATURE:
<223> OTHER INFORMATION: Artificial sequence nucleic acid PCR primer 1008 for the orf1/3 insertion region

<400> SEQUENCE: 12
agcgcgcccc gtacccagtg gg 22

<210> SEQ ID NO 13
<211> LENGTH: 417
<212> TYPE: DNA
<213> ORGANISM: Equine herpesvirus 1

<400> SEQUENCE: 13
ctccgagtac cccagaggag tatgtgaaaa gctgccactc gcaactactg aagataattt 60
caacgctcaa gataaatccg gaggagtttc ctcgagaccc cgggtcgagg ctcgtgcgcg 120
gatacatcga gtattctaga ctcgagcgca agccctacac gcgctacccc tgctttcaac 180
gcgtcaacct gcacattgac ggggagtttc tggttcacaa gatgctagcg ttcaatgccg 240
cgatgcgccc atcggccgag gagctgctgt catacccaat gtttgctcaa ctttaggatg 300
actaacctgt ttctgggagg agacagcgtg ggcgacggtg tataaagttg gtctgctttc 360
aagccctgcc actgcgctac agtgccacca actgtaaagc ggtagtaagc tgcagtg 417

<210> SEQ ID NO 14
<211> LENGTH: 431
<212> TYPE: DNA
<213> ORGANISM: Equine herpesvirus 1

<400> SEQUENCE: 14
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc tagaaaacca atcgacacag gaggagtcta acagccccga 180
agttgcccac ctgcgaagcg tcaacagcga tgacagtaca cacacggggg gtgcgtcgaa 240
cggcatccag gactgtgaca gtcagctcaa aactgtgtat gcctgcttgg ctctaattgg 300
actcggcaca tgtgccatga tagggttgat agtttacatt tgtgtattaa ggtcaaaact 360
gtcctctcgg aatttttcgc gcgcgcaaaa tgtaaaacat agaaattacc agcgacttga 420
gtacgttgct t 431

<210> SEQ ID NO 15
<211> LENGTH: 417
<212> TYPE: DNA
<213> ORGANISM: Equine herpesvirus 1

<400> SEQUENCE: 15
ctccgagtac cccagaggag tatgtgaaaa gctgccactc gcaactactg aagataattt 60
caacgctcaa gataaatccg gaggagtttc ctcgagaccc cgggtcgagg ctcgtgcgcg 120
gatacatcga gtattctaga ctcgagcgca agccctacac gcgctacccc tgctttcaac 180
gcgtcaacct gcacattgac ggggagtttc tggttcacaa gatgctagcg ttcaatgccg 240
cgatgcgccc atcggccgag gagctgctgt catacccaat gtttgcacaa ctttaggatg 300
actaacctgt ttctgggagg agacagcgtg ggcgacggtg tataaagttg gtctgctttc 360
aagccctgcc actgcgctac agtgccacca actgtaaagc ggtagtaagc tgcagtg 417

<210> SEQ ID NO 16
<211> LENGTH: 431
<212> TYPE: DNA
<213> ORGANISM: Equine herpesvirus 1

<400> SEQUENCE: 16
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc tagaaaacca atcgacacag gaggagtcta acagccccga 180
agttgcccac ctgcgaagcg tcaacagcga tgacagtaca cacacggggg gtgcgtcgaa 240
cggcatccag gactgtgaca gtcagctcaa aactgtgtat gcctgcttgg ctctaattgg 300
actcggcaca tgtgccatga tagggttgat agtttacatt tgtgtattaa ggtcaaaact 360
gtcctctcgg aatttttcgc gcgcgcaaaa tgtaaaacat agaaattacc agcgacttga 420
gtacgttgct t 431

<210> SEQ ID NO 17
<211> LENGTH: 283
<212> TYPE: DNA
<213> ORGANISM: Equine herpesvirus 1

<400> SEQUENCE: 17
tctagactcg agcgcaagcc ctacacgcgc taccccctgct ttcaacgcgt caacctgcac 60
attgacgggg agtttctggt tcacaagatg ctagcgttca atgccgcgat gcgcccatcg 120
gccgaggagc tgctgtcata cccaatgttt gctcaacttt aggatgacta acctgtttct 180
gggaggagac agcgtgggcg acggtgtata aagttggtct gctttcaagc cctgccactg 240
cgctacagtg ccaccaactg taaagcggta gtaagctgca gtg 283

<210> SEQ ID NO 18
<211> LENGTH: 144
<212> TYPE: DNA
<213> ORGANISM: Equine herpesvirus 1

<400> SEQUENCE: 18
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc taga 144

<210> SEQ ID NO 19
<211> LENGTH: 801
<212> TYPE: DNA
<213> ORGANISM: Equine herpesvirus 1

<400> SEQUENCE: 19
atgttgactg tcttagcagc cctgagtctg ctcagcttgc ttacgagcgc aaccggacgg 60
ctcgccccag atgaactctg ttatgccgaa ccccgcagaa ctggcagccc accaaacacc 120
cagcccgaac gcccacccgt aatatttgag cccccaacaa ttgcgattaa agctgaatcc 180
aagggttgtg agctaatttt attagatcca cccatagatg taagctatcg cagagaagat 240
aaggtgaatg cgtccattgc ttggtttttt gactttggcg cttgccggat gcccatcgca 300
tacagagagt attacggttg tattggcaat gctgttccct ccccagagac ttgtgatgcg 360
tactcattta cccttattag gaccgagggt atcgtggagt ttaccatcgt aaacatgagc 420
ctcctgtttc agcctggaat atacgatagt ggcaatttta tctacagcgt tctcctggac 480
taccacatat ttacaggacg tgtaacgttg gaagtggaaa aggacacaaa ctatccctgt 540
ggcatgattc atggactcac tgcttacgga aacatcaacg tagatgaaac catggacaac 600
gccagcccac acccgcgtgc cgtggggtgc tttcccgagc ccatcgacaa cgaagcgtgg 660
gcaaacgtta catttactga attggggata ccagacccaa actcatttct cgatgacgag 720
ggtgattacc cgaatatatc agactgtcac tcgtgggagt catacaccta cccaaatacg 780
ctgaggcagg ccacaggacc c 801

<210> SEQ ID NO 20
<211> LENGTH: 801
<212> TYPE: DNA
<213> ORGANISM: Equine herpesvirus 1

<400> SEQUENCE: 20
atgttgactg tcttagcagc tctgagtctg ctcagcttgc ttacgagcgc aaccggacgg 60
ctcgccccag atgaactctg ttatgccgaa ccccgcagaa ctggcagccc accaaacacc 120
cagcccgaac gcccacccgt aatatttgag cccccaacaa ttgcgattaa agctgaatcc 180
aagggttgtg agctaatttt attagatcca cccatagatg taagctatcg cagagaagat 240

```
aggtgaatg cgtccattgc ttggtttttt gactttggcg cttgccggat gcccatcgca    300

tacagagagt attacggttg tattggcaat gctgttccct ccccagagac ttgtgatgcg    360

tactcattta cccttattag gaccgagggt atcgtggagt ttaccatcgt aaacatgagc    420

ctcctgtttc agcctggaat atacgatagt ggcaatttta tctacagcgt tctcctggac    480

taccacatat ttacaggacg tgtaacgttg gaagtggaaa aggacacaaa ctatccctgt    540

ggcatgattc atggactcac tgcttacgga aacatcaacg tagatgaaac catggacaac    600

gccagcccac acccgcgtgc cgtggggtgc tttcccgagc ccatcgacaa cgaagcgtgg    660

gcaaacgtta catttactga attggggata ccagacccaa actcatttct cgatgacgag    720

ggtgattacc cgaatatatc agactgtcac tcgtgggagt catacaccta cccaaatacg    780

ctgaggcagg ccacaggacc c                                              801
```

<210> SEQ ID NO 21
<211> LENGTH: 4435
<212> TYPE: DNA
<213> ORGANISM: Artificial Sequence
<220> FEATURE:
<223> OTHER INFORMATION: Nucleotide sequence of transfer plasmid pU-mC70-BGH

<400> SEQUENCE: 21

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cctccgagta ccccagagga    420

gtatgtgaaa agctgccact cgcaactact gaagataatt tcaacgctca agataaatcc    480

ggaggagttt cctcgagacc ccgggtcgag gctcgtgcgc ggatacatcg agtattctag    540

actcgagcgc aagccctaca cgcgctaccc ctgctttcaa cgcgtcaacc tgcacattga    600

cggggagttt ctggttcaca agatgctagc gttcaatgcc gcgatgcgcc catcggccga    660

ggagctgctg tcatacccaa tgtttgctca actttaggat gactaacctg tttctgggag    720

gagacagcgt gggcgacggt gtataaagtt ggtctgcttt caagccctgc cactgcgcta    780

cagtgccacc aactgtaaag cggtagtaag ctgcagtggt cgacatggtg agcaagggcg    840

aggaggataa catggccatc atcaaggagt tcatgcgctt caaggtgcac atggagggct    900

ccgtgaacgg ccacgagttc gagatcgagg gcgagggcga gggccgcccc tacgagggca    960

cccagaccgc caagctgaag gtgaccaagg gtggccccct gcccttcgcc tgggacatcc   1020

tgtcccctca gttcatgtac ggctccaagg cctacgtgaa gcaccccgcc gacatccccg   1080

actacttgaa gctgtccttc cccgagggct tcaagtggga gcgcgtgatg aacttcgagg   1140

acggcggcgt ggtgaccgtg acccaggact cctccctgca ggacggcgag ttcatctaca   1200

aggtgaagct gcgcggcacc aacttcccct ccgacggccc cgtaatgcag aagaagacca   1260

tgggctggga ggcctcctcc gagcggatgt accccgagga cggcgccctg aagggcgaga   1320

tcaagcagag gctgaagctg aaggacggcg gccactacga cgctgaggtc aagaccacct   1380

acaaggccaa gaagcccgtg cagctgcccg gcgcctacaa cgtcaacatc aagttggaca   1440
```

-continued

```
tcacctccca caacgaggac tacaccatcg tggaacagta cgaacgcgcc gagggccgcc   1500
actccaccgg cggcatggac gagctgtaca agtaactgtg ccttctagtt gccagccatc   1560
tgttgtttgc ccctcccccg tgccttcctt gaccctggaa ggtgccactc ccactgtcct   1620
ttcctaataa aatgaggaaa ttgcatcgca ttgtctgagt aggtgtcatt ctattctggg   1680
gggtggggtg gggcaggaca gcaaggggga ggattgggaa gacaatagca ggcatgctgg   1740
ggatgcggtg ggctctatgg atccgaccct gttggtgggt gcggttggac tcagaatctt   1800
ggcgcaggca tggaagtttg tcggtgacga aacatacgac accatccgcg cagaagcaaa   1860
gaatttagag acccacgtac cctcaagtgc tgcagagtcg tctctagaaa accaatcgac   1920
acaggaggag tctaacagcc ccgaagttgc ccacctgcga agcgtcaaca gcgatgacag   1980
tacacacacg gggggtgcgt cgaacggcat ccaggactgt gacagtcagc tcaaaactgt   2040
gtatgcctgc ttggctctaa ttggactcgg cacatgtgcc atgatagggt tgatagttta   2100
catttgtgta ttaaggtcaa aactgtcctc tcggaatttt tcgcgcgcgc aaaatgtaaa   2160
acatagaaat taccagcgac ttgagtacgt tgcttaagct tggcgtaatc atggtcatag   2220
ctgtttcctg tgtgaaattg ttatccgctc acaattccac acaacatacg agccggaagc   2280
ataaagtgta aagcctgggg tgcctaatga gtgagctaac tcacattaat tgcgttgcgc   2340
tcactgcccg ctttccagtc gggaaacctg tcgtgccagc tgcattaatg aatcggccaa   2400
cgcgcgggga gaggcggttt gcgtattggg cgctcttccg cttcctcgct cactgactcg   2460
ctgcgctcgg tcgttcggct gcggcgagcg gtatcagctc actcaaaggc ggtaatacgg   2520
ttatccacag aatcagggga taacgcagga aagaacatgt gagcaaaagg ccagcaaaag   2580
gccaggaacc gtaaaaaggc cgcgttgctg gcgtttttcc ataggctccg cccccctgac   2640
gagcatcaca aaaatcgacg ctcaagtcag aggtggcgaa acccgacagg actataaaga   2700
taccaggcgt ttccccctgg aagctccctc gtgcgctctc ctgttccgac cctgccgctt   2760
accggatacc tgtccgcctt tctcccttcg ggaagcgtgg cgctttctca tagctcacgc   2820
tgtaggtatc tcagttcggt gtaggtcgtt cgctccaagc tgggctgtgt gcacgaaccc   2880
cccgttcagc ccgaccgctg cgccttatcc ggtaactatc gtcttgagtc caacccggta   2940
agacacgact tatcgccact ggcagcagcc actggtaaca ggattagcag agcgaggtat   3000
gtaggcggtg ctacagagtt cttgaagtgg tggcctaact acggctacac tagaaggaca   3060
gtatttggta tctgcgctct gctgaagcca gttaccttcg gaaaaagagt tggtagctct   3120
tgatccggca aacaaaccac cgctggtagc ggtggttttt ttgtttgcaa gcagcagatt   3180
acgcgcagaa aaaaaggatc tcaagaagat cctttgatct tttctacggg gtctgacgct   3240
cagtggaacg aaaactcacg ttaagggatt ttggtcatga gattatcaaa aaggatcttc   3300
acctagatcc ttttaaatta aaaatgaagt tttaaatcaa tctaaagtat atatgagtaa   3360
acttggtctg acagttacca atgcttaatc agtgaggcac ctatctcagc gatctgtcta   3420
tttcgttcat ccatagttgc ctgactcccc gtcgtgtaga taactacgat acgggagggc   3480
ttaccatctg gccccagtgc tgcaatgata ccgcgagacc cacgctcacc ggctccagat   3540
ttatcagcaa taaaccagcc agccggaagg gccgagcgca gaagtggtcc tgcaacttta   3600
tccgcctcca tccagtctat taattgttgc cgggaagcta gagtaagtag ttcgccagtt   3660
aatagtttgc gcaacgttgt tgccattgct acaggcatcg tggtgtcacg ctcgtcgttt   3720
ggtatggctt cattcagctc cggttcccaa cgatcaaggc gagttacatg atcccccatg   3780
ttgtgcaaaa aagcggttag ctccttcggt cctccgatcg ttgtcagaag taagttggcc   3840
```

gcagtgttat cactcatggt tatggcagca ctgcataatt ctcttactgt catgccatcc 3900
gtaagatgct tttctgtgac tggtgagtac tcaaccaagt cattctgaga atagtgtatg 3960
cggcgaccga gttgctcttg cccggcgtca atacgggata ataccgcgcc acatagcaga 4020
actttaaaag tgctcatcat tggaaaacgt tcttcggggc gaaaactctc aaggatctta 4080
ccgctgttga gatccagttc gatgtaaccc actcgtgcac ccaactgatc ttcagcatct 4140
tttactttca ccagcgtttc tgggtgagca aaaacaggaa ggcaaaatgc cgcaaaaaag 4200
ggaataaggg cgacacggaa atgttgaata ctcatactct tcctttttca atattattga 4260
agcatttatc agggttattg tctcatgagc ggatacatat ttgaatgtat ttagaaaaat 4320
aaacaaatag gggttccgcg cacatttccc cgaaaagtgc cacctgacgt ctaagaaacc 4380
attattatca tgacattaac ctataaaaat aggcgtatca cgaggccctt tcgtc 4435

<210> SEQ ID NO 22
<211> LENGTH: 5191
<212> TYPE: DNA
<213> ORGANISM: Artificial Sequence
<220> FEATURE:
<223> OTHER INFORMATION: Nucleotide sequence of transfer vector
pU70-p455-71K71

<400> SEQUENCE: 22
caataaacgc ggtatgtcta ccttcaagcc tatgatgaac ggatgtttgg tgtttgcggc 60
tattataacg ctcttgagtt ttatgctatc tctgggaaca tgcgaaaatt acaggcgtgt 120
ggttcgggat cctagggata acagggtaat cgatttattc aacaaagcca cgttgtgtct 180
caaaatctct gatgttacat tgcacaagat aaaaatatat catcatgaac aataaaactg 240
tctgcttaca taaacagtaa tacaaggggt gttatgagcc atattcaacg ggaaacgtct 300
tgctcgaggc cgcgattaaa ttccaacatg gatgctgatt tatatgggta taaatgggct 360
cgcgataatg tcgggcaatc aggtgcgaca atctatcgat tgtatgggaa gcccgatgcg 420
ccagagttgt ttctgaaaca tggcaaaggt agcgttgcca atgatgttac agatgagatg 480
gtcagactaa actggctgac ggaatttatg cctcttccga ccatcaagca ttttatccgt 540
actcctgatg atgcatggtt actcaccact gcgatccccg ggaaaacagc attccaggta 600
ttagaagaat atcctgattc aggtgaaaat attgttgatg cgctggcagt gttcctgcgc 660
cggttgcatt cgattcctgt ttgtaattgt ccttttaaca gcgatcgcgt atttcgtctc 720
gctcaggcgc aatcacgaat gaataacggt ttggttgatg cgagtgattt tgatgacgag 780
cgtaatggct ggcctgttga acaagtctgg aaagaaatgc ataagctttt gccattctca 840
ccggattcag tcgtcactca tggtgatttc tcacttgata accttatttt tgacgagggg 900
aaattaatag gttgtattga tgttggacga gtcggaatcg cagaccgata ccaggatctt 960
gccatcctat ggaactgcct cggtgagttt tctccttcat tacagaaacg gctttttcaa 1020
aaatatggta ttgataatcc tgatatgaat aaattgcagt ttcatttgat gctcgatgag 1080
tttttctaaa ataaacgcgg tatgtctacc ttcaagccta tgatgaacgg atgtttggtg 1140
tttgcggcta ttataacgct cttgagtttt atgctatctc tgggaacatg cgaaaattac 1200
aggcgtgtgg ttcgggatcc gaccctgttg gtgggtgcgg ttggactcag aatcttggcg 1260
caggcatgga agtttgtcgg tgacgaaaca tacgacacca tccgcgcaga agcaaagaat 1320
ttagagaccc acgtaccctc aagtgctgca gagtcgtctc tagaaaacca atcgacacag 1380
gaggagtcta acagccccga agttgcccac ctgcgaagcg tcaacagcga tgacagtaca 1440
cacacggggg gtgcgtcgaa cggcatccag gactgtgaca gtcagctcaa aactgtgtat 1500
gcctgcttgg ctctaattgg actcggcaca tgtgccatga tagggttgat agtttacatt 1560
tgtgtattaa ggtcaaaact gtcctctcgg aatttttcgc gcgcgcaaaa tgtaaaacat 1620
agaaattacc agcgacttga gtacgttgct taagcttggc gtaatcatgg tcatagctgt 1680
ttcctgtgtg aaattgttat ccgctcacaa ttccacacaa catacgagcc ggaagcataa 1740
agtgtaaagc ctggggtgcc taatgagtga gctaactcac attaattgcg ttgcgctcac 1800
tgcccgcttt ccagtcggga aacctgtcgt gccagctgca ttaatgaatc ggccaacgcg 1860
cggggagagg cggtttgcgt attgggcgct cttccgcttc ctcgctcact gactcgctgc 1920
gctcggtcgt tcggctgcgg cgagcggtat cagctcactc aaaggcggta atacggttat 1980
ccacagaatc aggggataac gcaggaaaga acatgtgagc aaaaggccag caaaaggcca 2040
ggaaccgtaa aaaggccgcg ttgctggcgt ttttccatag gctccgcccc cctgacgagc 2100
atcacaaaaa tcgacgctca agtcagaggt ggcgaaaccc gacaggacta taaagatacc 2160
aggcgtttcc ccctggaagc tccctcgtgc gctctcctgt tccgaccctg ccgcttaccg 2220
gatacctgtc cgcctttctc ccttcgggaa gcgtggcgct ttctcatagc tcacgctgta 2280
ggtatctcag ttcggtgtag gtcgttcgct ccaagctggg ctgtgtgcac gaaccccccg 2340
ttcagcccga ccgctgcgcc ttatccggta actatcgtct tgagtccaac ccggtaagac 2400
acgacttatc gccactggca gcagccactg gtaacaggat tagcagagcg aggtatgtag 2460
gcggtgctac agagttcttg aagtggtggc ctaactacgg ctacactaga aggacagtat 2520
ttggtatctg cgctctgctg aagccagtta ccttcggaaa aagagttggt agctcttgat 2580
ccggcaaaca aaccaccgct ggtagcggtg gtttttttgt ttgcaagcag cagattacgc 2640
gcagaaaaaa aggatctcaa gaagatcctt tgatcttttc tacggggtct gacgctcagt 2700
ggaacgaaaa ctcacgttaa gggattttgg tcatgagatt atcaaaaagg atcttcacct 2760
agatcctttt aaattaaaaa tgaagtttta aatcaatcta aagtatatat gagtaaactt 2820
ggtctgacag ttaccaatgc ttaatcagtg aggcacctat ctcagcgatc tgtctatttc 2880
gttcatccat agttgcctga ctccccgtcg tgtagataac tacgatacgg gagggcttac 2940
catctggccc cagtgctgca atgataccgc gagacccacg ctcaccggct ccagatttat 3000
cagcaataaa ccagccagcc ggaagggccg agcgcagaag tggtcctgca actttatccg 3060
cctccatcca gtctattaat tgttgccggg aagctagagt aagtagttcg ccagttaata 3120
gtttgcgcaa cgttgttgcc attgctacag gcatcgtggt gtcacgctcg tcgtttggta 3180
tggcttcatt cagctccggt tcccaacgat caaggcgagt tacatgatcc cccatgttgt 3240
gcaaaaaagc ggttagctcc ttcggtcctc cgatcgttgt cagaagtaag ttggccgcag 3300
tgttatcact catggttatg gcagcactgc ataattctct tactgtcatg ccatccgtaa 3360
gatgcttttc tgtgactggt gagtactcaa ccaagtcatt ctgagaatag tgtatgcggc 3420
gaccgagttg ctcttgcccg gcgtcaatac gggataatac cgcgccacat agcagaactt 3480
taaaagtgct catcattgga aaacgttctt cggggcgaaa actctcaagg atcttaccgc 3540
tgttgagatc cagttcgatg taacccactc gtgcacccaa ctgatcttca gcatctttta 3600
ctttcaccag cgtttctggg tgagcaaaaa caggaaggca aaatgccgca aaaaagggaa 3660
taagggcgac acggaaatgt tgaatactca tactcttcct ttttcaatat tattgaagca 3720
tttatcaggg ttattgtctc atgagcggat acatatttga atgtatttag aaaaataaac 3780

-continued aaataggggt tccgcgcaca tttccccgaa aagtgccacc tgacgtctaa gaaaccatta 3840
ttatcatgac attaacctat aaaaataggc gtatcacgag gccctttcgt ctcgcgcgtt 3900
tcggtgatga cggtgaaaac ctctgacaca tgcagctccc ggagacggtc acagcttgtc 3960
tgtaagcgga tgccgggagc agacaagccc gtcagggcgc gtcagcgggt gttggcgggt 4020
gtcggggctg gcttaactat gcggcatcag agcagattgt actgagagtg caccatatgc 4080
ggtgtgaaat accgcacaga tgcgtaagga gaaaataccg catcaggcgc cattcgccat 4140
tcaggctgcg caactgttgg gaagggcgat cggtgcgggc ctcttcgcta ttacgccagc 4200
tggcgaaagg gggatgtgct gcaaggcgat taagttgggt aacgccaggg ttttcccagt 4260
cacgacgttg taaaacgacg gccagtgaat tcctccgagt accccagagg agtatgtgaa 4320
aagctgccac tcgcaactac tgaagataat ttcaacgctc aagataaatc cggaggagtt 4380
tcctcgagac cccgggtcga ggctcgtgcg cggatacatc gagtattcta gactcgagcg 4440
caagccctac acgcgctacc cctgctttca acgcgtcaac ctgcacattg acggggagtt 4500
tctggttcac aagatgctag cgttcaatgc cgcgatgcgc ccatcggccg aggagctgct 4560
gtcataccca atgtttgctc aactttagga tgactaacct gtttctggga ggagacagcg 4620
tgggcgacgg tgtataaagt tggtctgctt tcaagccctg ccactgcgct acagtgccac 4680
caactgtaaa gcggtagtaa gctgcagtgg tcgactggtg gtagcatata ctaccttatt 4740
tatacgctcc gagctgtttt tcagcatgct agcacccaac gccgagcgag agtatataac 4800
tcccatcatt gcccacaagc ttatgccact tattagcgtc cgctctgccg tttgcttagt 4860
cataatatct accgccgttt acgcagcaga cgctatctgc gacacaattg gatttgcgat 4920
accgcgcatg tggatgtgta ttttaatgag atcaacctcc atgaagcgta actagggggc 4980
ctcccactga ggcactaccg gcttagcagc tgactaacac agtataaaac gtgagaagaa 5040
atcagtctca tgcgccatta gcgctaggct agttagcgtg gaggaccgga gcgctaccgc 5100
cagcagtttc atccgcctgg ttacgggttt gttaacacct accggtgttt taccgctacc 5160
ataggatccg atccatgggc ggccgcggta c 5191

<210> SEQ ID NO 23
<211> LENGTH: 6892
<212> TYPE: DNA
<213> ORGANISM: Artificial Sequence
<220> FEATURE:
<223> OTHER INFORMATION: Nucleotide sequence of transfer plasmid
pU70-p455-H3-71K71

<400> SEQUENCE: 23
caataaacgc ggtatgtcta ccttcaagcc tatgatgaac ggatgtttgg tgtttgcggc 60
tattataacg ctcttgagtt ttatgctatc tctgggaaca tgcgaaaatt acaggcgtgt 120
ggttcgggat cctagggata acagggtaat cgatttattc aacaaagcca cgttgtgtct 180
caaaatctct gatgttacat tgcacaagat aaaaatatat catcatgaac aataaaactg 240
tctgcttaca taaacagtaa tacaaggggt gttatgagcc atattcaacg ggaaacgtct 300
tgctcgaggc cgcgattaaa ttccaacatg gatgctgatt tatatgggta taaatgggct 360
cgcgataatg tcgggcaatc aggtgcgaca atctatcgat tgtatgggaa gcccgatgcg 420
ccagagttgt ttctgaaaca tggcaaaggt agcgttgcca atgatgttac agatgagatg 480
gtcagactaa actggctgac ggaatttatg cctcttccga ccatcaagca ttttatccgt 540
actcctgatg atgcatggtt actcaccact gcgatccccg ggaaaacagc attccaggta 600

-continued

```
ttagaagaat atcctgattc aggtgaaaat attgttgatg cgctggcagt gttcctgcgc    660
cggttgcatt cgattcctgt ttgtaattgt ccttttaaca gcgatcgcgt atttcgtctc    720
gctcaggcgc aatcacgaat gaataacggt ttggttgatg cgagtgattt tgatgacgag    780
cgtaatggct ggcctgttga acaagtctgg aaagaaatgc ataagctttt gccattctca    840
ccggattcag tcgtcactca tggtgatttc tcacttgata accttatttt tgacgagggg    900
aaattaatag gttgtattga tgttggacga gtcggaatcg cagaccgata ccaggatctt    960
gccatcctat ggaactgcct cggtgagttt tctccttcat tacagaaacg gctttttcaa   1020
aaatatggta ttgataatcc tgatatgaat aaattgcagt ttcatttgat gctcgatgag   1080
tttttctaaa ataaacgcgg tatgtctacc ttcaagccta tgatgaacgg atgtttggtg   1140
tttgcggcta ttataacgct cttgagtttt atgctatctc tgggaacatg cgaaaattac   1200
aggcgtgtgg ttcgggatcc gaccctgttg gtgggtgcgg ttggactcag aatcttggcg   1260
caggcatgga agtttgtcgg tgacgaaaca tacgacacca tccgcgcaga agcaaagaat   1320
ttagagaccc acgtaccctc aagtgctgca gagtcgtctc tagaaaacca atcgacacag   1380
gaggagtcta acagccccga agttgcccac ctgcgaagcg tcaacagcga tgacagtaca   1440
cacacggggg gtgcgtcgaa cggcatccag gactgtgaca gtcagctcaa aactgtgtat   1500
gcctgcttgg ctctaattgg actcggcaca tgtgccatga tagggttgat agtttacatt   1560
tgtgtattaa ggtcaaaact gtcctctcgg aatttttcgc gcgcgcaaaa tgtaaaacat   1620
agaaattacc agcgacttga gtacgttgct taagcttggc gtaatcatgg tcatagctgt   1680
ttcctgtgtg aaattgttat ccgctcacaa ttccacacaa catacgagcc ggaagcataa   1740
agtgtaaagc ctggggtgcc taatgagtga gctaactcac attaattgcg ttgcgctcac   1800
tgcccgcttt ccagtcggga aacctgtcgt gccagctgca ttaatgaatc ggccaacgcg   1860
cggggagagg cggtttgcgt attgggcgct cttccgcttc ctcgctcact gactcgctgc   1920
gctcggtcgt tcggctgcgg cgagcggtat cagctcactc aaaggcggta atacggttat   1980
ccacagaatc aggggataac gcaggaaaga acatgtgagc aaaaggccag caaaaggcca   2040
ggaaccgtaa aaaggccgcg ttgctggcgt ttttccatag gctccgcccc cctgacgagc   2100
atcacaaaaa tcgacgctca agtcagaggt ggcgaaaccc gacaggacta taaagatacc   2160
aggcgtttcc ccctggaagc tccctcgtgc gctctcctgt tccgaccctg ccgcttaccg   2220
gatacctgtc cgcctttctc ccttcgggaa gcgtggcgct ttctcatagc tcacgctgta   2280
ggtatctcag ttcggtgtag gtcgttcgct ccaagctggg ctgtgtgcac gaaccccccg   2340
ttcagcccga ccgctgcgcc ttatccggta actatcgtct tgagtccaac ccggtaagac   2400
acgacttatc gccactggca gcagccactg gtaacaggat tagcagagcg aggtatgtag   2460
gcggtgctac agagttcttg aagtggtggc ctaactacgg ctacactaga aggacagtat   2520
ttggtatctg cgctctgctg aagccagtta ccttcggaaa aagagttggt agctcttgat   2580
ccggcaaaca aaccaccgct ggtagcggtg gtttttttgt ttgcaagcag cagattacgc   2640
gcagaaaaaa aggatctcaa gaagatcctt tgatcttttc tacggggtct gacgctcagt   2700
ggaacgaaaa ctcacgttaa gggattttgg tcatgagatt atcaaaaagg atcttcacct   2760
agatcctttt aaattaaaaa tgaagtttta aatcaatcta aagtatatat gagtaaactt   2820
ggtctgacag ttaccaatgc ttaatcagtg aggcacctat ctcagcgatc tgtctatttc   2880
gttcatccat agttgcctga ctccccgtcg tgtagataac tacgatacgg gagggcttac   2940
catctggccc cagtgctgca atgataccgc gagacccacg ctcaccggct ccagatttat   3000
```

cagcaataaa ccagccagcc ggaagggccg agcgcagaag tggtcctgca actttatccg 3060
cctccatcca gtctattaat tgttgccggg aagctagagt aagtagttcg ccagttaata 3120
gtttgcgcaa cgttgttgcc attgctacag gcatcgtggt gtcacgctcg tcgtttggta 3180
tggcttcatt cagctccggt tcccaacgat caaggcgagt tacatgatcc cccatgttgt 3240
gcaaaaaagc ggttagctcc ttcggtcctc cgatcgttgt cagaagtaag ttggccgcag 3300
tgttatcact catggttatg gcagcactgc ataattctct tactgtcatg ccatccgtaa 3360
gatgcttttc tgtgactggt gagtactcaa ccaagtcatt ctgagaatag tgtatgcggc 3420
gaccgagttg ctcttgcccg gcgtcaatac gggataatac cgcgccacat agcagaactt 3480
taaaagtgct catcattgga aaacgttctt cggggcgaaa actctcaagg atcttaccgc 3540
tgttgagatc cagttcgatg taacccactc gtgcacccaa ctgatcttca gcatctttta 3600
ctttcaccag cgtttctggg tgagcaaaaa caggaaggca aaatgccgca aaaaagggaa 3660
taagggcgac acggaaatgt tgaatactca tactcttcct ttttcaatat tattgaagca 3720
tttatcaggg ttattgtctc atgagcggat acatatttga atgtatttag aaaaataaac 3780
aaataggggt tccgcgcaca tttccccgaa aagtgccacc tgacgtctaa gaaaccatta 3840
ttatcatgac attaacctat aaaaataggc gtatcacgag gccctttcgt ctcgcgcgtt 3900
tcggtgatga cggtgaaaac ctctgacaca tgcagctccc ggagacggtc acagcttgtc 3960
tgtaagcgga tgccgggagc agacaagccc gtcagggcgc gtcagcgggt gttggcgggt 4020
gtcggggctg gcttaactat gcggcatcag agcagattgt actgagagtg caccatatgc 4080
ggtgtgaaat accgcacaga tgcgtaagga gaaaataccg catcaggcgc cattcgccat 4140
tcaggctgcg caactgttgg gaagggcgat cggtgcgggc ctcttcgcta ttacgccagc 4200
tggcgaaagg gggatgtgct gcaaggcgat taagttgggt aacgccaggg ttttcccagt 4260
cacgacgttg taaaacgacg gccagtgaat tcctccgagt accccagagg agtatgtgaa 4320
aagctgccac tcgcaactac tgaagataat ttcaacgctc aagataaatc cggaggagtt 4380
tcctcgagac cccgggtcga ggctcgtgcg cggatacatc gagtattcta gactcgagcg 4440
caagccctac acgcgctacc cctgctttca acgcgtcaac ctgcacattg acggggagtt 4500
tctggttcac aagatgctag cgttcaatgc cgcgatgcgc ccatcggccg aggagctgct 4560
gtcataccca atgtttgctc aactttagga tgactaacct gtttctggga ggagacagcg 4620
tgggcgacgg tgtataaagt tggtctgctt tcaagccctg ccactgcgct acagtgccac 4680
caactgtaaa gcggtagtaa gctgcagtgg tcgactggtg gtagcatata ctaccttatt 4740
tatacgctcc gagctgtttt tcagcatgct agcacccaac gccgagcgag agtatataac 4800
tcccatcatt gcccacaagc ttatgccact tattagcgtc cgctctgccg tttgcttagt 4860
cataatatct accgccgttt acgcagcaga cgctatctgc gacacaattg gatttgcgat 4920
accgcgcatg tggatgtgta ttttaatgag atcaacctcc atgaagcgta actagggggc 4980
ctcccactga ggcactaccg gcttagcagc tgactaacac agtataaaac gtgagaagaa 5040
atcagtctca tgcgccatta gcgctaggct agttagcgtg gaggaccgga gcgctaccgc 5100
cagcagtttc atccgcctgg ttacgggttt gttaacacct accggtgttt taccgctacc 5160
ataggatccg atccatgggc ggccgcatga agaccgtgat cgccctgagt tacatcttct 5220
gcctggtgtt tgggcaggac ctccctggta aaggcaacaa cacggccacg ctgtgccttg 5280
ggcaccacgc cgtgccgaac ggcacccttg tgaaaactat taccgacgat cagatcgagg 5340

-continued

```
tgaccaacgc caccgaactg gttcagaatt ttagcatggg caaaatttgc aataacccgc   5400

accgcattct ggacggggcc aactgcacgc tgatcgattc attgctgggt gatccccact   5460

gcgatggctt tcaaaacgaa aagtgggact tgttcatcga acgcagcaag gcattcagca   5520

actgctaccc atacgacgtg cccgaataca ccagcctgcg aagcctgatc gcgagctctg   5580

ggaccctgga gttcaccaat gagaacttca attggaccgg agtgacccaa aacggtggct   5640

ccagcgcctg taaaagggga cccaataaca gcttctttag caagttgaat tggctttaca   5700

agagcggcaa tacttacccg atgttgaatg tgaccatgcc caacagtgac gactttgata   5760

aactgtacat atggggcgtg caccatccca gcacggaccg cgaacagata aacctgtacg   5820

tgcaggccag cgggaagata atcgtgagca ccaagcgcag ccagcagacc atcattccca   5880

acattggcag ccgaccgtgg gtgcgcggtc tgagctcccg catcagcata tactggacca   5940

ttgtcaagcc gggagacatc ctgatcatca actctaatgg caatcttatc gccccacgcg   6000

gctacttcaa gatgcagacc ggcaaaagca gtgtgatgag gagcgacgcc cccatcgaca   6060

cctgcaatag cgaatgcatc acccccaatg gcagcatccc caacgacaag cctttccaga   6120

acgtgaataa gatcacctac ggcgcgtgcc ccaagtacat caagcagaac accctgaagc   6180

tggccaccgg catgcgcaac atccccgagc gacagacacg ggcatttttt ggcgcaatcg   6240

cagggttcat tgagaatggc tgggagggaa tggttaacgg ctggtacggc ttccgccatc   6300

agaactctga aggaatcggc caagctgcgg atctgaagtc cacgcaagca gccatcaacc   6360

agatcaacgg caagcttaac cgcgtgattg aaaagacgaa cgagaaattc caccaaatag   6420

agaaagaatt cagcgaggtg gagggccgca tccaagacct cgagcgctac gtggaggaca   6480

ccaagatcga cctgtggagc tacaatgccg agctcctggt cgccttggaa aaccaacaca   6540

ccattgacct gaccgacagc gagatgaata aactcttcga gaagacccgg aagcaactcc   6600

gagagaacgc cgaagacatg ggtaatgggt gttttaagat ctaccacaag tgcgacaata   6660

gctgcatgga gagcatccga aacggaacct acgaccacaa cgagtaccgc gatgaggcag   6720

ttaataaccg cttccaaatc aaaagcgtgg aactgaagag tggctataag gactggatac   6780

tgtggatcag ctttgccata agctgcttcc tgctgtgcgc cgtttggttg ggtttcatca   6840

tgtgggcctg tcaaaagggc aatattcgct gtaacatctg catttgaggt ac           6892
```

<210> SEQ ID NO 24
<211> LENGTH: 4977
<212> TYPE: DNA
<213> ORGANISM: Artificial Sequence
<220> FEATURE:
<223> OTHER INFORMATION: Nucleotide sequence of transfer vector pU-1-3-p430-BGHKBGH

<400> SEQUENCE: 24

```
cctgtgcctt ctagttgcca gccatctgtt gtttgcccct cccccgtgcc ttccttgacc     60

ctggaaggtg ccactcccac tgtcctttcc taataaaatg aggaaattgc atcgcattgt    120

ctgagtaggt gtcattctat tctggggggt ggggtggggc aggacagcaa gggggaggat    180

tgggaagaca atagcaggca tgctggggat gcggtgggct ctatggatcc tagggataac    240

agggtaatcg atttattcaa caaagccacg ttgtgtctca aaatctctga tgttacattg    300

cacaagataa aaatatatca tcatgaacaa taaaactgtc tgcttacata aacagtaata    360

caaggggtgt tatgagccat attcaacggg aaacgtcttg ctcgaggccg cgattaaatt    420

ccaacatgga tgctgattta tatgggtata aatgggctcg cgataatgtc gggcaatcag    480
```

-continued

```
gtgcgacaat ctatcgattg tatgggaagc ccgatgcgcc agagttgttt ctgaaacatg    540
gcaaaggtag cgttgccaat gatgttacag atgagatggt cagactaaac tggctgacgg    600
aatttatgcc tcttccgacc atcaagcatt ttatccgtac tcctgatgat gcatggttac    660
tcaccactgc gatccccggg aaaacagcat tccaggtatt agaagaatat cctgattcag    720
gtgaaaatat tgttgatgcg ctggcagtgt tcctgcgccg gttgcattcg attcctgttt    780
gtaattgtcc ttttaacagc gatcgcgtat ttcgtctcgc tcaggcgcaa tcacgaatga    840
ataacggttt ggttgatgcg agtgattttg atgacgagcg taatggctgg cctgttgaac    900
aagtctggaa agaaatgcat aagcttttgc cattctcacc ggattcagtc gtcactcatg    960
gtgatttctc acttgataac cttatttttg acgaggggaa attaataggt tgtattgatg   1020
ttggacgagt cggaatcgca gaccgatacc aggatcttgc catcctatgg aactgcctcg   1080
gtgagttttc tccttcatta cagaaacggc tttttcaaaa atatggtatt gataatcctg   1140
atatgaataa attgcagttt catttgatgc tcgatgagtt tttctaacca tggctgtgcc   1200
ttctagttgc cagccatctg ttgtttgccc ctcccccgtg ccttccttga ccctggaagg   1260
tgccactccc actgtccttt cctaataaaa tgaggaaatt gcatcgcatt gtctgagtag   1320
gtgtcattct attctggggg gtggggtggg gcaggacagc aagggggagg attgggaaga   1380
caatagcagg catgctgggg atgcggtggg ctctatggat ccgaccctcc ccggggctaa   1440
aaagctgcgt cttcacgccc gaggcgctta ttgcccactg ggtacggggc gcgcttttat   1500
atgtgtaacg tcccaccggt gtgacgcacg tactacggtt gttctaaata gctgtccccg   1560
tgattgcctc ggctgcacac atcgcctagg tttccgccgt gcctggtgtc gagggcccac   1620
ccctgtaacc aacatcgatg gggcctgct gctccttcgc taccttagga ccgttatagt   1680
tacgtcaagc ttggcgtaat catggtcata gctgtttcct gtgtgaaatt gttatccgct   1740
cacaattcca cacaacatac gagccggaag cataaagtgt aaagcctggg gtgcctaatg   1800
agtgagctaa ctcacattaa ttgcgttgcg ctcactgccc gctttccagt cgggaaacct   1860
gtcgtgccag ctgcattaat gaatcggcca acgcgcgggg agaggcggtt tgcgtattgg   1920
gcgctcttcc gcttcctcgc tcactgactc gctgcgctcg gtcgttcggc tgcggcgagc   1980
ggtatcagct cactcaaagg cggtaatacg gttatccaca gaatcagggg ataacgcagg   2040
aaagaacatg tgagcaaaag gccagcaaaa ggccaggaac cgtaaaaagg ccgcgttgct   2100
ggcgtttttc cataggctcc gcccccctga cgagcatcac aaaaatcgac gctcaagtca   2160
gaggtggcga aacccgacag gactataaag ataccaggcg tttccccctg gaagctccct   2220
cgtgcgctct cctgttccga ccctgccgct taccggatac ctgtccgcct ttctcccttc   2280
gggaagcgtg gcgctttctc atagctcacg ctgtaggtat ctcagttcgg tgtaggtcgt   2340
tcgctccaag ctgggctgtg tgcacgaacc ccccgttcag cccgaccgct gcgccttatc   2400
cggtaactat cgtcttgagt ccaacccggt aagacacgac ttatcgccac tggcagcagc   2460
cactggtaac aggattagca gagcgaggta tgtaggcggt gctacagagt tcttgaagtg   2520
gtggcctaac tacggctaca ctagaaggac agtatttggt atctgcgctc tgctgaagcc   2580
agttaccttc ggaaaaagag ttggtagctc ttgatccggc aaacaaacca ccgctggtag   2640
cggtggtttt tttgtttgca agcagcagat tacgcgcaga aaaaaaggat ctcaagaaga   2700
tcctttgatc ttttctacgg ggtctgacgc tcagtggaac gaaaactcac gttaagggat   2760
tttggtcatg agattatcaa aaaggatctt cacctagatc cttttaaatt aaaaatgaag   2820
ttttaaatca atctaaagta tatatgagta aacttggtct gacagttacc aatgcttaat   2880
```

```
cagtgaggca cctatctcag cgatctgtct atttcgttca tccatagttg cctgactccc   2940

cgtcgtgtag ataactacga tacgggaggg cttaccatct ggccccagtg ctgcaatgat   3000

accgcgagac ccacgctcac cggctccaga tttatcagca ataaaccagc cagccggaag   3060

ggccgagcgc agaagtggtc ctgcaacttt atccgcctcc atccagtcta ttaattgttg   3120

ccgggaagct agagtaagta gttcgccagt taatagtttg cgcaacgttg ttgccattgc   3180

tacaggcatc gtggtgtcac gctcgtcgtt tggtatggct tcattcagct ccggttccca   3240

acgatcaagg cgagttacat gatcccccat gttgtgcaaa aaagcggtta gctccttcgg   3300

tcctccgatc gttgtcagaa gtaagttggc cgcagtgtta tcactcatgg ttatggcagc   3360

actgcataat tctcttactg tcatgccatc cgtaagatgc ttttctgtga ctggtgagta   3420

ctcaaccaag tcattctgag aatagtgtat gcggcgaccg agttgctctt gcccggcgtc   3480

aatacgggat aataccgcgc cacatagcag aactttaaaa gtgctcatca ttggaaaacg   3540

ttcttcgggg cgaaaactct caaggatctt accgctgttg agatccagtt cgatgtaacc   3600

cactcgtgca cccaactgat cttcagcatc ttttactttc accagcgttt ctgggtgagc   3660

aaaaacagga aggcaaaatg ccgcaaaaaa gggaataagg gcgacacgga aatgttgaat   3720

actcatactc ttcctttttc aatattattg aagcatttat cagggttatt gtctcatgag   3780

cggatacata tttgaatgta tttagaaaaa taaacaaata ggggttccgc gcacatttcc   3840

ccgaaaagtg ccacctgacg tctaagaaac cattattatc atgacattaa cctataaaaa   3900

taggcgtatc acgaggccct ttcgtctcgc gcgtttcggt gatgacggtg aaaacctctg   3960

acacatgcag ctcccggaga cggtcacagc ttgtctgtaa gcggatgccg ggagcagaca   4020

agcccgtcag ggcgcgtcag cgggtgttgg cgggtgtcgg ggctggctta actatgcggc   4080

atcagagcag attgtactga gagtgcacca tatgcggtgt gaaataccgc acagatgcgt   4140

aaggagaaaa taccgcatca ggcgccattc gccattcagg ctgcgcaact gttgggaagg   4200

gcgatcggtg cgggcctctt cgctattacg ccagctggcg aaagggggat gtgctgcaag   4260

gcgattaagt tgggtaacgc cagggttttc ccagtcacga cgttgtaaaa cgacggccag   4320

tgaattcgac gtaactataa cggtcctaag gtagcgaatt tttccattgg gcccctccct   4380

tttggctctg ggtatttagc ttccctccca cttctcattc cactttctcc acctgcacct   4440

tttccatctc ctctccaact cgccgccatg agacccgagg gagtttcgcg gggccgcgcc   4500

tcctctgtct ccatctccaa ctagtgtcga cctctatttg aggacccgcc gagtacccca   4560

caagagtatg taaaaagctg tcattctcaa ctactgagaa taatatcaaa gctaaagata   4620

aaccctgagg agtttccacg ggaaccagag tctaggctcg tgcgcggata catcgaatac   4680

gccagcctag agcgtaagcc acatacgcgc tatccttgct tccagcgcgt gaacctacac   4740

attgacgggg aatttttgat ccataaaatg ctagcgttca atgctgcgat gcgcccatcc   4800

gcagaagagt tgttgtccta cccaatgttt atgaatctgt aggatgacta acagatttgg   4860

ggtggagacg gcgtgggcga tactgtataa agttgtacta cttaccagcc cagtcagtgt   4920

gctgtagtgc caccacctgt aaagctgtga taagctgcag ttgcggccgc cgggtac      4977
```

<210> SEQ ID NO 25
<211> LENGTH: 6678
<212> TYPE: DNA
<213> ORGANISM: Artificial Sequence
<220> FEATURE:
<223> OTHER INFORMATION: Nucleotide sequence of transfer plasmid
pU1-3-p430-H1av-BGHKBGH

<400> SEQUENCE: 25

```
cctgtgcctt ctagttgcca gccatctgtt gtttgcccct cccccgtgcc ttccttgacc      60
ctggaaggtg ccactcccac tgtcctttcc taataaaatg aggaaattgc atcgcattgt     120
ctgagtaggt gtcattctat tctggggggt ggggtggggc aggacagcaa gggggaggat     180
tgggaagaca atagcaggca tgctggggat gcggtgggct ctatggatcc tagggataac     240
agggtaatcg atttattcaa caaagccacg ttgtgtctca aaatctctga tgttacattg     300
cacaagataa aaatatatca tcatgaacaa taaaactgtc tgcttacata aacagtaata     360
caaggggtgt tatgagccat attcaacggg aaacgtcttg ctcgaggccg cgattaaatt     420
ccaacatgga tgctgattta tatgggtata aatgggctcg cgataatgtc gggcaatcag     480
gtgcgacaat ctatcgattg tatgggaagc ccgatgcgcc agagttgttt ctgaaacatg     540
gcaaaggtag cgttgccaat gatgttacag atgagatggt cagactaaac tggctgacgg     600
aatttatgcc tcttccgacc atcaagcatt ttatccgtac tcctgatgat gcatggttac     660
tcaccactgc gatccccggg aaaacagcat tccaggtatt agaagaatat cctgattcag     720
gtgaaaatat tgttgatgcg ctggcagtgt tcctgcgccg gttgcattcg attcctgttt     780
gtaattgtcc ttttaacagc gatcgcgtat ttcgtctcgc tcaggcgcaa tcacgaatga     840
ataacggttt ggttgatgcg agtgattttg atgacgagcg taatggctgg cctgttgaac     900
aagtctggaa agaaatgcat aagcttttgc cattctcacc ggattcagtc gtcactcatg     960
gtgatttctc acttgataac cttatttttg acgaggggaa attaataggt tgtattgatg    1020
ttggacgagt cggaatcgca gaccgatacc aggatcttgc catcctatgg aactgcctcg    1080
gtgagttttc tccttcatta cagaaacggc tttttcaaaa atatggtatt gataatcctg    1140
atatgaataa attgcagttt catttgatgc tcgatgagtt tttctaacca tggctgtgcc    1200
ttctagttgc cagccatctg ttgtttgccc ctcccccgtg ccttccttga ccctggaagg    1260
tgccactccc actgtccttt cctaataaaa tgaggaaatt gcatcgcatt gtctgagtag    1320
gtgtcattct attctggggg gtggggtggg gcaggacagc aagggggagg attgggaaga    1380
caatagcagg catgctgggg atgcggtggg ctctatggat ccgaccctcc ccggggctaa    1440
aaagctgcgt cttcacgccc gaggcgctta ttgcccactg ggtacggggc gcgcttttat    1500
atgtgtaacg tcccaccggt gtgacgcacg tactacggtt gttctaaata gctgtccccg    1560
tgattgcctc ggctgcacac atcgcctagg tttccgccgt gcctggtgtc gagggcccac    1620
ccctgtaacc aacatcgatg gggcctgct gctccttcgc taccttagga ccgttatagt    1680
tacgtcaagc ttggcgtaat catggtcata gctgtttcct gtgtgaaatt gttatccgct    1740
cacaattcca cacaacatac gagccggaag cataaagtgt aaagcctggg gtgcctaatg    1800
agtgagctaa ctcacattaa ttgcgttgcg ctcactgccc gctttccagt cgggaaacct    1860
gtcgtgccag ctgcattaat gaatcggcca acgcgcgggg agaggcggtt tgcgtattgg    1920
gcgctcttcc gcttcctcgc tcactgactc gctgcgctcg gtcgttcggc tgcggcgagc    1980
ggtatcagct cactcaaagg cggtaatacg gttatccaca gaatcagggg ataacgcagg    2040
aaagaacatg tgagcaaaag gccagcaaaa ggccaggaac cgtaaaaagg ccgcgttgct    2100
ggcgtttttc cataggctcc gcccccctga cgagcatcac aaaaatcgac gctcaagtca    2160
gaggtggcga aacccgacag gactataaag ataccaggcg tttccccctg gaagctccct    2220
cgtgcgctct cctgttccga ccctgccgct taccggatac ctgtccgcct ttctcccttc    2280
```

-continued

```
gggaagcgtg gcgctttctc atagctcacg ctgtaggtat ctcagttcgg tgtaggtcgt   2340
tcgctccaag ctgggctgtg tgcacgaacc ccccgttcag cccgaccgct gcgccttatc   2400
cggtaactat cgtcttgagt ccaacccggt aagacacgac ttatcgccac tggcagcagc   2460
cactggtaac aggattagca gagcgaggta tgtaggcggt gctacagagt tcttgaagtg   2520
gtggcctaac tacggctaca ctagaaggac agtatttggt atctgcgctc tgctgaagcc   2580
agttaccttc ggaaaaagag ttggtagctc ttgatccggc aaacaaacca ccgctggtag   2640
cggtggtttt tttgtttgca agcagcagat tacgcgcaga aaaaaaggat ctcaagaaga   2700
tcctttgatc ttttctacgg ggtctgacgc tcagtggaac gaaaactcac gttaagggat   2760
tttggtcatg agattatcaa aaaggatctt cacctagatc cttttaaatt aaaaatgaag   2820
ttttaaatca atctaaagta tatatgagta aacttggtct gacagttacc aatgcttaat   2880
cagtgaggca cctatctcag cgatctgtct atttcgttca tccatagttg cctgactccc   2940
cgtcgtgtag ataactacga tacgggaggg cttaccatct ggccccagtg ctgcaatgat   3000
accgcgagac ccacgctcac cggctccaga tttatcagca ataaaccagc cagccggaag   3060
ggccgagcgc agaagtggtc ctgcaacttt atccgcctcc atccagtcta ttaattgttg   3120
ccgggaagct agagtaagta gttcgccagt taatagtttg cgcaacgttg ttgccattgc   3180
tacaggcatc gtggtgtcac gctcgtcgtt tggtatggct tcattcagct ccggttccca   3240
acgatcaagg cgagttacat gatcccccat gttgtgcaaa aaagcggtta gctccttcgg   3300
tcctccgatc gttgtcagaa gtaagttggc cgcagtgtta tcactcatgg ttatggcagc   3360
actgcataat tctcttactg tcatgccatc cgtaagatgc ttttctgtga ctggtgagta   3420
ctcaaccaag tcattctgag aatagtgtat gcggcgaccg agttgctctt gcccggcgtc   3480
aatacgggat aataccgcgc cacatagcag aactttaaaa gtgctcatca ttggaaaacg   3540
ttcttcgggg cgaaaactct caaggatctt accgctgttg agatccagtt cgatgtaacc   3600
cactcgtgca cccaactgat cttcagcatc ttttactttc accagcgttt ctgggtgagc   3660
aaaaacagga aggcaaaatg ccgcaaaaaa gggaataagg gcgacacgga aatgttgaat   3720
actcatactc ttcctttttc aatattattg aagcatttat cagggttatt gtctcatgag   3780
cggatacata tttgaatgta tttagaaaaa taaacaaata ggggttccgc gcacatttcc   3840
ccgaaaagtg ccacctgacg tctaagaaac cattattatc atgacattaa cctataaaaa   3900
taggcgtatc acgaggccct ttcgtctcgc gcgtttcggt gatgacggtg aaaacctctg   3960
acacatgcag ctcccggaga cggtcacagc ttgtctgtaa gcggatgccg ggagcagaca   4020
agcccgtcag ggcgcgtcag cgggtgttgg cgggtgtcgg ggctggctta actatgcggc   4080
atcagagcag attgtactga gagtgcacca tatgcggtgt gaaataccgc acagatgcgt   4140
aaggagaaaa taccgcatca ggcgccattc gccattcagg ctgcgcaact gttgggaagg   4200
gcgatcggtg cgggcctctt cgctattacg ccagctggcg aaagggggat gtgctgcaag   4260
gcgattaagt tgggtaacgc cagggttttc ccagtcacga cgttgtaaaa cgacggccag   4320
tgaattcgac gtaactataa cggtcctaag gtagcgaatt tttccattgg gcccctccct   4380
tttggctctg ggtatttagc ttccctccca cttctcattc cactttctcc acctgcacct   4440
tttccatctc ctctccaact cgccgccatg agacccgagg gagtttcgcg gggccgcgcc   4500
tcctctgtct ccatctccaa ctagtgtcga cctctatttg aggacccgcc gagtacccca   4560
caagagtatg taaaaagctg tcattctcaa ctactgagaa taatatcaaa gctaaagata   4620
aaccctgagg agtttccacg ggaaccagag tctaggctcg tgcgcggata catcgaatac   4680
```

-continued

```
gccagcctag agcgtaagcc acatacgcgc tatccttgct tccagcgcgt gaacctacac   4740

attgacgggg aatttttgat ccataaaatg ctagcgttca atgctgcgat gcgcccatcc   4800

gcagaagagt tgttgtccta cccaatgttt atgaatctgt aggatgacta acagatttgg   4860

ggtggagacg gcgtgggcga tactgtataa agttgtacta cttaccagcc cagtcagtgt   4920

gctgtagtgc caccacctgt aaagctgtga taagctgcag ttgcggccgc cgatggaggc   4980

aaaattgttc gtgctgttct gcgccttcac tgctctgaag gcagacacca tctgcgtggg   5040

ttaccacgcc aataattcca ccgacacggt ggataccatc ctggagaaga acgtgaccgt   5100

gactcattcc gtgaacctct tggagaactc acacaatggt aaattgtgca gccttaacgg   5160

caaagccccg ctgcaattgg ggaattgtaa cgtggccgga tggatactgg ggaaccccga   5220

gtgcgacctt ctcctgaccg ccaacagttg gtcctacatc attgagacga gcaacagcaa   5280

gaatggcgcc tgctatcctg gggagttcgc tgactacgag gagctgcgcg agcagttgtc   5340

tacagtcagc agcttcgaaa gattcgagat cttcccaaag gccactagct ggcccaacca   5400

cgatactacc aagggcacta cagtgagttg cagccacagc ggtgccaata gcttctaccg   5460

caacctgctg tggatcgtga agaagggtaa cagctacccc aagctgagca aatcttacac   5520

aaacaacaaa ggcaaagagg tgttggttat ctggggcgtg catcatcccc caaccgactc   5580

cgatcagcaa accctgtacc agaacaacca cacctacgtg agcgtcggta gctctaagta   5640

ttaccagcgc ttcacccccg aaatcgtcgc acgaccgaag gtgagagggc aggccgggag   5700

aatgaactac tactggaccc tgctggatca aggcgacact attaccttcg aggctaccgg   5760

caacttgatc gccccgtggc acgcgttcgc cctcaataaa ggatctaata gcggcataat   5820

gatgagtgat gcccacgtgc ataactgcac cacgaagtgc cagacccctc acggcgcact   5880

gaaaagcaat ctgccctttc agaatgtgca ccccatcacc atcggcgagt gccccaagta   5940

tgttaaaagc actcagctcc gcatggccac cggactgcgc aacatcccga gcatccaatc   6000

ccgcggactg ttcggcgcaa tcgcgggctt tatagagggc ggctggaccg gcatgatcga   6060

cggctggtac ggctaccacc atcaaaatga gcaaggttcc ggctacgccg cagaccagaa   6120

gagcacccaa atagcaatcg atggcatctc caacaaggtg aacagcgtga tcgaaaagat   6180

gaacatccag ttcacaagcg tggggaagga gttcaataac ctggaaaagc gcatcgagaa   6240

tctgaacaag aaggttgacg atgggttcct cgatgtctgg acctataacg ccgagctcct   6300

gatactgctt gagaacgagc gcaccctgga cttccacgac ttcaacgtga aaaacctgta   6360

cgaaaaggtc aagtcacagt tgcgaaacaa tgcgaaggag ataggcaacg gctgcttcga   6420

gttctatcac aagtgtgaca acgagtgcat ggagagcgtc aagaacggca cttacaacta   6480

cccgcgctac tctgaggaga gtaagctcaa ccgcgaagag attgacggcg tgaaactgga   6540

aagcgttggt gtccatcaga tcctggccat ctacagcacc gtggctagct ctctggttct   6600

gttggtgagc ctgggcgcta taagcttttg gatgtgttct aatgggagcc tgcagtgccg   6660

catctgcatc tgaggtac                                                 6678
```

<210> SEQ ID NO 26
<211> LENGTH: 566
<212> TYPE: PRT
<213> ORGANISM: Influenza A virus

<400> SEQUENCE: 26

```
Met Lys Ala Ile Leu Val Val Leu Leu Tyr Thr Phe Ala Thr Ala Asn
1               5                   10                  15
```

```
Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Lys Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430
```

```
Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Ile
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 27
<211> LENGTH: 566
<212> TYPE: PRT
<213> ORGANISM: Influenza A virus

<400> SEQUENCE: 27

Met Lys Thr Val Ile Ala Leu Ser Tyr Ile Phe Cys Leu Val Phe Gly
1               5                   10                  15

Gln Asp Leu Pro Gly Lys Gly Asn Asn Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Asn Phe Ser Met
    50                  55                  60

Gly Lys Ile Cys Asn Asn Pro His Arg Ile Leu Asp Gly Ala Asn Cys
65                  70                  75                  80

Thr Leu Ile Asp Ser Leu Leu Gly Asp Pro His Cys Asp Gly Phe Gln
                85                  90                  95

Asn Glu Lys Trp Asp Leu Phe Ile Glu Arg Ser Lys Ala Phe Ser Asn
            100                 105                 110

Cys Tyr Pro Tyr Asp Val Pro Glu Tyr Thr Ser Leu Arg Ser Leu Ile
        115                 120                 125

Ala Ser Ser Gly Thr Leu Glu Phe Thr Asn Glu Asn Phe Asn Trp Thr
    130                 135                 140

Gly Val Thr Gln Asn Gly Gly Ser Ser Ala Cys Lys Arg Gly Pro Asn
145                 150                 155                 160

Asn Ser Phe Phe Ser Lys Leu Asn Trp Leu Tyr Lys Ser Gly Asn Thr
                165                 170                 175

Tyr Pro Met Leu Asn Val Thr Met Pro Asn Ser Asp Asp Phe Asp Lys
            180                 185                 190

Leu Tyr Ile Trp Gly Val His His Pro Ser Thr Asp Arg Glu Gln Ile
        195                 200                 205

Asn Leu Tyr Val Gln Ala Ser Gly Lys Ile Ile Val Ser Thr Lys Arg
    210                 215                 220

Ser Gln Gln Thr Ile Ile Pro Asn Ile Gly Ser Arg Pro Trp Val Arg
225                 230                 235                 240
```

```
Gly Leu Ser Ser Arg Ile Ser Ile Tyr Trp Thr Ile Val Lys Pro Gly
                245                 250                 255

Asp Ile Leu Ile Ile Asn Ser Asn Gly Asn Leu Ile Ala Pro Arg Gly
            260                 265                 270

Tyr Phe Lys Met Gln Thr Gly Lys Ser Ser Val Met Arg Ser Asp Ala
        275                 280                 285

Pro Ile Asp Thr Cys Asn Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Ile Lys Gln Asn Thr Leu Lys Leu Ala Thr Gly Met
                325                 330                 335

Arg Asn Ile Pro Glu Arg Gln Thr Arg Gly Ile Phe Gly Ala Ile Ala
            340                 345                 350

Gly Phe Ile Glu Asn Gly Trp Glu Gly Met Val Asn Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Arg Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ser Cys Met Glu Ser
                485                 490                 495

Ile Arg Asn Gly Thr Tyr Asp His Asn Glu Tyr Arg Asp Glu Ala Val
            500                 505                 510

Asn Asn Arg Phe Gln Ile Lys Ser Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Ala Val Trp Leu Gly Phe Ile Met Trp Ala Cys Gln Lys Gly Asn Ile
545                 550                 555                 560

Arg Cys Asn Ile Cys Ile
                565


<210> SEQ ID NO 28
<211> LENGTH: 566
<212> TYPE: PRT
<213> ORGANISM: Influenza A virus

<400> SEQUENCE: 28

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
```

-continued

```
        35                  40                  45

Leu Leu Glu Asn Ser His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Lys Asn Gly Ala Cys Tyr Pro Gly Glu Phe
            100                 105                 110

Ala Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Asp
    130                 135                 140

Thr Thr Lys Gly Thr Thr Val Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Asp Gln Gln Thr Leu
        195                 200                 205

Tyr Gln Asn Asn His Thr Tyr Val Ser Val Gly Ser Ser Lys Tyr Tyr
    210                 215                 220

Gln Arg Phe Thr Pro Glu Ile Val Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Ser Asn Ser Gly Ile Met Met Ser Asp Ala His
        275                 280                 285

Val His Asn Cys Thr Thr Lys Cys Gln Thr Pro His Gly Ala Leu Lys
    290                 295                 300

Ser Asn Leu Pro Phe Gln Asn Val His Pro Ile Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Ser Asn Lys Val Asn Ser Val Ile
385                 390                 395                 400

Glu Lys Met Asn Ile Gln Phe Thr Ser Val Gly Lys Glu Phe Asn Asn
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Ile Leu Leu Glu Asn
        435                 440                 445

Glu Arg Thr Leu Asp Phe His Asp Phe Asn Val Lys Asn Leu Tyr Glu
    450                 455                 460
```

```
Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asn Tyr Pro Arg Tyr Ser Glu Glu Ser Lys Leu
            500                 505                 510

Asn Arg Glu Glu Ile Asp Gly Val Lys Leu Glu Ser Val Gly Val His
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 29
<211> LENGTH: 564
<212> TYPE: PRT
<213> ORGANISM: Influenza A virus

<400> SEQUENCE: 29

Met Lys Ala Lys Leu Leu Ile Leu Trp Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Val
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ala Glu Asn Gly Ile Cys Tyr Pro Gly Tyr Phe
            100                 105                 110

Ser Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Ser
    130                 135                 140

Ile Gly Ala Thr Ala Ser Cys Ser Lys Gln Gly Arg Ser Ser Phe Tyr
145                 150                 155                 160

Arg Asn Leu Leu Trp Leu Thr Glu Lys Asn Gly Ser Tyr Pro Asn Leu
                165                 170                 175

Ser Lys Ser Tyr Val Asn Asp Lys Glu Arg Glu Val Leu Val Leu Trp
            180                 185                 190

Gly Val His His Pro Ser Asn Ile Glu Asp Gln Arg Ala Ile Tyr Arg
        195                 200                 205

Lys Glu Thr Ala Tyr Val Ser Val Met Ser Ser Leu Tyr Asn Arg Arg
    210                 215                 220

Phe Thr Pro Glu Ile Ala Lys Arg Pro Lys Ile Arg Asn Gln Glu Gly
225                 230                 235                 240

Arg Ile Asn Tyr Tyr Trp Thr Leu Leu Glu Pro Lys Asp Thr Ile Ile
                245                 250                 255

Phe Glu Ala Asn Gly Asn Leu Ile Ala Pro Trp Tyr Ala Phe Ala Leu
```

-continued

```
            260                 265                 270

Ser Arg Gly Phe Glu Ser Gly Ile Ile Val Ser Asn Ala Ser Met Asp
        275                 280                 285

Glu Cys Asp Ala Lys Cys Gln Thr Pro Gln Gly Ala Ile Asn Ser Ser
    290                 295                 300

Leu Pro Phe Gln Asn Val His Pro Val Thr Ile Gly Glu Cys Pro Lys
305                 310                 315                 320

Tyr Val Lys Ser Thr Lys Leu Lys Met Ala Thr Gly Leu Arg Asn Ile
                325                 330                 335

Pro Ser Ile Gln Thr Arg Gly Leu Phe Gly Ala Ile Ala Gly Phe Ile
            340                 345                 350

Glu Gly Gly Trp Thr Gly Met Ile Asp Gly Trp Tyr Gly Tyr His His
        355                 360                 365

Gln Asn Glu Gln Gly Ser Gly Tyr Ala Ala Asp Gln Lys Ser Thr Gln
    370                 375                 380

Asn Ala Ile Asn Gly Ile Thr Asn Lys Val Asn Ser Val Ile Asp Lys
385                 390                 395                 400

Met Asn Thr Gln Phe Thr Ala Val Gly Lys Glu Phe Asn Lys Leu Glu
                405                 410                 415

Lys Arg Met Glu Asn Leu Asn Lys Lys Val Asp Asp Gly Phe Leu Asp
            420                 425                 430

Ile Trp Thr Tyr Asn Ala Glu Leu Leu Val Leu Leu Glu Asn Glu Arg
        435                 440                 445

Thr Leu Asp Phe His Asp Ser Asn Val Lys Ser Leu Tyr Glu Lys Val
    450                 455                 460

Lys Gly Gln Leu Lys Asn Asn Ala Lys Glu Ile Gly Asn Gly Cys Phe
465                 470                 475                 480

Glu Phe Tyr His Lys Cys Asn Asn Glu Cys Met Asp Ser Val Lys Asn
                485                 490                 495

Gly Thr Tyr Asp Tyr Pro Arg Tyr Ser Glu Glu Ser Lys Leu Asn Arg
            500                 505                 510

Glu Lys Ile Asp Gly Val Glu Leu Lys Ser Met Gly Val Tyr Gln Ile
        515                 520                 525

Leu Ala Ile Tyr Ser Thr Val Ala Ser Ser Leu Val Leu Leu Val Ser
    530                 535                 540

Leu Gly Ala Thr Ser Phe Trp Met Cys Ser Asn Gly Ser Leu Gln Cys
545                 550                 555                 560

Arg Ile Cys Ile
```

SWINE INFLUENZA VACCINE

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

The present invention relates to the field of (vector) vaccines, and especially to insertion sites and promoters suitable to express target antigens from such vector vaccines. Further, the present invention relates to Swine influenza A virus vaccines.

B. Background and Description of the Related Art

EHV Vector System

The horse pathogen Equid Alphaherpesvirus 1 (Equine abortion virus, EHV-1) belongs to the genus *Varicellovirus* in the subfamily Alphaherpesvirinae in the family Herpesviridae in the order Herpesvirales. It is a large, enveloped virus with a double-stranded DNA genome of approximately 150,000 base pairs. Other important members of the subgenus *Varicellovirus* are the Human Herpesvirus 3 (Varicella Zoster Virus), Suid Herpesvirus 1 (Pseudorabies virus), Bovine Herpesvirus 1 (Infectious Bronchitis Virus), and Equid Herpes Virus 4 (Equine Rhinopneumitis Virus, EHV-4) Virus Taxonomy: 2015 Release EC 47, London, UK, July 2015; Email ratification 2016.

EHV-1 and EHV-4 are endemic and affecting horses throughout the world. While EHV-4 causes a mostly mild infection of the upper respiratory tract, EHV-1 can cause systemic infection with a range of diseases from respiratory symptoms to abortion and lethal myeloencephalopathy depending on the strain and the immunological status of the host. Two licensed modified live vaccines (MLV) against EHV-1 are currently available in the USA and Europe, respectively, RHINOMUNEO™ (Boehringer Ingelheim) and PREVACCINOLO™ (MSD). Both contain the classically attenuated EHV-1 RacH strain, which was passaged 256 times in porcine epithelial cells for attenuation (Ma et al. 2013). The mechanism of attenuation has been investigated on the molecular level. Osterrieder et al. (1996) showed that RacH lacks the two genomic copies of orf67 and that restoration of one copy was sufficient to restore virulence. In addition, RacH carries a 1283 bp deletion removing more than 90% of the coding sequence of orf1 which encodes an immunosuppressive viral protein. Other mutations might also influence attenuation, but have not been investigated in detail, so far. All this makes RacH a very safe vaccine strain as a reversion to virulence by passaging in vaccinated animals is highly unlikely, if possible at all.

An *E. coli* bacterial artificial chromosome (BAC) harboring the entire genome of the Equid Herpes Virus 1 (EHV-1) vaccine strain RacH (pRacH-SE) is known as a platform for vector vaccine development. It has been shown that EHV-1 RacH-based vector vaccines are able to elicit immunity in several mammalian species including pigs, cattle, and dogs (Rosas et al. 2007, Rosas et al. 2008, Trapp et al. 2005, Said et al. 2013). Genes coding for antigenic proteins of pathogens can be expressed by recombinant EHV-1 RacH. The EHV-1-RacH genome is manipulated in its BAC form in *E. coli* and tailored to express additional proteins usually by inserting transgene expression cassettes (Tischer et al., 2010). Upon transfection of pRacH-SE DNA in cultured permissive cells, EHV-1 replication is initiated by cellular transcription factors. Activity of the viral DNA polymerase leads to deletion of all BAC-vector related sequences and restoration of the EHV-1 RacH genome to its original state. Infectious virus is generated which is indistinguishable from RacH.

When pRacH-SE is manipulated in *E. coli* e.g. by insertion of transgene expression cassettes, virus reconstituted after transfection in permissive cells will carry the modification and will express the additional gene. The recombinant EHV-1 RacH can be used as a vector vaccine.

Promoter for the EHV Vector System

However, the amount of transgenic protein expressed without an additional exogenic promoter is usually relatively low. Thus, there is an unmet need for additional promoters that can be used to express transgenic protein from such a vector, especially the recombinant EHV-1 RacH.

Using the Human cytomegalovirus immediate-early gene 1 promoter-enhancer (Boshart et al. 1985), transgenes have been reported to be efficiently expressed from the orf1/3 insertion site. In such studies the bovine growth hormone polyadenylation signal (BGH) was used to stabilize the transcripts for better expression (Ma et al. 2012; Said et al. 2013). Although there is no evidence that HCMV can induce tumors in humans, a theoretical risk cannot be excluded. Before the HCMV-IE enhancer was described (Boshart et al. 1985) the majority of strong enhancers were discovered in the genomes of known oncogenic viruses like Simian Virus 40, polyoma viruses or Moloney murine sarcoma virus. While the extremely strong and non-tissue specific HCMV and MCMV (Mouse cytomegalovirus) IE promoters-enhancers are very well suited for a variety of research activities, they might not represent the first choice of promoter for transgenic vector vaccines in general. In particular the risk of accidental exposure of persons vaccinating animals could be viewed by the regulatory authorities as a hurdle for licensing a vaccine.

Insertion Site for the EHV Vector System

Wild-type EHV-1 strains possess three open reading frames (orf) called orf1, orf 2 and orf3 at one end of the long unique segment of their genome (sequence coordinates 1298-3614; FIG. 1*a*). Orf1 and orf3 are serially arranged on one strand of the DNA while orf 2 is encoded by the complementary strand. The vaccine strain RacH has a 1283 bp deletion in that region affecting orfs 1 and 2 indicating that these genes are non-essential for viral replication. For this reason the site serves as a transgene insertion site. This insertion site is called ORF1/3.

However, the size and number of transgenes that may be inserted into the ORF1/3 insertion site is usually limited. Thus, in order to augment the capabilities of the EHV-1 vector there is an unmet need for new and alternative ways to insert and express transgenes from the EHV-1 vector, especially the recombinant EHV-1 RacH vector.

Swine Influenza A Virus (SIAV)

Swine influenza is an acute respiratory viral disease caused by influenza A virus (IAV) of the Orthomyxovirus family that decreases health and welfare of pigs. Clinical signs of influenza in pigs can display a range of severity, but often occur as mild respiratory disease with high morbidity and rapid recovery, with rare fatal cases. However, the disease has substantial economic burden as it results in weight loss, reduced weight gain and, in some cases, reproductive failure in sows due to high fever. SIAV is one of the most important respiratory pathogens of swine and its high prevalence in swine herds worldwide directly correlates to the economic impact of the disease. In Europe there are currently four major Influenza A virus subtypes circulating in farmed pigs and causing economic losses (Brown, 2000). H1N1 ("avian" subtype) and H3N2 swine influenza viruses have been enzootic in major swine producing countries since the 1980s. H1N2 viruses have been introduced in European swine about twenty years ago (Brown et al., 1995) and the H1N1 "pandemic" subtype (H1pdmN1) has been introduced into swine populations by transmission from humans to pigs in the course of the 2009 human H1N1 pandemic and has continuously spread globally in swine populations with an estimated average European prevalence of 8% among all swine Influenza virus infections (Watson et al., 2015). In addition swine Influenza also has implications for human health since IVA is well known for its zoonosis potential (Thacker&Janke 2008).

The four most prevalent Influenza A strains within Europe are H1N2, H3N2 and H1N1 (H1N1 avian and H1N1 pandemic) subtypes. Thus, there is a need for vaccines being highly efficacious against H1N2, H3N2 and H1N1 (H1N1 avian and H1N1 pandemic) subtypes and, thus, providing very broad protection against these Swine IAV field strains.

Further, it is advantageous to have a multivalent vaccine as multivalent vaccines in general are more cost-effective and are more time-effective than monovalent vaccines.

However, in general vaccine efficacy may be affected by interference effects such as viral interference of distinct vaccine strains and/or virucidal effects in one of the vaccine components. Thus, there is a need for swine IAV combination vaccines that are highly efficacious and are not affected by the above mentioned interferences.

Furthermore, the broad and multivalent coverage of circulating Swine IAV strains should also effectively prevent the vaccine-associated enhancement of respiratory disease (VAERD) after field virus infection of vaccinated animals that can be observed if vaccine strains/antigens and field viruses are only distantly related to each other (Rajao et al. 2016).

The EHV-vector based vaccine as described herein by not being a modified live vaccine (MLV) provides ultimate safety with regard to Swine IAV since no live IAVs are generated or given to animals, thus preventing potential reversion to virulence of the vaccine strain(s) and genetic recombination or reassortment with field strains from swine or humans. Moreover, in contrast to killed vaccines (current standard), a vector vaccine is expected to not only induce Swine IAV neutralizing antibodies but to also strongly stimulate the cellular immunity against Swine IAV by both the MHC class I and II pathways. Thus, there is a need for vector based SIAV vaccines.

Moreover, both modified live vaccines and inactivated vaccines lack the inherent feature for the diagnostic differentiation of infected from vaccinated animals (DIVA). Thus, there is a need for SIAV DIVA vaccines. DIVA can be achieved by detecting antibodies against Swine IAV proteins such as NP (nucleoprotein) or NA (neuraminidase) in animals that were infected by Swine IAV field strains. In contrast, animals only vaccinated with the vaccine as described herein (and not infected with the wildtype virus or MLV and not vaccinated with an inactivated vaccine) only expresses Swine IAV HA protein(s) and in such vaccinated animals proteins such as NP or NA and thus, also antibodies against NP or NA, cannot be detected.

Inactivated (killed) vaccines can be applied to mother sows before farrowing to confer protection of piglets against Swine IAV by maternally derived immunity (sow vaccine). In addition, inactivated vaccines can be applied directly to piglets (piglet vaccine). However, when applied as piglet vaccine, inactivated vaccines cannot overcome maternally derived immunity against Swine IAV in young piglets. Therefore, Swine IAV vaccination in piglets using inactivated vaccines is applied at time points starting at an age of about 8 weeks and inducing an onset of immunity from about 12 weeks of life or later, thus leaving an immunological gap in which piglets might not be protected by maternally derived immunity against Swine IAV anymore and protection against Swine IAV from vaccination of piglets is not achieved yet, thus leaving such animals susceptible for Swine IAV infection during this time period. Unlike as for killed vaccines, the vaccine described herein allows vaccination of piglets with levels of maternally derived anti-Swine IAV antibodies and still provides protection against later Swine IAV infection. Thus, there is a need for Swine IAV vaccines being highly efficacious and administrable early in age even in the presence of maternally derived antibodies.

SUMMARY OF THE INVENTION

In order to avoid any such obstacles the present invention provides new insertion sites, new promoter sequences and SIAV vaccines.

Thus, the solution to the above described technical problem is achieved by the description and the embodiments characterized in the claims and the invention in its different aspects is implemented according to the claims.

In order to augment the capabilities of the EHV vector, the present invention provides new and alternative ways to insert and express transgenes from the EHV vector backbone.

The present invention relates to EHV vectors having new insertion sites within ORF70 as defined herein.

The present invention provides an EHV vector comprising (i) at least one exogenous antigen encoding sequence relating to a pathogen infecting food producing animals; (ii) said exogenous antigen encoding sequence is inserted into ORF70; (iii) said exogenous antigen encoding sequence is operably linked to a promoter sequence.

The present invention concerns a new, alternative insertion site ORF70 that can be used to insert exogenous antigen encoding sequences and express protein from an EHV vector, especially the recombinant EHV-1 RacH.

The novel "ORF70 insertion site" in the EHV-1 vector is characterized by a partial deletion, truncation, substitution, modification or the like in relation to ORF70. A deletion of the complete ORF70 would be expected to be disadvantageous for viral replication and thus vaccine manufacturing and efficacy because complete deletion of ORF70 would affect the promoter of ORF71 encoding for gpII. The novel ORF70 insertion site and/or the insertion (of an expression cassette) into ORF70 is functionally defined in such a way that the ORF71 remains functional or intact.

In a specific aspect, the ORF70 insertion site encompasses a deletion of an approximately 801 bp portion within ORF70 for RacH (SEQ ID NO.: 20) or a 70%, 80%, 85%, 90%, 95%, 99% homologous sequence thereof. The deleted portion in the RacH genome sequence is shown as SEQ ID NO.:

20 (no nucleotide numbers available because complete RacH genome sequence not known). In another specific aspect, the ORF70 insertion site encompasses a theoretical 801 bp deletion within ORF70 for the wild-type EHV-1 strain ab4 (Genbank accession number AY665713.1). The deleted portion is located in the wild-type ab4 (Genbank accession number AY665713.1) genome sequence between nucleotides 127681 and 128482 (SEQ ID NO.: 19).

In the present invention "flanking regions" direct the recombination of the expression cassette comprising the exogenous antigen encoding sequence into the EHV-1 genome. These flanking regions are naturally present in EHV-1. The Up70 flanking region (417 bp, SEQ ID NO.: 13) and the Up71 flanking region (431 bp, SEQ ID NO.: 14) are selected for classical homologous recombination for all transfer vectors/plasmids used for the orf70 site. In the wild-type EHV-1 strain ab4 (Genbank accession number AY665713.1) the corresponding sequences are located at nucleotides 127264-127680 (flanking region up orf70, SEQ ID NO.: 15) and 128483-128913 (flanking region up orf71 , SEQ ID NO.: 16). For the RED recombination the flanking regions are truncated due to a XbaI restriction digest. These truncated flanking regions are identical to the 3' 283 bp of the 417 bp "classical" flanking region (Up70 flanking region, SEQ ID NO.: 13) and the 5' 144 bp of the 431 bp "classical" flanking region (Up71 flanking region, SEQ ID NO.: 14), which are described above. These truncated flanking regions are named Up70 flanking region (283 bp), included as SEQ ID NO.: 17 and Up71 flanking region (144 bp) included as SEQ ID NO.: 18. These various flanking regions define the same ORF70 insertion site. The flanking regions are used in pairs always one "left" flanking region such as SEQ ID NOs.: 13, 15, 17 and one "right" flanking region such as SEQ ID NOs.: 14, 16, 18.

Further, the present invention provides new regulatory nucleic acid sequences/promoter sequences for transgene expression, immunogenic compositions, vaccines, and related methods that overcome deficiencies in the art.

Thus, the present invention provides an EHV vector comprising (i) at least one exogenous antigen encoding sequence relating to a pathogen infecting food producing animals; (ii) said exogenous antigen encoding sequence is inserted into an insertion site; (iii) said exogenous antigen encoding sequence is operably linked to a promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

Thus, the present invention relates to EHV vectors having two new promoters: 4pgG600 and 4pMCP600, and derivatives of shorter lengths thereof, which are shown to be functional after transient transfection in cell cultures or in the background of rEHV1-RacH replication in cell cultures. The new promoters p430 and p455 are shown to be functional in the background of rEHV1-RacH replication in cell cultures, and also in animals (pigs and mice). Activity levels of the two new promoters during the viral replication cycle appear to be very similar as deduced from in vitro promoter kinetic experiments.

These properties allow creation of recombinant vector vaccines based on EHV-1 RacH expressing two different antigens in parallel with similar efficiency. If a vaccine target consists of two different pathogens application of the two new promoters in two insertion sites combined with two polyadenylation sequences can reduce cost of goods significantly and represents a clear advantage over a vector expressing only one antigenic component.

The present invention further concerns an EHV-1 vector expressing two different transgenes from one vector backbone without coupling two transgenes by RNA-virus-derived functions (2a peptides, IRES sites) under control of one promoter.

Further, the present invention provides an EHV vector comprising (i) at least two exogenous antigen encoding sequences relating to a pathogen infecting food producing animals; (ii) said exogenous antigen encoding sequences are inserted into insertion sites; (iii) said exogenous antigen encoding sequences are operably linked to promoter sequences.

(i)

Furthermore, the present invention provides immunogenic compositions and DIVA vaccines comprising the EHV vector as described above.

These properties allow creation of recombinant vector vaccines based on EHV-1 RacH expressing different antigens in parallel with similar efficiency. If a vaccine target consists of two different pathogens, application of the two new promoters in two insertion sites combined with two polyadenylation sequences can reduce cost of goods significantly and represents a clear advantage over a vector expressing only one antigenic component.

Further, the present invention provides SIAV vaccines. The present invention relates further to specific hemagglutinin sequences such as to SEQ ID NO:26, SEQ ID NO:27, SEQ ID NO:28 and SEQ ID NO:29 and homolog sequences thereof. Furthermore, the present invention provides monovalent and multivalent SIAV vaccines being safe and highly effective.

Further, the vector based SIAV vaccine of the present invention can be used for differentiating food producing animals infected with Swine Influenza A virus from food producing animals vaccinated with the immunogenic composition or the DIVA vaccine as described herein.

Moreover, the present invention relates to the use of the immunogenic compositions and DIVA vaccines comprising the EHV vectors as described herein. The present invention refers to a method for immunizing food producing animals, the treatment or prophylaxis of clinical signs caused by swine IAV in food producing animal, a method of reducing the virus titers in lungs in food producing animal and a method of vaccinating a food producing animal of need having anti-Swine Influenza A virus antibodies.

DETAILED DESCRIPTION OF THE INVENTION

The present invention solves the problems inherent in the prior art and provides a distinct advance in the state of the art. Generally, the present invention provides an EHV vector comprising: (i) at least one exogenous antigen encoding sequence relating to a pathogen infecting food producing animals; (ii) said exogenous antigen encoding sequence is inserted into ORF70; (iii) said exogenous antigen encoding sequence is operably linked to a promoter sequence.

Further, the present invention provides an immunogenic composition comprising an EHV vector as described herein and optionally a pharmaceutical carrier.

Thus, the present invention provides an immunogenic composition comprising an EHV vector comprising (i) at least one exogenous antigen encoding sequence relating to a pathogen infecting food producing animals; (ii) said exogenous antigen encoding sequence is inserted into ORF70;

(iii) said exogenous antigen encoding sequence is operably linked to a promoter sequence.

Advantageously, the experimental data provided by the present invention disclose that a new insertion site within the EHV vector has been provided that can be used for inserting and expressing antigens. Further, the provision of the new insertion site now allows the insertion and expression of antigens from different insertion sites and the expression of more than one antigen, respectively. Furthermore, the experimental data show that EHV vectors with the new insertion site can be used for providing immunogenic compositions from one or two sites and for DIVA vaccines, respectively.

Further, the present invention provides an EHV vector comprising (i) at least one exogenous antigen encoding sequence relating to a pathogen infecting food producing animals; (ii) said exogenous antigen encoding sequence is inserted into an insertion site; (iii) said exogenous antigen encoding sequence is operably linked to a promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

Further, the present invention provides an immunogenic composition comprising an EHV vector as described herein and optionally a pharmaceutical carrier.

Thus, the present invention provides an immunogenic composition comprising an EHV vector comprising (i) at least one exogenous antigen encoding sequence relating to a pathogen infecting food producing animals; (ii) said exogenous antigen encoding sequence is inserted into an insertion site; (iii) said exogenous antigen encoding sequence is operably linked to a promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

Advantageously, the experimental data provided by the present invention disclose that new promoter sequences have been provided that can be used for expressing antigens. Further, the provision of the new promoter sequences allow the expression of antigens from different insertion sites of a vector system such as the EHV vector system and the expression of more than one antigen, respectively. Furthermore, the experimental data show that the promoter sequences can be used for expressing antigens in vector systems such as the EHV vector system for providing immunogenic compositions from one or two sites and for DIVA vaccines, respectively.

Further, the present invention provides an EHV vector comprising (i) at least two exogenous antigen encoding sequences relating to a pathogen infecting food producing animals; (ii) said exogenous antigen encoding sequences are inserted into insertion sites; (iii) said exogenous antigen encoding sequences are operably linked to promoter sequences.

Further, the present invention provides an immunogenic composition comprising an EHV vector as described herein and optionally a pharmaceutical carrier.

Thus, the present invention provides an immunogenic composition comprising an EHV vector comprising: (i) at least two exogenous antigen encoding sequences relating to a pathogen infecting food producing animals; (ii) said exogenous antigen encoding sequences are inserted into insertion sites; (iii) said exogenous antigen encoding sequences are operably linked to promoter sequences.

Further, the present invention provides an immunogenic composition comprising two or more EHV vectors as described herein. Preferably, the immunogenic composition comprises two, three or four EHV vectors.

In one aspect of the present invention the immunogenic composition comprises two EHV vectors.

In one aspect of the present invention the two or more EHV vectors comprise different exogenous antigen encoding sequences. Preferably, the two or more EHV vectors comprise different exogenous antigen encoding sequence relating to the Swine influenza A virus. More preferably, the two or more EHV vectors comprise different hemagglutinin encoding sequences.

Further, the present invention provides a DIVA vaccine comprising one or more EHV vectors as described herein.

In one aspect of the present invention the EHV vector is recombinant.

In one aspect of the present invention the EHV vector is RacH or RacH SE.

In one aspect of the present invention the EHV vector is selected from the group consisting of EHV-1, EHV-3, EHV-4, EHV-8 and EHV-9.

In one aspect of the present invention the EHV vector is EHV-1.

In one aspect of the present invention the food producing animals is swine.

In one aspect of the present invention the pathogen infecting food producing animals is an Influenza Virus, preferably Swine influenza A virus.

In one aspect of the present invention the exogenous antigen encoding sequence is a hemagglutinin encoding sequence.

In one aspect of the present invention the exogenous antigen encoding sequence is a hemagglutinin encoding sequence and the hemagglutinin influenza subtype is selected from the group consisting of H1, H2, H3, H4, H5, H6, H7, H8, H9, H10, H11, H12, H13, H14, H15, H16, H17 and H18.

In one aspect of the present invention the exogenous antigen encoding sequence is a hemagglutinin encoding sequence and the hemagglutinin influenza subtype is H1 and/or H3.

In one aspect of the present invention the exogenous antigen encoding sequence is a hemagglutinin encoding sequence and the hemagglutinin influenza A antigens have a swine origin.

In one aspect of the present invention the EHV vector comprises at least two hemagglutinin influenza antigen encoding sequences.

In one aspect of the present invention the EHV vector comprises at least four hemagglutinin influenza antigen encoding sequences.

In one aspect of the present invention the EHV vector comprises four hemagglutinin influenza antigen encoding sequences.

In one aspect of the present invention the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001(H3N2), A/swine/Gent/132/2005(H1N1), A/swine/Italy/4675/2003(H1N2), A/swine/Italy/259543/2003 (H1N2), A/swine/Denmark/13772-1/2003(H1N1), A/swine/England/MD0040352R/2009(H1N1), A/swine/Hungary/13509/2007(H3N2), A/swine/Italy/13962/95(H3N2), A/swine/Cotes d'Armor/1121/00(H1N1), A/Swine/Colorado/1/77, A/Swine/Colorado/23619/99, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/985 A/Swine/Wisconsin/458/98, A/Swine/Wisconsin/464/98 and A/Swine/Wisconsin/14094/99.

In one aspect of the present invention the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001(H3N2), A/swine/Gent/132/2005(H1N1) and A/swine/Italy/4675/2003(H1N2).

In one aspect of the present invention the exogenous antigen encoding sequence is a hemagglutinin encoding sequence and the hemagglutinin influenza antigen encoding sequence encodes an amino acid sequence selected from a group consisting of SEQ ID NO:26, SEQ ID NO:27, SEQ ID NO:28 and SEQ ID NO:29.

In one aspect of the present invention the exogenous antigen encoding sequence is a hemagglutinin encoding sequence and the hemagglutinin influenza antigen encoding sequence comprises a nucleic acid sequence encoding an amino acid sequence with at least 70% identity to the amino acid sequence as set forth in SEQ ID NO:26, SEQ ID NO:27, SEQ ID NO:28 and SEQ ID NO:29.

In one aspect of the present invention the exogenous antigen encoding sequence is a hemagglutinin encoding sequence and the hemagglutinin influenza antigen encoding sequence comprises a nucleic acid sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:26, SEQ ID NO:27, SEQ ID NO:28 and SEQ ID NO:29.

In one aspect of the present invention the exogenous antigen encoding sequence is an Influenza A virus N (neuraminidase) encoding sequence and the N subtype is selected from the group consisting of N1, N2, N3, N4, N5, N6, N7, N8, N9 and N10.

In one aspect of the present invention the EHV vector, the immunogenic composition or the DIVA vaccine does not comprise N (neuraminidase) influenza antigen encoding sequences.

In one aspect of the present invention the EHV vector, the immunogenic composition or the DIVA vaccine does not comprise NP (nucleoprotein) influenza antigen encoding sequences.

In one aspect of the present invention the EHV vector comprises additional regulatory sequences such as a termination signal or polyadenylation sequence.

Insertion Site:

In one aspect of the present invention said insertion site is ORF1/3.

In one aspect of the present invention said insertion site is ORF70.

In one aspect of the present invention a first exogenous antigen encoding sequence relating to a pathogen infecting food producing animals is inserted into ORF70.

In one aspect of the present invention a second exogenous antigen encoding sequence relating to a pathogen infecting food producing animals is inserted into ORF1/3.

In one aspect of the present invention the insertion into ORF70 is characterized by a partial deletion, truncation, substitution, modification or the like in ORF70, whereby ORF71 remains functional.

In one aspect of the present invention the insertion into ORF70 is characterized by the deletion of an approximately 801 bp portion within ORF70 for RacH (SEQ ID NO: 20) or a 70%, 80%, 85%, 90%, 95%, 99% homologous and/or identical sequence thereof.

In another specific aspect of the vector of the present invention the insertion into ORF70 is characterized by the deletion of an approximately 801 bp portion within ORF70 for RacH (SEQ ID NO.: 20) or a 70%, 80%, 85%, 90%, 91%, 92%, 93%, 94%, 95%, 96%, 97%, 98%, 99% homologous and/or identical sequence deletion thereof in any other strain.

In a further specific aspect of the vector of the present invention the insertion into ORF70 is characterized by the deletion of an approximately 801 bp deletion within ORF70 for the wild-type EHV-1 strain ab4 (Genbank accession number AY665713.1), whereby the deleted portion in the wild-type ab4 genome sequence is located between nucleotides 127681 and 128482 (SEQ ID NO.: 19) or a 70%, 80%, 85%, 90%, 91%, 92%, 93%, 94%, 95%, 96%, 97%, 98%, 99% homologous and/or identical sequence thereof.

In a further specific aspect of the vector of the present invention the insertion into ORF70 is characterized by the deletion of an approximately 801 bp deletion within ORF70 for the wild-type EHV-1 strain ab4 (Genbank accession number AY665713.1), whereby the deleted portion in the wild-type ab4 genome sequence is located between nucleotides 127681 and 128482 (SEQ ID NO.: 19) or a 70%, 80%, 85%, 90%, 91%, 92%, 93%, 94%, 95%, 96%, 97%, 98%, 99% homologous and/or identical sequence deletion thereof in any other strain.

In one aspect of the present invention the EHV-1 vector comprises at least one flanking regions selected from the group consisting of: SEQ ID NO: 13, SEQ ID NO: 14, SEQ ID NO: 15, SEQ ID NO: 16, SEQ ID NO: 17, and SEQ ID NO: 18 and a 70%, 80%, 85%, 90%, 95%, 96%, 97%, 98%, 99% homologous and/or identical sequence of any one of these sequences.

In one aspect of the present invention the EHV-1 vector comprises (i) at least one left ORF70 flanking region selected from the group consisting of: SEQ ID NO.: 13, SEQ ID NO: 15, and SEQ ID NO: 17, and (ii) at least one right ORF70 flanking region selected from the group consisting of: SEQ ID NO: 14, SEQ ID NO: 16, and SEQ ID NO: 18.

Promoter:

In one aspect of the present invention the promoter sequence is selected from the group consisting of: SV40 large T, HCMV and MCMV immediate early gene 1, human elongation factor alpha promoter, baculovirus polyhedrin promoter, a functional fragment of 4pgG600 (SEQ ID NO:1), preferably said functional fragment is p430 (SEQ ID NO:3), a functional fragment of the complementary nucleotide sequence of 4pgG600 (SEQ ID NO:1), a functional fragment of 4pMCP600 (SEQ ID NO:2), preferably said functional fragment is p455 (SEQ ID NO:4), a functional fragment of the complementary nucleotide sequence of 4pMCP600 (SEQ ID NO: 2).

In one aspect of the present invention the promoter sequence comprises 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

In one aspect of the present invention the functional fragment or derivative of the promoter sequence has a homology of 80%, 85%, preferably 90%, 91%, 92%, 93%, 94%, more preferably 95%, 96%, 97%, 98%, 99%, 99.9%.

In one aspect of the present invention the functional fragment or derivative of the promoter sequence has a length of 550 nucleotides, preferably 500, 490, 480, 470, 460, 455, 450, 445, 440, 435, 434, 433, 432, 431, 430 nucleotides, most preferably 455 or 430 nucleotides.

In one aspect of the present invention the functional fragment of the promoter sequence is a truncation of 4pgG600 (SEQ ID NO:1) or the complementary nucleotide sequence thereof, preferably the sequence identity is (at least) 72% over entire length (or higher).

In one aspect of the present invention the functional fragment of the promoter sequence of 4pgG600 (SEQ ID NO:1) is the fragment designated 430p430 (SEQ ID NO:3). In another aspect the sequence identity is (at least) 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

In one aspect of the present invention the functional fragment of the promoter sequence is a truncation of 4pMCP600 (SEQ ID NO:2) or the complementary nucleotide sequence thereof, preferably the sequence identity is (at least) 78% over entire length (or higher).

In one aspect of the present invention the functional fragment of the promoter sequence of 4pMCP600 (SEQ ID NO:2) is the fragment designated p455 (SEQ ID NO:4). In another aspect the sequence identity is (at least) 70%, 80%, 85%, preferably 90%, 91%, 92%, 93%, 94%, more preferably 95%, 96%, 97%, 98%, 99%, 99.1%, 99.2%, 99.3%, 99.4%, 99.5%, 99.6%, 99.7%, 99.8%, 99.9%.

In one aspect of the present invention the EHV vector comprises one or more further regulatory sequences such as a termination signal, a polyadenylation signal or a regulatory element like IRES and/or 2a peptide.

Specific Combinations of Promoters and Antigens:

In one aspect of the present invention the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28.

In one aspect of the present invention the functional fragment of the promoter sequence 4pgG600 (SEQ ID NO:1) is the fragment designated p430 (SEQ ID NO:3).

In one aspect of the present invention the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27.

In one aspect of the present invention the functional fragment of the promoter sequence 4pMCP600 (SEQ ID NO:2) is the fragment designated 455p455 (SEQ ID NO:4).

In one aspect of the present invention the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28 and, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27.

In one aspect of the present invention the functional fragment of the promoter sequence 4pgG600 (SEQ ID NO:1) is the fragment designated p430 (SEQ ID NO:3) and, wherein the functional fragment of the promoter sequence 4pMCP600 (SEQ ID NO:2) is the fragment designated 455p455 (SEQ ID NO:4).

In one aspect of the present invention the immunogenic composition or the DIVA vaccine is bivalent.

In one aspect of the present invention the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29.

In one aspect of the present invention the functional fragment of the promoter sequence 4pgG600 (SEQ ID NO:1) is the fragment designated p430 (SEQ ID NO:3).

In one aspect of the present invention the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26.

In one aspect of the present invention the functional fragment of the promoter sequence 4pMCP600 (SEQ ID NO:2) is the fragment designated 455p455 (SEQ ID NO:4).

In one aspect of the present invention the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29, and wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26.

In one aspect of the present invention the functional fragment of the promoter sequence 4pgG600 (SEQ ID No. 1) is the fragment designated p430 (SEQ ID NO: 3) and wherein the functional fragment of the promoter sequence 4pMCP600 (SEQ ID NO: 2) is the fragment designated 455p455 (SEQ ID NO:4).

In one aspect of the present invention the immunogenic composition or the DIVA vaccine is bivalent.

In one aspect of the present invention said immunogenic composition comprises a first EHV vector comprising the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28 and, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27 and wherein said immunogenic composition comprises a second EHV vector comprising the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29, and wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26.

In one aspect of the present invention the functional fragment of the promoter sequence 4pgG600 (SEQ ID NO:1) is the fragment designated p430 (SEQ ID NO:3) and wherein the functional fragment of the promoter sequence 4pMCP600 (SEQ ID No. 2) is the fragment designated 455p455 (SEQ ID NO:4).

In one aspect of the present invention the immunogenic composition or DIVA vaccine is tetravalent.

In one aspect of the present invention said immunogenic composition or DIVA vaccine is formulated for a single-dose administration.

Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

It has furthermore been shown that one dose of the immunogenic composition of the present invention is effective after the administration of such single dose of such immunogenic composition.

In one aspect of the present invention said immunogenic composition or DIVA vaccine is administered intramuscular or intranasal.

In one aspect of the present invention the immunogenic composition or DIVA vaccine is safe for pigs within the first six weeks of age, within the first two weeks of age, within the first week of age or within the first day of age.

In one aspect of the present invention the immunogenic composition or DIVA vaccine further comprises a pharmaceutically acceptable carrier.

In one aspect of the present invention said pharmaceutically acceptable carrier is aqua ad injection, cell culture media or a resuspension buffer.

In one aspect of the present invention said resuspension buffer is phosphate buffered saline.

In one aspect of the present invention the immunogenic composition or DIVA vaccine comprises $1\times10^4$ to $1\times10^9$ tissue culture infectious doses 50 ($TCID_{50}$), preferably between $1\times10^4$ to $1\times10^8$ $TCID_{50}$, even more preferably $1\times10^4$ to $1\times10^7$ $TCID_{50}$ of the EHV vector.

In one aspect of the present invention said immunogenic composition is a vaccine.

In one aspect of the present invention said immunogenic composition or DIVA vaccine is a multivalent vaccine.

In one aspect of the present invention said immunogenic composition or DIVA vaccine is a bivalent vaccine, tetravalent vaccine, hexavalent vaccine or heptavalent vaccine.

In one aspect of the present invention said immunogenic composition or DIVA vaccine is a bivalent vaccine or tetravalent vaccine.

In one aspect of the present invention the immunogenic composition or DIVA vaccine is effective in the treatment and/or prophylaxis of clinical signs caused by Swine Influenza A virus in a food producing animal of need.

In one aspect of the present invention the immunogenic composition or DIVA vaccine protects against a homologous and/or heterologous challenge with a Swine Influenza A virus.

In one aspect of the present invention the immunogenic composition or DIVA vaccine protects against a challenge with a Swine Influenza A virus of serotypes H1 and/or H3.

Kit

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a food producing animal, especially swine. Associated with such container(s) can be a notice in the form prescribed by a governmental agency regulating the manufacture, use or sale of pharmaceuticals or biological products, which notice reflects approval by the agency of manufacture, use or sale for animal administration.

The present invention provides a kit comprising the immunogenic composition or DIVA vaccine as described herein.

In one aspect of the present invention the kit further comprises an instruction letter for the treatment and/or prophylaxis of Swine Influenza A virus.

Method of Treatment

The present invention provides a method for immunizing a food producing animal comprising administering to such food producing animal an immunogenic composition or a DIVA vaccine as described herein.

Preferably, immunization results in lessening of the incidence of the particular Swine Influenza A virus infection in a herd or in the reduction in the severity of clinical signs caused by or associated with the particular Swine Influenza A virus infection.

Further, the immunization of a food producing animal in need with the immunogenic compositions as provided herewith, results in preventing infection of a food producing animal by Swine Influenza A virus infection. Even more preferably, immunization results in an effective, long-lasting, immunological-response against Swine Influenza A virus infection. It will be understood that the said period of time will last more than 2 months, preferably more than 3 months, more preferably more than 4 months, more preferably more than 5 months, more preferably more than 6 months. It is to be understood that immunization may not be effective in all animals s immunized. However, the term requires that a significant portion of animals of a herd are effectively immunized.

Preferably, a herd of food producing animal is envisaged in this context which normally, i.e. without immunization, would develop clinical signs normally caused by or associated with a Swine Influenza A virus infection. Whether the food producing animals of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the animals of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to food producing animals that are either not immunized or immunized with an immunogenic composition that was available prior to the present invention but subsequently infected by the particular Swine Influenza A virus.

The present invention provides a method for the treatment or prophylaxis of clinical signs caused by influenza A virus in a food producing animal of need, the method comprising administering to the food producing animal a therapeutically effective amount of an immunogenic composition or a DIVA vaccine as described herein.

Preferably, the clinical signs are reduced by at least 50%, even more preferably by at least 60%, still more preferably by at least 70%, even more preferably by at least 80%, even more preferably by at least 90%, still more preferably by at least 95% most preferably by 100% in comparison to a food producing animal that is not treated (not immunized) but subsequently infected by the particular Influenza A virus.

The present invention provides a method of reducing the virus titers in lungs in a food producing animal of need, in comparison to a food producing animal of a non-immunized control group of the same species, the method comprising administering to the food producing animal a therapeutically effective amount of an immunogenic composition or DIVA vaccine as described herein. However, it has to be understood that said virus is an Influenza A virus, preferably a swine Influenza A virus.

Preferably, the virus titers in lungs is reduced by at least 50%, even more preferably by at least 60%, still more preferably by at least 70%, even more preferably by at least 80%, even more preferably by at least 90%, still more preferably by at least 95% most preferably by 100% in comparison to a food producing animal of a non-immunized control group of the same species that is subsequently infected by the particular Influenza A virus.

Advantageously, the experimental data provided by the present invention disclose safety and efficacy of the immunogenic composition provided herein when administered to pigs. In fact, pigs vaccinated with the immunogenic composition provided herein have reduced clinical signs associated with the disease compared to non-vaccinated piglets such as reduced virus lung titers after challenge virus infection.

The present invention provides a method of vaccinating a food producing animal of need having anti-Swine Influenza A virus antibodies comprising the step of administering to said food producing animal a therapeutically effective amount of an immunogenic composition or a DIVA vaccine as described herein.

However, anti-Swine Influenza A virus antibodies might be present in non-vaccinated piglets that have been developed by the piglet in response to a Swine Influenza A virus infection. Alternatively, the anti-Swine Influenza A virus antibodies in non-vaccinated piglets are maternally derived antibodies developed in response to vaccination of sows with a Swine Influenza A virus vaccine or in response to a Swine Influenza A virus infection of sows. The maternally derived antibodies are passively transferred from such sows to piglets via colostrum and milk.

Interference of maternally derived antibodies with vaccine antigen may reduce or even eliminate the immune response against live, as well as inactivated vaccines. Various degrees of interference of vaccine-induced immune responses by maternally derived antibodies have been reported for live vaccines, as well as for nonreplicating ones (i.e. inactivated or subunit vaccines).

Thus, the Swine IAV vaccine described herein can be successfully applied to piglets in the presence of maternally derived antibodies against Swine IAV and provides protection against Swine IAV infection.

Further, vaccination of sows with the Swine IAV vaccine as described herein results in immunity of the sows and transfer of maternally derived antibodies to the piglets.

Thus, the present invention provides a method of providing maternally derived immunity against Influenza A virus in a young food producing animal comprising administering to the mother of said young food producing animal a therapeutically effective amount of an immunogenic composition or DIVA vaccine as described herein while said mother is pregnant with said young food producing animal.

Because the Swine IAV vaccine described herein can be successfully applied to piglets in the presence of maternally derived antibodies said vaccine can be used for sow vaccination and subsequent vaccination of the piglets farrowed by said sow. The vaccinated sow transfers maternally derived immunity including antibodies to the piglets. However, as the Swine IAV vaccine described as herein does not interfere with maternally derived antibodies, the piglets can be vaccinated with the same vaccine early in age. Further, by vaccinating the sow with the vaccine as described herein or any other Swine IAV sow vaccine as well as the young piglets farrowed by the sow, the protection against Influenza A virus infection is increased. In the first days to weeks of life the piglet is protected by the maternally derived immunity. Further, by early vaccination of piglets, the piglets derive immunity against Influenza A virus infection and, thus, are protected without the occurrence of an immunological gap between the fading of maternally derived immunity and the onset of vaccination.

The present invention provides a method of providing increased protection against Influenza A virus infection in a young food producing animal of need, wherein a. the mother of said young food producing animal is to be vaccinated with a therapeutically effective amount of an immunogenic composition or DIVA vaccine as described herein while said mother is pregnant with said young food producing animal and/or
b. said young food producing animal is to be vaccinated with a therapeutically effective amount of said immunogenic composition or DIVA vaccine within three weeks of age.

Preferably, said immunogenic composition or DIVA vaccine is administered to a pregnant sow at least one time before farrowing, preferably after a basic immunization of one, more preferably of two vaccinations has occurred ("repeated doses"). When the immunogenic composition or DIVA vaccine is administered to the sow three times, the first basic immunization should occur between 116 and 60 days before farrowing, preferably between 116 and 58 days before farrowing, and most preferably between 116 and 56 days before farrowing. The second basic immunization should occur between 95 and 40 days before farrowing, preferably between 95 and 38 days before farrowing, and most preferably between 95 and 35 days before farrowing. The final booster administration before farrowing should occur between 10 and 20 days before farrowing, preferably between 12 and 18 days before farrowing, and most preferably 14 days before farrowing.

The immunogenic composition or DIVA vaccine is administered to piglets preferably before they reach three weeks of age. Preferably, the immunogenic composition or DIVA vaccine is administered to each of the piglets at 1 day of age to 21 days of age, more preferably, between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age.

However, the immunogenic composition can be administered to the piglets at two or more doses, with a first dose being administered prior to the administration of a second (booster) dose. Preferably, the first dose is administered within the first two weeks of age, more preferably within the first week of age and even more preferably within the first day of age. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above. Thus, said method refers to the vaccination of pregnant sows as well as the farrowed piglets.

In one aspect of the present invention the food producing animal is swine, piglet or sow.

In one aspect of the present invention the Influenza A virus is swine Influenza A virus.

In one aspect of the present invention the immunogenic composition or a DIVA vaccine is administered once.

It is understood, that a single-dose is administered only once. As shown in the Examples the immunogenic composition as provided herein has been proven to be efficacious after the administration of a single dose.

Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

In one aspect of the present invention the immunogenic composition or a DIVA vaccine is administered to the food producing animals within the first six weeks of age, within the first two weeks of age, within the first week of age or within the first day of age.

Preferably, the food producing animal to be immunized is between 1 day of age to 40 days of age, 1 day of age to 30 days of age, 1 day of age to 21 days of age, more preferably, said food producing animal to be immunized is between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age or 0 days of age.

Preferably, the food producing animal to be immunized is 1, 2, 3, 4, 5, 6, 7, 8, 9, 10, 11, 12, 13, 14, 15, 16, 17, 18, 19, 20 or 21 days of age. More preferably, said food producing animal to be immunized is 1, 2, 3, 4, 5, 6 or 7 days of age. However, it has to be understood that after vaccination of food producing animals being a few days of age, it does need several days for the immune system of the food producing animal to build up immunity against a Swine Influenza A virus infection. Therefore, preferably, the food producing animals are immunized within the first day of age.

In one aspect of the present invention the immunogenic composition or a DIVA vaccine is administered at two doses.

As shown in the Examples the immunogenic composition as provided herein has been proven to be efficacious after the administration of two doses.

However, the immunogenic composition can be administered at two or more doses, with a first dose being administered prior to the administration of a second (booster) dose. Preferably, the first dose is administered within the first two weeks of age, more preferably within the first week of age and even more preferably within the first day of age. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

In one aspect of the present invention the immunogenic composition or DIVA vaccine is administered to the food producing animal within the first week of age and a second time within the second, third or fourth week of age.

In one aspect of the present invention said immunogenic composition or DIVA vaccine is administered intramuscular or intranasal.

The immunogenic composition or DIVA vaccine is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition or DIVA vaccine may be administered by other routes as well. However, most preferred the immunogenic composition or DIVA vaccine is administered intramuscular or intranasal.

In one aspect of the present invention the food producing animal is anti-Swine Influenza A virus antibody negative.

In one aspect of the present invention the food producing animal is anti-Swine Influenza A virus antibody positive. Preferably, the anti-Swine Influenza A virus antibody titers are determined by hemagglutinin inhibition test and/or virus neutralization test and are between 1:2 and 1:2,048, between 1:2 and 1:1,024, between 1:2 and 1:512, between 1:2 and 1:256, between 1:2 and 1:128, between 1:2 and 1:64, between 1:2 and 1:32, between 1:2 and 1:16, between 1:64 and 1:2,048, between 1:64 and 1:1024, or between 1:64 and 1:512, respectively. Alternatively or in addition, the anti-Swine Influenza A virus antibody titers are determined by ELISA assays which are assessed by use of established or recommended test-specific threshold values for anti-Swine Influenza A virus antibody positive and negative samples, respectively.

It is in the general knowledge of a person skilled in the art how to measure the maternally derived anti-Swine Influenza A virus antibodies.

Preferably, the immunogenic composition or DIVA vaccine comprises $1\times10^4$ to $1\times10^9$ TCID$^{50}$, preferably between $1\times10^4$ to $1\times10^8$ TCID$^{50}$, even more preferably $1\times10^4$ to $1\times10^7$ TCID$^{50}$ of the EHV vector.

In one aspect of the present invention the immunogenic composition or DIVA vaccine comprises $1\times10^4$ to $1\times10^7$ $TCID_{50}$ of the EHV vector.

In one aspect of the present invention said method results in an improvement in an efficacy parameter selected from the group consisting of: a reduction in weight loss, a lower virus load in lungs, a reduction in lung lesions, a reduced and/or shortened shedding of virus, a reduced rectal temperature, reduced clinical symptoms (in particular respiratory symptoms), increased induction of (neutralizing) anti-Swine Influenza A virus antibodies, increased stimulation of T-cells against Swine Influenza A virus, increased stimulation of B-cells against Swine Influenza A virus, and a reduction of proinflammatory cytokines, e.g. IL1β, in lungs, or combinations thereof, in comparison to a food producing animal of a non-immunized control group of the same species.

In one aspect of the present invention the treatment or prophylaxis results in shortening of the virus load phase as compared to a food producing animal of a non-treated control group of the same species.

Preferably, the treatment or prophylaxis results in shortening of the virus load phase by at least 50%, even more preferably by at least 60%, still more preferably by at least 70%, even more preferably by at least 80%, even more preferably by at least 90%, still more preferably by at least 95% most preferably by 100% as compared to a food producing animal of a non-treated control group of the same species subsequently infected by the particular Swine Influenza A virus.

Preferably, the treatment or prophylaxis results in a reduction of the shedding of the Swine Influenza A virus from day 5 after challenge or infection, more preferably from day 4 after challenge or infection, more preferably from day 3 after challenge or infection and most preferably from day 1 or 2 after challenge or infection with the Swine Influenza A virus as compared to a food producing animal of a non-immunized control group of the same species.

In one aspect of the present invention the treatment or prophylaxis results in a reduction of the shedding of the Influenza A virus from day 1 after challenge (infection).

In one aspect of the present invention the immunogenic composition or a DIVA vaccine protects against a homologous and/or heterologous challenge with an Influenza A virus.

In one aspect of the present invention the immunogenic composition or a DIVA vaccine protects against a challenge with an Influenza A virus of serotypes H1 and/or H3.

The present invention also relates to the EHV vector, the immunogenic composition or the DIVA vaccine as described herein for therapeutic use.

The present invention also relates to the EHV vector, the immunogenic composition or the DIVA vaccine as described herein for use as an immunogen or vaccine The present invention also relates to the EHV vector, the immunogenic composition or the DIVA vaccine as described herein for use as a medicament.

The present invention also relates to the use of the EHV vector, the immunogenic composition or the DIVA vaccine as described herein for the manufacture of a medicament The present invention also relates to the use of the EHV vector, the immunogenic composition or the DIVA vaccine as described herein for the treatment and/or prophylaxis of Swine Influenza A virus infections in a food producing animal.

DIVA

A major advantage of an efficacious DIVA vaccine is that it allows the detection of food producing animals (preferably pigs) acutely infected or infected some time (at least ca. 3 weeks) before taking samples in a vaccinated animal population, and thus offers the possibility to monitor the spread or re-introduction of a pathogen (preferably swine influenza virus) in an animal population. Thus, it makes it possible to declare, with a certain level of confidence, that a vaccinated pig population is free of Swine Influenza A virus on the basis of laboratory test results.

The marker vaccine facilitates fast and effective administration and allows discrimination between animals infected with the field virus (disease-associated) and vaccinated animals.

The immunogenic composition or DIVA vaccine of the present invention does not comprise any antigen encoding sequence encoding N (neuraminidase) influenza antigen encoding sequences and/or NP (nucleoprotein) influenza antigen encoding sequences.

In contrast, after infection of animals with wild-type Swine Influenza A virus or vaccinated with a modified live vaccine or vaccinated with an inactivated whole virus vaccine or that have residual maternally derived antibodies, the infected/vaccinated animals produce/have specific antibodies against N (neuraminidase) and/or NP (nucleoprotein). However, in animals vaccinated with the immunogenic composition according to the present invention such specific antibodies against N (neuraminidase) and/or NP (nucleoprotein) cannot be detected.

By exemplary immuno tests and/or genomic analytical tests the animals only vaccinated with the immunogenic composition of the present invention can be differentiated from animals that were infected with the wildtype swine influenza virus or vaccinated with a modified live vaccine or vaccinated with an inactivated whole virus vaccine or that have residual maternally derived antibodies in that animals only vaccinated with the immunogenic composition of the present invention do not have any specific antibodies against N (neuraminidase) and/or NP (nucleoprotein) and any Swine Influenza A virus specific sequence encoding N (neuraminidase) and/or NP (nucleoprotein), respectively.

The present invention provides a method of differentiating food producing animals infected with Swine Influenza A virus from food producing animals vaccinated with the immunogenic composition or the DIVA vaccine as described herein, comprising a) obtaining a sample from an food producing animal, and b) analyzing said sample in an immuno test and/or genomic analytical test.

In one aspect of the present invention the immuno test comprises testing whether the sample comprises antibodies specifically recognizing the N (neuraminidase) protein or NP (nucleoprotein) protein of swine influenza.

In one aspect of the present invention the food producing animal is infected with Swine Influenza A virus if antibodies specifically recognizing the N (neuraminidase) protein or NP (nucleoprotein) protein of swine influenza have been detected.

In one aspect of the present invention the genomic analytical test comprises testing whether the sample comprises Swine Influenza A virus specific sequences encoding N (neuraminidase) and/or NP (nucleoprotein).

In one aspect of the present invention the food producing animal is infected with Swine Influenza A virus if Swine Influenza A virus specific sequences encoding N (neuraminidase) and/or NP (nucleoprotein) have been detected.

In one aspect of the present invention the immuno test is an EIA (enzyme immunoassay) or ELISA (enzyme linked immunosorbent assay), or, wherein the genomic analytical test is a PCR (polymerase chain reaction), RT-PCR (reverse transcriptase polymerase chain reaction) or real time PCR (polymerase chain reaction).

In one aspect of the present invention the food producing animal is swine

In one aspect of the present invention the sample is a serum sample.

Preferably, an antibody specific for the N (neuraminidase) and/or NP (nucleoprotein) of a wildtype SIAV is used to detect SIAV antigen in sections of the respiratory tract from a pig that is suspected to be infected with SIAV or that is vaccinated with a vaccine according to the invention. In such a case, only the sample of the infected pig or vaccinated with a modified live vaccine or vaccinated with an inactivated whole virus vaccine or that has residual maternally derived antibodies will show positive results by said N (neuraminidase) and/or NP (nucleoprotein) specific antibody. In contrast, the sample of a pig vaccinated with the vaccine of the present invention will show no results by said N (neuraminidase) and/or NP (nucleoprotein) specific antibody due to the absence of such antigens (only hemagglutinin) in the vaccine of the present invention.

However, epitope of N (neuraminidase) and/or NP (nucleoprotein) are evolutionarily conserved and specific for SIAV and a target for neutralizing antibodies.

Thus, a test could e.g. comprise wells with a N (neuraminidase) and/or NP (nucleoprotein) epitope of a wildtype SIAV cross-linked to micro-well assay plates. Said cross-linking preferably is performed through an anchor protein such as, for example, poly-L-lysine. Expression systems for obtaining a wildtype N (neuraminidase) and/or NP (nucleoprotein) epitopes are well known to the person skilled in the art. Alternatively, said N (neuraminidase) and/or NP (nucleoprotein) epitopes could be chemically synthesized.

Animals only vaccinated with the vaccine according to the present invention have not raised antibodies against the wild-type N (neuraminidase) and/or NP (nucleoprotein) epitope. However, such animals have raised antibodies against an HA (hemagglutinin) epitope according to the present invention. As a consequence, no antibodies bind to a well coated with the wildtype N (neuraminidase) and/or NP (nucleoprotein) epitope. In contrast, if a well has been coated with an HA epitope according to the present invention antibodies bind to said substituted HA epitope.

In one aspect of the present invention the ELISA is an indirect ELISA, Sandwich ELISA, a competitive ELISA or blocking ELISA.

However, the different ELISA techniques are well known to the person skilled in the art. ELISA's have been described exemplary by Wensvoort G. et al., 1988 (Vet. Microbiol. 17(2): 129-140), by Robiolo B. et al., 2010 (J. Virol. Methods. 166(1-2): 21-27) and by Colijn, E.O. et al., 1997 (Vet. Microbiology 59: 15-25).

Preferably, the test for differentiating an animal that is infected with field SIAV or vaccinated with a modified live vaccine or vaccinated with an inactivated whole virus vaccine or that has residual maternally derived antibodies and such that are only vaccinated with the vaccine of the present invention is provided by RNA isolation of respiratory cells and reverse transcriptase followed by amplification of the cDNA. Using specific primers for N (neuraminidase) and/or NP (nucleoprotein) a PCR can be performed. In such a case the pig is infected with the wildtype SIAV if there is a positive PCR signal. However, if no N (neuraminidase) and/or NP (nucleoprotein) specific sequence can be amplified the animal has been vaccinated with the vaccine of the present invention.

Further, real time based technique primers and/or probes may be used recognizing either the N (neuraminidase) and/or NP (nucleoprotein) and/or the specific HA (hemagglutinin). However, such methods are well known in the art.

In another aspect of the present invention the genomic analytical test is a PCR (polymerase chain reaction), RT-PCR (reverse transcriptase polymerase chain reaction) or real time PCR (polymerase chain reaction).

DEFINITIONS

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E.L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382,425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. Pat. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include herpes virus vectors such as derived from EHV-1 or EHV-4.

According to specific aspects of the present disclosure, the term "viral vector" or alternatively "viral construct" refers to a recombinant viral construct derived from a virus, which is selected from the families of Herpesviridae such as EHV-1, EHV-3, EHV-4, EHV-8 and EHV-9. Preferred viral vectors include Herpes virus vectors such as derived from EHV-1 or EHV-4.

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "polynucleotide", "polynucleotide sequence", "RNA sequence", cDNA sequences or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

The terms "regulatory nucleic acid", "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An “internal ribosome entry site” or “IRES” describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses (e.g. Foot-and-mouth disease virus, FMDV or Polio virus (PV), or Hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance The term “2a” or “2a peptide” means short oligopeptide sequences, described as 2a and ‘2a-like’, serve as linkers which are able to mediate a co-translational cleavage between proteins by a process defined as ribosomal-skipping. Such 2a and ‘2a-like’ sequences (from Picornaviridae and other viruses or cellular sequences) can be used to concatenate multiple gene sequences into a single gene, ensuring their co-expression within the same cell (see Luke and Ryan, 2013).

As used herein, the term “promoter” or “promoter sequence” means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

As used herein in the context of the present invention the term promoter refers especially to a functional fragment e.g. a truncation of 4pgG600 (SEQ ID NO:1) or the complementary nucleotide sequence thereof, preferably the sequence identity is (at least) 72% over entire length (or higher). Furthermore, as used herein in the context of the present invention the term promoter refers especially to a functional fragment, e.g. a truncation of 4pMCP600 (SEQ ID NO:2) or the complementary nucleotide sequence thereof, preferably the sequence identity is (at least) 78% over entire length (or higher). Most preferably “promoter” refers to p430 (SEQ ID NO:3) or p455 (SEQ ID NO: 4). The terms “p430”, “gG 430” and “430” are used synonymously and interchangeably throughout the specification, figures, sequence listing etc. The terms “p455”, “MCP 455” and “455” are used synonymously and interchangeably throughout the specification, figures, sequence listing etc.

The term “enhancer” denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term “complementary nucleotide sequences” describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms “gene”, “gene of interest”, as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. ori (origin of replication). A nucleotide sequence of interest may be any DNA or RNA sequence independently of whether it comprises a coding sequence or not.

"Open reading frame" or "ORF" refers to a length of nucleic acid sequence, either DNA or RNA that comprises a translation start signal or initiation codon, such as an ATG or AUG, and a termination codon and can be potentially translated into a polypeptide sequence.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably—two-fold to five-fold particularly preferably a three-fold to five-fold increase in specific productivity or titer. "Increased expression" may mean as well that more cells are actually expressing the gene/sequence of interest. For example increased expression may mean that the new promoters of the present invention are active for a longer period of time during the viral replication cycle relative to other promoters.

An increased expression, titer or productivity may be obtained by using a heterologous vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

An assay to measure "increased expression" is LC-MS/MS-based protein measurements such as multiple reaction monitoring (MRM); antibody-based detection methods such as Western blot, dot blot, or Immunodiffusion, and flow cytometry; and measures of biological activity by hemagglutination assay.

"Promoter activity" is measured indirectly by quantification of mRNA transcribed under control of the respective promoter. mRNA is quantified by RTqPCR relative to an endogenous standard.

The term "virus load" is well known to the person skilled in that art. The term virus load is interchangeable used with the term "viral titer" herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral nucleic acids by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma. Preferably, the term "virus load" or "virus titer" is a measure of infectious units per volume of a virus preparation. Viral titer is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", "exogenous antigen encoding sequence" with respect to the host cell, when it comes from a different (virus) species. Accordingly, the EHV-4 based promoters of the present invention are exogenous in view of an EHV-1 viral vector. As used herein in respect to a sequence or gene of interest such as an antigen the term "exogenous" or "exogenous antigen encoding sequence" means that said sequence or gene of interest, specifically said antigen is expressed out of its natural species context. Accordingly, the H3 antigen from swine IAV is one example of an exogenous antigen in respect to the EHV-1 vector. Any non-equid sequence or gene of interest such as a non-equid antigen is therefore an exogenous sequence or gene of interest or antigen according to a specific aspect of the present invention.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, an EHV-4 promoter sequence introduced into an EHV-4 viral vector at a different site or in modified form than in the EHV-4 wild type virus is by definition a heterologous sequence. As used herein in respect to a sequence or gene of interest such as an antigen, the term "heterologous" means that said sequence or gene of interest, specifically said antigen, is expressed out of its natural subspecies context. Accordingly, any non-EHV-1 specific sequence or gene of interest such as an antigen, for example an antigen from any Equid alphaherpesvirus except EHV-1, e.g. EHV-3, EHV-8, is therefore a heterologous sequence or gene of interest or antigen according to a specific aspect of the present invention.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment or derivative" of a promoter sequence means that the fragment or derivative still effects promoter activity. Functional assays of how to assess promoter activity are well known to one of ordinary skill in the art (Bustin 2000, Nolan et al. 2006). An exemplary embodiment of such a functional assay includes e.g. a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNAse I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide, or a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

EHV-1 and EHV-4/Recombinant Vector Technology Definitions

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

A "herpes virus" or "herpes virus vector" refers to a species in the family Herpesviridae in the order Herpesvirales.

The term "Equid herpes virus vector" or "Equid herpes virus" or "EHV" means a member of the family Herpesviridae affecting horses. To date eight different species of equid herpesviruses have been identified, five belonging to the subfamily Alphaherpesvirinae (EHV-1, EHV-3, EHV-4, EHV-8 and EHV-9) and three to the Gammaherpesvirinae. (Virus Taxonomy: 2015 Release EC 47, London, UK, July 2015; Email ratification 2016 (MSL #30)).

The term "EHV-1" means Equid Alphaherpesvirus 1, a member of the subgenus *Varicellovirus* in the genus Alphaherpesvirinae in the family Herpesviridae. A non-limiting reference sequence for EHV-1 would be for example the wild-type EHV-1 strain ab4 (Genbank accession number AY665713.1) or the RacH (Hübert 1996).

The term EHV-4 means Equid Alphaherpesvirus 4, a member of the subgenus *Varicellovirus* in the genus Alphaherpesvirinae in the family Herpesviridae.

The term "two or more EHV vectors" encompass two, three, four, five or six EHV vectors.

The term "inserted into ORF70" and "insertion site is ORF70" means that a DNA fragment was inserted into the genomic DNA at a location encoding the Equid herpesvirus 1 open reading frame 70. The insertion referred to resulted in a deletion of the 801 5' basepairs of ORF70 leaving the remaining 423 bp of the 3' end intact but abolishing expression of the orf70 gene product glycoprotein G. The glycoprotein G of several Alphaherpesviruses including EHV-1 was shown to be secreted from infected cells and function as an immunomodulatory protein by binding pro-inflammatory cytokines. Abolishment of its expression in the viral vector should increase the immunogenicity of the viral infection as compared to a wild-type EHV-1 with intact glycoprotein G expression.

The term "inserted into ORF1/3" and "insertion site is ORF1/3" means that a DNA fragment was inserted in the viral genome at a position where by accidental deletion over passaging during the attenuation procedure of the vaccine strain EHV-1 RacH a 1283 bp fragment comprising 90% of ORF1 and the entire ORF2 were lost. This insertion site was chosen because the likelihood that expression of a transgene from this location would interfere with viral replication was expected to be extremely low.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition. Preferably, the immunogenic composition induces an immune response and, more preferably, confers protective immunity against one or more of the clinical signs of a swine IAV infection. The host is also described as "food producing animal". In case where the host displays a protective immunological response such that resistance to new infection will be enhanced and/or the clinical severity of the disease reduced, the immunogenic composition is described as a "vaccine".

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope. Further, the term "antigen encoding sequence" relates to sequences encoding an antigen. Preferably the antigen encoding sequence is a nucleic acid sequence such as a cDNA sequence. However, the term "nucleic acid sequence" has been defined elsewhere herein.

The term "at least one exogenous antigen encoding sequence" also encompasses more than one exogenous antigen encoding sequence. Thus, it has to be understood that the term "at least one exogenous antigen encoding sequence" encompasses two, three, four, five or six exogenous antigen encoding sequences. Accordingly, the term "at least two exogenous antigen encoding sequences" encompasses three, four, five or six exogenous antigen encoding sequences.

The term "different exogenous antigen encoding sequences" are sequences that differ in their sequence among each other.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, June 28-Jul. 3, 1998. (The teachings and content of which are all incorporated by reference herein.)

The term "immunizing" relates to an active immunization by the administration of an immunogenic composition to a food producing animal to be immunized, thereby causing an immunological response against the antigen included in such immunogenic composition.

The term "in need" or "of need", as used herein means that the administration/treatment is associated with the boosting or improvement in health or clinical signs or any other positive medicinal effect on health of the animals which receive the immunogenic composition in accordance with the present invention.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus that has been irradiated (ultraviolet (UV), X-ray, electron beam or gamma radiation), heated, or chemically treated to inactivate or kill such virus while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus. It is critical to adjust the amount of formalin to ensure that the material is inactivated but not so much that side effects from a high dosage occur.

More particularly, the term "inactivated" in the context of a virus means that the virus is incapable of replication in vivo or in vitro. For example, the term "inactivated" may refer to a virus that has been propagated in vitro, and has then been inactivated using chemical or physical means so that it is no longer capable of replicating.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the EHV-1 RacH viral vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the EHV-1 (preferably RacH) viral vector as claimed, is suitable for the generation of a modified live vaccine (MLV) or modified live immunogenic composition.

The term "treatment and/or prophylaxis" refers to the lessening of the incidence of the particular Swine influenza A virus infection in a herd or the reduction in the severity of clinical signs caused by or associated with the particular Swine influenza A virus infection. Thus, the term "treatment and/or prophylaxis" also refers to the reduction of the number of animals in a herd that become infected with the particular Swine influenza A virus (=lessening of the incidence of the particular Swine influenza A virus infection) or to the reduction of the severity of clinical signs normally associated with or caused by a Swine influenza A virus infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to an animal or herd of animals in need of or that could benefit from such a treatment/prophylaxis. The term "treatment" refers to the administration of the effective amount of the immunogenic composition once the animal or at least some animals of the herd is/are already infected with such Swine influenza A virus and wherein such animals already show some clinical signs caused by or associated with such Swine influenza A virus infection. The term "prophylaxis" refers to the administration to an animal prior to any infection of such animal with Swine influenza A virus or at least where such animal or none of the animals in a group of animals do not show any clinical signs caused by or associated with the infection by such Swine influenza A virus. The terms "prophylaxis" and "preventing" are used interchangeable in this application.

The term "clinical signs" as used herein refers to signs of infection of an animal from Swine influenza A virus. The clinical signs of infection depend on the pathogen selected. Examples for such clinical signs include but are not limited to respiratory distress, otitis, roughened hair coat, slight fever, depression, and reduced appetite. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight loss, dehydration, lameness, wasting, paleness of the skin, unthriftiness and the like.

Preferably, the clinical signs lessened in incidence or severity in a treated animal compared to animals that are either not treated or treated with an immunogenic composition that was available prior to the present invention but subsequently infected by the particular Swine influenza A virus refer to a reduction in weight loss, a lower virus load in lungs, a reduction in lung lesions, a reduced and/or shortened shedding of virus, a reduced rectal temperature, reduced clinical symptoms (in particular respiratory symptoms), increased induction of (neutralizing) anti-Swine Influenza A virus antibodies, increased stimulation of T-cells against Swine Influenza A virus, increased stimulation of B-cells against Swine Influenza A virus, and a reduction of proinflammatory cytokines, e.g. IL1β, in lungs, or combinations thereof.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Such effective amount is able to lessen the incidence of the particular Swine Influenza A virus infection in a herd or to reduce the severity of clinical signs of the particular Swine Influenza A virus infection. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized animal that has been exposed to disease or infection. That is, the severity of the deleterious effects of the infection are lessened in a vaccinated animal. Infection may be reduced, slowed, or possibly fully prevented, in a vaccinated animal. Herein, where complete prevention of infection is meant, it is specifically stated. If complete prevention is not stated then the term includes partial prevention. A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

Herein, "reduction of the incidence and/or severity of clinical signs" or "reduction of clinical symptoms" means, but is not limited to, reducing the number of infected animals in a group, reducing or eliminating the number of animals exhibiting clinical signs of infection, or reducing the severity of any clinical signs that are present in one or more animals, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more animals receiving the therapeutic composition of the present invention by at least 10% in comparison to animals not receiving the composition and that become infected. More preferably clinical signs are reduced in animals receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of animals vs. a non-vaccinated control group of animals. The term "statistically significant reduction of clinical symptoms" means, but is not limited to, the frequency in the incidence of at least one clinical symptom in the vaccinated group of animals is at least 10%, preferably 20%, more preferably 30%, even more preferably 50%, and even more preferably 70% lower than in the non-vaccinated control group after the challenge the infectious agent.

The term "pathogen" is well known to the person skilled in the art. However, the term "pathogen" comprises bacteria and viruses.

The term "food producing animal" means animals which are used for human consumption such as swine, cattle, poultry, fish and the like, preferably swine. The term "food producing animal" excludes, Equidae such as horses.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "shedding" refers to secretions such as nasal discharges and, further, to aerosols created by coughing or sneezing. Thus, shedding may be determined by examining the virus titer in nasal swabs or by the virus titer in the lungs. The term "shedding" further encompasses the transfer of virus to susceptible animals (i.e. sentinels). It is in the general knowledge of a person skilled in the art how to measure the viral shedding.

The term "anti-Swine Influenza A virus antibodies" refers to antibodies that are specific towards Swine Influenza A virus. Examples of such anti-Swine Influenza A virus antibodies comprise, but are not limited to maternally derived antibodies by vaccination of sows with a Swine Influenza A virus vaccine or to maternally derived antibodies by Swine Influenza A virus infection of sows. Further, the anti-Swine Influenza A virus antibodies in the piglet may have been developed in response to a Swine Influenza A virus infection of the piglet. The term "anti-Swine Influenza A virus antibodies" shall further mean, but is not limited to, a piglet that has or is exposed to (passive transfer of maternally antibodies) a detectable anti-SIAV antibody titer, preferably of at least 1:10, more preferably of more than 1:20, even more preferably of more than 1:40, even more preferably of more than 1:80, even more preferably of 1:160, even more preferably of more than 1:320, and most preferably of more than 1:640. Preferably, that anti-Swine Influenza A virus antibody titer is detectable and quantifiable in a specific anti-Swine Influenza A virus immune assay such as hemagglutination inhibition assay, ELISA or Serum Neutralization test.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in said animal.

"Mortality", in the context of the present invention, refers to death caused by an infection, and includes the situation where the infection is so severe that an animal is euthanized to prevent suffering and provide a humane ending to its life.

Formulations

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitnoeally, intracutaneously, and depending on the desired duration and effectiveness of the treatment, the compositions according to the invention may be administered once or several times, also intermittently, for instance on a daily basis for several days, weeks or months and in different dosages such as about $1\times10^4$ to $1\times10^9$ (see viral titer above). In a specific aspect of the present invention the dosage is about $1\times10^4$ to $1\times10^7$ $TCID_{50}$.

Antigen Definitions

The term "swine influenza virus" is known by the person skilled in the art. The term swine influenza virus refers to a type A or type C influenza virus from the family orthomyxovirus that causes swine influenza. While orthomyxovirus has three groups: type A, type B and type C, only type A and type C influenza viruses infect pigs. Preferably, the swine influenza virus is a Swine Influenza A virus. Subtypes of swine influenza virus include H1N1, H1N2, H3N2, and H3N1. H9N2 and H5N1 can also be found in pigs. Preferably, a swine influenza virus is an influenza virus that has been isolated from swine.

The terms "HA" or "H", "NA" or "N" and "NP" are known by the person skilled in the art. However, in general, type A influenza viruses are divided into 17 H (hemagglutinin) and 10 N (Neuraminidase) subtypes which can give rise to many possible combinations (designated as H1N1, H1N2 . . . H2N1, H2N2 . . . H5N1, H5N2 . . . and so on). H (hemagglutinin) and N (neuraminidase) are surface glycoproteins in influenza A viruses such as SIAV. Further, N is the major antigenic target of neutralizing antibodies. Furthermore, NP (nucleoprotein) forms the nucleocapsid.

DIVA Definitions

The term "DIVA (differentiation between infected and vaccinated animals)" refers to a vaccine that can be used for differentiating a vaccinated animal from a naturally infected animal.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting.

The term "obtained" may comprise an isolation and/or purification step known to the person skilled in the art, preferably using precipitation, columns etc.

The term "immuno tests" and "genomic analytical tests" is the basis for differentiating animals vaccinated with the immunogenic composition according to the present invention and animals infected with the naturally occurring (disease-associated) swine influenza virus. Examples of immuno tests include any enzyme-immunological or immunochemical detection method such as ELISA (enzyme linked immunosorbent assay), EIA (enzyme immunoassay), RIA (radioimmunoassay), sandwich enzyme immune tests, fluorescent antibody test (FAT) electrochemiluminescence sandwich immunoassays (ECLIA), dissociation-enhanced lanthanide fluoro immuno assay (DELFIA) or solid phase immune tests, immunofluorescent test (IFT), immunohistological staining, Western blot analysis or any other suitable method available to technicians skilled in the art. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

The term "genomic analytical test" refers to a genomic analytical method based upon the polymerase chain reaction (PCR), reverse transcription polymerase chain reaction (RT-PCR), real-time PCR (r-PCR) or real time reverse transcription PCR (rRT-PCR), Templex-PCR, nucleic-acid sequence based amplification (NASBA), and isothermal amplification methods using polymerases and specific oligonucleotides as primers. The aforementioned amplification methods are well known in the art.

Clauses

The following Clauses are described herein:

The invention provides the following clauses:

Compound

1. An EHV vector comprising (i) at least one exogenous antigen encoding sequence relating to a pathogen infecting food producing animals, (ii) said exogenous antigen encoding sequence is inserted into ORF70, (iii) said exogenous antigen encoding sequence is operably linked to a promoter sequence.

2. An immunogenic composition comprising an EHV vector according to clause 1 and optionally a pharmaceutical carrier.

3. An immunogenic composition comprising an EHV vector comprising (i) at least one exogenous antigen encoding sequence relating to a pathogen infecting food producing animals, (ii) said exogenous antigen encoding sequence is inserted into ORF70, (iii) said exogenous antigen encoding sequence is operably linked to a promoter sequence 4. An EHV vector comprising (i) at least one exogenous antigen encoding sequence relating to a pathogen infecting food producing animals, (ii) said exogenous antigen encoding sequence is inserted into an insertion site, (iii) said exogenous antigen encoding sequence is operably linked to a promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

5. An immunogenic composition comprising an EHV vector according to clause 4 and optionally a pharmaceutical carrier.

6. An immunogenic composition comprising an EHV vector comprising (i) at least one exogenous antigen encoding sequence relating to a pathogen infecting food producing animals, (ii) said exogenous antigen encoding sequence is inserted into an insertion site, (iii) said exogenous antigen encoding sequence is operably linked to a promoter sequence comprising 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

7. An EHV vector comprising (i) at least two exogenous antigen encoding sequences relating to a pathogen infecting food producing animals, (ii) said exogenous antigen encoding sequences are inserted into insertion sites, (iii) said exogenous antigen encoding sequences are operably linked to promoter sequences.

8. An immunogenic composition comprising an EHV vector according to clause 7 and optionally a pharmaceutical carrier.

9. An immunogenic composition comprising an EHV vector comprising (i) at least two exogenous antigen encoding sequences relating to a pathogen infecting food producing animals, (ii) said exogenous antigen encoding sequences are inserted into insertion sites, (iii) said exogenous antigen encoding sequences are operably linked to promoter sequences.

10. An immunogenic composition comprising two or more EHV vectors according to any one of clauses 1 to 9.

11. The immunogenic composition according to clause 10, wherein the immunogenic composition comprises two EHV vectors.

12. The immunogenic composition according to clause 10, wherein the two or more EHV vectors comprise different exogenous antigen encoding sequences.

13. A DIVA vaccine comprising one or more EHV vectors according to any one of clauses 1 to 12.

14. The EHV vector, the immunogenic composition or the DIVA vaccine according to any one of clauses 1 to 13, wherein the EHV vector is recombinant.

15. The EHV vector, the immunogenic composition or the DIVA vaccine according to any one of clauses 1 to 14, wherein the EHV vector is RacH or RacH SE.

16. The EHV vector, the immunogenic composition or the DIVA vaccine according to any one of clauses 1 to 14, wherein the EHV vector is selected from the group consisting of EHV-1, EHV-3, EHV-4, EHV-8 and EHV-9.

17. The EHV vector, the immunogenic composition or the DIVA vaccine according to any one of clauses 1 to 16, wherein the EHV vector is EHV-1.

18. The EHV vector, the immunogenic composition or the DIVA vaccine according to any one of clauses 1 to 17, wherein the food producing animals is swine.

19. The EHV vector, the immunogenic composition or the DIVA vaccine according to any one of clauses 1 to 18, wherein the pathogen infecting food producing animals is an Influenza Virus, preferably Swine influenza A virus.

20. The EHV vector, the immunogenic composition or the DIVA vaccine according to any one of clauses 1 to 19, wherein the exogenous antigen encoding sequence is a hemagglutinin encoding sequence.

21. The EHV vector, the immunogenic composition or the DIVA vaccine according to any one of clauses 1 to 20, wherein the exogenous antigen encoding sequence is a hemagglutinin encoding sequence and the hemagglutinin influenza subtype is selected from the group consisting of H1, H2, H3, H4, H5, H6, H7, H8, H9, H10, H11, H12, H13, H14, H15, H16, H17 and H18.

22. The EHV vector, the immunogenic composition or the DIVA vaccine according to any one of clauses 1 to 21, wherein the exogenous antigen encoding sequence is a hemagglutinin encoding sequence and the hemagglutinin influenza subtype is H1 and/or H3.

23. The EHV vector, the immunogenic composition or the DIVA vaccine according to any one of clauses 1 to 22, wherein the exogenous antigen encoding sequence is a hemagglutinin encoding sequence and the hemagglutinin influenza A antigens have a swine origin.

24. The EHV vector, the immunogenic composition or the DIVA vaccine according to any one of clauses 1 to 23, wherein the EHV vector comprises at least two hemagglutinin influenza antigen encoding sequences.

25. The EHV vector, the immunogenic composition or the DIVA vaccine according to any one of clauses 1 to 24, wherein the EHV vector comprises at least four hemagglutinin influenza antigen encoding sequences.

26. The EHV vector, the immunogenic composition or the DIVA vaccine according to any one of clauses 1 to 25, wherein the EHV vector comprises four hemagglutinin influenza antigen encoding sequences.

27. The EHV vector, the immunogenic composition or the DIVA vaccine according to any one of clauses 1 to 26, wherein the exogenous antigen encoding sequence is a hemagglutinin encoding sequence and the hemagglutinin influenza antigen encoding sequence is selected from a group of strains consisting of A/swine/Italy/116114/2010 (H1N2), A/swine/Italy/7680/2001(H3N2), A/swine/Gent/132/2005(H1N1), A/swine/Italy/4675/2003 (H1N2), A/swine/Italy/259543/2003 (H1N2), A/swine/Denmark/

13772-1/2003(H1N1), A/swine/England/MD0040352R/2009(H1N1), A/swine/Hungary/13509/2007(H3N2), A/swine/Italy/13962/95(H3N2), A/swine/Cotes d'Armor/1121/00(H1N1), A/Swine/Colorado/1/77, A/Swine/Colorado/23619/99, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/7 8, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/985 A/Swine/Wisconsin/458/98, A/Swine/Wisconsin/464/98 and A/Swine/Wisconsin/14094/99.

28. The EHV vector, the immunogenic composition or the DIVA vaccine according to any one of clauses 1 to 27, wherein the exogenous antigen encoding sequence is a hemagglutinin encoding sequence and the hemagglutinin influenza antigen encoding sequence is selected from a group of strains consisting of A/swine/Italy/116114/2010 (H1N2), A/swine/Italy/7680/2001(H3N2), A/swine/Gent/132/2005(H1N1) and A/swine/Italy/4675/2003 (H1N2).

29. The EHV vector, the immunogenic composition or the DIVA vaccine according to any one of clauses 1 to 28, wherein the exogenous antigen encoding sequence is a hemagglutinin encoding sequence and the hemagglutinin influenza antigen encoding sequence encodes an amino acid sequence selected from a group consisting of SEQ ID NO:26, SEQ ID NO:27, SEQ ID NO:28 and SEQ ID NO:29.

30. The EHV vector, the immunogenic composition or the DIVA vaccine according to any one of clauses 1 to 29, wherein the exogenous antigen encoding sequence is a hemagglutinin encoding sequence and the hemagglutinin influenza antigen encoding sequence comprises a nucleic acid sequence encoding an amino acid sequence with at least 70% identity to the amino acid sequence as set forth in SEQ ID NO:26, SEQ ID NO:27, SEQ ID NO:28 and SEQ ID NO:29.

31. The EHV vector, the immunogenic composition or the DIVA vaccine according to any one of clauses 1 to 30, wherein the exogenous antigen encoding sequence is a hemagglutinin encoding sequence and the hemagglutinin influenza antigen encoding sequence comprises a nucleic acid sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:26, SEQ ID NO:27, SEQ ID NO:28 and SEQ ID NO:29.

32. The EHV vector, the immunogenic composition or the DIVA vaccine according to any one of clauses 1 to 31, wherein the exogenous antigen encoding sequence is a N (neuraminidase) encoding sequence and the N subtype is selected from the group consisting of N1, N2, N3, N4, N5, N6, N7, N8, N9 and N10.

33. The EHV vector, the immunogenic composition or the DIVA vaccine according to any one of clauses 1 to 32, wherein the EHV vector, the immunogenic composition or the DIVA vaccine does not comprise N (neuraminidase) influenza antigen encoding sequences.

34. The EHV vector, the immunogenic composition or the DIVA vaccine according to any one of clauses 1 to 33, wherein the EHV vector, the immunogenic composition or the DIVA vaccine does not comprise NP (nucleoprotein) influenza antigen encoding sequences.

35. The EHV vector, the immunogenic composition or the DIVA vaccine according to any one of clauses 1 to 34, wherein the EHV vector comprises additional regulatory sequences such as a termination signal or polyadenylation sequence.

Insertion Site:

36. The EHV vector, the immunogenic composition or the DIVA vaccine according to any one of clauses 4 to 34, wherein said insertion site is ORF1/3.

37. The EHV vector, the immunogenic composition or the DIVA vaccine according to any one of clauses 4 to 34, wherein said insertion site is ORF70.

38. The EHV vector, the immunogenic composition or the DIVA vaccine according to any one of clauses 1 to 37, wherein a first exogenous antigen encoding sequence relating to a pathogen infecting food producing animals is inserted into ORF70.

39. The EHV vector, the immunogenic composition or the DIVA vaccine according to any one of clauses 1 to 38, wherein a second exogenous antigen encoding sequence relating to a pathogen infecting food producing animals is inserted into ORF1/3.

40. The EHV vector, the immunogenic composition or the DIVA vaccine according to any one of clauses 1 to 39, wherein the insertion into ORF70 is characterized by a partial deletion, truncation, substitution, modification or the like in ORF70, whereby ORF71 remains functional.

41. The EHV vector, the immunogenic composition or the DIVA vaccine according to any one of clauses 1 to 40, wherein the insertion into ORF70 is characterized by (i) the deletion of an approximately 801 bp portion within ORF70 for RacH (SEQ ID NO: 20) or a 70%, 80%, 85%, 90%, 95%, 99% homologous and/or identical sequence thereof, or (ii) the insertion into ORF70 is characterized by the deletion of an approximately 801 bp portion within ORF70 for RacH (SEQ ID NO.: 20) or a 70%, 80%, 85%, 90%, 91%, 92%, 93%, 94%, 95%, 96%, 97%, 98%, 99% homologous and/or identical sequence deletion thereof in any other strain, or (iii) the insertion into ORF70 is characterized by the deletion of an approximately 801 bp deletion within ORF70 for the wild-type EHV-1 strain ab4 (Genbank accession number AY665713.1), whereby the deleted portion in the wild-type ab4 genome sequence is located between nucleotides 127681 and 128482 (SEQ ID NO.: 19) or a 70%, 80%, 85%, 90%, 91%, 92%, 93%, 94%, 95%, 96%, 97%, 98%, 99% homologous and/or identical sequence thereof or (iv) the insertion into ORF70 is characterized by the deletion of an approximately 801 bp deletion within ORF70 for the wild-type EHV-1 strain ab4 (Genbank accession number AY665713.1), whereby the deleted portion in the wild-type ab4 genome sequence is located between nucleotides 127681 and 128482 (SEQ ID NO.: 19) or a 70%, 80%, 85%, 90%, 91%, 92%, 93%, 94%, 95%, 96%, 97%, 98%, 99% homologous and/or identical sequence deletion thereof in any other strain.

42. The EHV vector, the immunogenic composition or the DIVA vaccine according to any one of clauses 1 to 41, wherein the EHV-1 vector comprises at least one flanking regions selected from the group consisting of: SEQ ID NO: 13, SEQ ID NO: 14, SEQ ID NO: 15, SEQ ID NO: 16, SEQ ID NO: 17, and SEQ ID NO: 18 and a 70%, 80%, 85%, 90%, 95%, 96%, 97%, 98%, 99% homologous and/or identical sequence of any one of these sequences.

43. The EHV vector, the immunogenic composition or the DIVA vaccine according to any one of clauses 1 to 42, wherein the EHV-1 vector comprises (i) at least one left ORF70 flanking region selected from the group consisting of: SEQ ID NO: 13, SEQ ID NO: 15, and SEQ ID NO: 17, and (ii) at least one right ORF70 flanking region selected from the group consisting of: SEQ ID NO: 14, SEQ ID NO: 16, and SEQ ID NO: 18.

Promoter:

44. The EHV vector, the immunogenic composition or the DIVA vaccine according to any one of clauses 1 to 3 and clauses 7 to 43, wherein the promoter sequence is selected from the group consisting of: SV40 large T, HCMV and MCMV immediate early gene 1, human elongation factor alpha promoter, baculovirus polyhedron promoter, a functional fragment of 4pgG600 (SEQ ID NO:1), preferably said functional fragment is p430 (SEQ ID NO:3), a functional fragment of the complementary nucleotide sequence of 4pgG600 (SEQ ID NO:1), a functional fragment of 4pMCP600 (SEQ ID NO:2), preferably said functional fragment is p455 (SEQ ID NO:4), a functional fragment of the complementary nucleotide sequence of 4pMCP600 (SEQ ID NO:2).

45. The EHV vector, the immunogenic composition or the DIVA vaccine according to any one of clauses 1 to 3 and clauses 7 to 44, wherein the promoter sequence comprises 4pgG600 (SEQ ID NO:1) or 4pMCP600 (SEQ ID NO:2) or the complementary nucleotide sequences thereof or a functional fragment or a functional derivative thereof or the complementary nucleotide sequences thereof.

46. The EHV vector, the immunogenic composition or the DIVA vaccine according to any one of clauses 4 to 6 and 45, wherein the functional fragment or derivative of the promoter sequence has a homology of 80%, 85%, preferably 90%, 91%, 92%, 93%, 94%, more preferably 95%, 96%, 97%, 98%, 99%, 99.9%.

47. The EHV vector, the immunogenic composition or the DIVA vaccine according to any one of clauses 4 to 6 and 45 or 46, wherein the functional fragment or derivative of the promoter sequence has a length of 550 nucleotides, preferably 500, 490, 480, 470, 460, 455, 450, 445, 440, 435, 434, 433, 432, 431, 430 nucleotides, most preferably 455 or 430 nucleotides.

48. The EHV vector, the immunogenic composition or the DIVA vaccine according to any one of clauses 4 to 6 and 45 to 47, wherein the functional fragment of the promoter sequence is a truncation of 4pgG600 (SEQ ID NO:1) or the complementary nucleotide sequence thereof, preferably the sequence identity is (at least) 72% over entire length (or higher).

49. The EHV vector, the immunogenic composition or the DIVA vaccine according to any one of clauses 4 to 6 and 45 to 48, wherein the functional fragment of the promoter sequence of 4pgG600 (SEQ ID NO:1) is the fragment designated p430 (SEQ ID NO:3) or a sequence having 80%, 85%, 90%, 91%, 92%, 93%, 94%, 95%, 96%, 97%, 98%, 99%, 99.9% identity to SEQ ID NO:3.

50. The EHV vector, the immunogenic composition or the DIVA vaccine according to any one of clauses 4 to 6 and 45 to 48, wherein the functional fragment of the promoter sequence is a truncation of 4pMCP600 (SEQ ID NO:2) or the complementary nucleotide sequence thereof, preferably the sequence identity is (at least) 78% over entire length (or higher).

51. The EHV vector, the immunogenic composition or the DIVA vaccine according to any one of clauses 4 to 6 and 45 to 48, wherein the functional fragment of the promoter sequence of 4pMCP600 (SEQ ID NO:2) is the fragment designated p455 (SEQ ID NO:4) or a sequence having 80%, 85%, 90%, 91%, 92%, 93%, 94%, 95%, 96%, 97%, 98%, 99%, 99.9% identity to SEQ ID NO:4.

52. The EHV vector, the immunogenic composition or the DIVA vaccine according to any one of clauses 1 to 51, wherein the EHV vector comprises one or more further regulatory sequences such as a termination signal, a polyadenylation signal or a regulatory element like IRES and/or 2a peptide.

Specific Combinations of Promoters and Antigens:

53. The EHV vector, the immunogenic composition or the DIVA vaccine according to any one of clauses 1 to 52, wherein the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28.

54. The EHV vector, the immunogenic composition or the DIVA vaccine according to clause 53, wherein the functional fragment of the promoter sequence 4pgG600 (SEQ ID NO:1) is the fragment designated p430 (SEQ ID NO:3).

55. The EHV vector, the immunogenic composition or the DIVA vaccine according to any one of clauses 1 to 54, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27).

56. The EHV vector, the immunogenic composition or the DIVA vaccine according to clause 55, wherein the functional fragment of the promoter sequence 4pMCP600 (SEQ ID NO:2) is the fragment designated 455p455 (SEQ ID NO:4).

57. The EHV vector, the immunogenic composition or the DIVA vaccine according to any one of clauses 1 to 56, wherein the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28 and, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27.

58. The EHV vector, the immunogenic composition or the DIVA vaccine according to clause 57, wherein the functional fragment of the promoter sequence 4pgG600 (SEQ ID No. 1) is the fragment designated p430 (SEQ ID NO:3) and, wherein the functional fragment of the promoter sequence 4pMCP600 (SEQ ID NO:2) is the fragment designated 455p455 (SEQ ID NO:4).

59. The immunogenic composition or the DIVA vaccine according to clause 57 or 58, wherein the immunogenic composition or the DIVA vaccine is bivalent.

60. The EHV vector, the immunogenic composition or the DIVA vaccine according to any one of clauses 1 to 59, wherein the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29.

61. The EHV vector, the immunogenic composition or the DIVA vaccine according to clause 60, wherein the functional fragment of the promoter sequence 4pgG600 (SEQ ID NO:1) is the fragment designated p430 (SEQ ID NO:3).

62. The EHV vector, the immunogenic composition or the DIVA vaccine according to any one of clauses 1 to 61, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26.

63. The EHV vector, the immunogenic composition or the DIVA vaccine according to clause 62, wherein the functional fragment of the promoter sequence 4pMCP600 (SEQ ID NO:2) is the fragment designated 455p455 (SEQ ID NO:4).

64. The EHV vector, the immunogenic composition or the DIVA vaccine according to any one of clauses 1 to 63, wherein the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29, and wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26).

65. The EHV vector, the immunogenic composition or the DIVA vaccine according to clause 64, wherein the functional fragment of the promoter sequence 4pgG600 (SEQ ID No. 1) is the fragment designated p430 (SEQ ID NO:3) and wherein the functional fragment of the promoter sequence 4pMCP600 (SEQ ID NO:2) is the fragment designated 455p455 (SEQ ID NO:4).

66. The immunogenic composition or the DIVA vaccine according to clause 64 or 65, wherein the immunogenic composition or the DIVA vaccine is bivalent.

67. The EHV vector, the immunogenic composition or the DIVA vaccine according to any one of clauses 1 to 66, wherein said immunogenic composition comprises a first EHV vector comprising the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 28 and, wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 27 and wherein said immunogenic composition comprises a second EHV vector comprising the promoter sequence 4pgG600 (SEQ ID NO:1) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 29, and wherein the promoter sequence 4pMCP600 (SEQ ID NO:2) or the complementary nucleotide sequences thereof or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO: 26.

68. The EHV vector, the immunogenic composition or the DIVA vaccine according to clause 67, wherein the functional fragment of the promoter sequence 4pgG600 (SEQ ID NO:1) is the fragment designated p430 (SEQ ID NO:3) and wherein the functional fragment of the promoter sequence 4pMCP600 (SEQ ID NO:2) is the fragment designated 455p455 (SEQ ID NO:4).

69. The immunogenic composition or the DIVA vaccine according to clause 67 or 68, wherein the immunogenic composition or DIVA vaccine is tetravalent.

70. The immunogenic composition or DIVA vaccine according to any one of clauses 1 to 69, wherein said immunogenic composition or DIVA vaccine is formulated for a single-dose administration.

71 . The immunogenic composition or DIVA vaccine according to any one of clauses 1 to 70, wherein said immunogenic composition or DIVA vaccine is administered intramuscular or intranasal.

72. The immunogenic composition or DIVA vaccine according to any one of clauses 1 to 71 , wherein the immunogenic composition or DIVA vaccine is safe for pigs within the first six weeks of age, within the first two weeks of age, within the first week of age or within the first day of age.

73. The immunogenic composition or DIVA vaccine according to any one of clauses 1 to 72, wherein the immunogenic composition or DIVA vaccine further comprises a pharmaceutically acceptable carrier.

74. The immunogenic composition or DIVA vaccine according to clauses 73, wherein said pharmaceutically acceptable carrier is aqua ad injection, cell culture media or a resuspension buffer.

75. The immunogenic composition or DIVA vaccine according to clause 74, wherein said resuspension buffer is phosphate buffered saline.

76. The immunogenic composition or DIVA vaccine according to any one of clauses 1 to 75, wherein the immunogenic composition or DIVA vaccine comprises $1\times10^4$ to $1\times10^9$ $TCID_{50}$, preferably between $1\times10^4$ to $1\times10^8$ $TCID_{50}$, even more preferably $1\times10^4$ to $1\times10^7$ $TCID_{50}$ of the EHV vector.

77. The immunogenic composition or DIVA vaccine according to any one of clauses 1 to 76, wherein said immunogenic composition is a vaccine.

78. The immunogenic composition or DIVA vaccine according to any one of clauses 1 to 77, wherein said immunogenic composition or DIVA vaccine is a multivalent vaccine.

79. The immunogenic composition or DIVA vaccine according to any one of clauses 1 to 78, wherein said immunogenic composition or DIVA vaccine is a bivalent vaccine, tetravalent vaccine, hexavalent vaccine or heptavalent vaccine.

80. The immunogenic composition or DIVA vaccine according to any one of clauses 1 to 79, wherein said immunogenic composition or DIVA vaccine is a bivalent vaccine or tetravalent vaccine.

81. The immunogenic composition or DIVA vaccine according to any one of clauses 1 to 80, wherein the immunogenic composition or DIVA vaccine is effective in the treatment and/or prophylaxis of clinical signs caused by Swine Influenza A virus in a food producing animal of need.

82. The immunogenic composition or DIVA vaccine according to any one of clauses 1 to 81, wherein the immunogenic composition or DIVA vaccine protects against a homologous and/or heterologous challenge with a Swine Influenza A virus.

83. The immunogenic composition or DIVA vaccine according to any one of clauses 1 to 82, wherein the immunogenic composition or DIVA vaccine protects against a challenge with a Swine Influenza A virus of serotypes H1 and/or H3.

Kits

84. A kit comprising the immunogenic composition or DIVA vaccine of any one of clauses 2, 3, 5, 6 and 8 to 83.

85. The kit according to clause 84, wherein the kit further comprises an instruction letter for the treatment and/or prophylaxis of Swine Influenza A virus.

Method of Treatment

86. A method for immunizing a food producing animal comprising administering to such food producing animal an immunogenic composition or a DIVA vaccine of any one of clauses 2, 3, 5, 6 and 8 to 83.

87. A method for the treatment or prophylaxis of clinical signs caused by influenza A virus in a food producing animal of need, the method comprising administering to the food producing animal a therapeutically effective amount of an immunogenic composition or a DIVA vaccine according to any one of clauses 2, 3, 5, 6 and 8 to 83.

88. A method of reducing the virus titers in lungs in a food producing animal of need, in comparison to a food producing animal of a non-immunized control group of the same species, the method comprising administering to the food producing animal a therapeutically effective amount of an immunogenic composition or a DIVA vaccine according to any one of clauses 2, 3, 5, 6 and 8 to 83.

89. A method of vaccinating a food producing animal of need having anti-Swine Influenza A virus antibodies comprising the step of administering to said food producing animal a therapeutically effective amount of an immunogenic composition or a DIVA vaccine according to any one of clauses 2, 3, 5, 6 and 8 to 83.

90. A method of providing maternally derived immunity against Influenza A virus in a young food producing animal comprising administering to the mother of said young food producing animal a therapeutically effective amount of an immunogenic composition or a DIVA vaccine according to any one of clauses 2, 3, 5, 6 and 8 to 83 while said mother is pregnant with said young food producing animal.

91. A method of providing increased protection against Influenza A virus infection in a young food producing animal of need, wherein the mother of said young food producing animal is to be vaccinated with a therapeutically effective amount of an immunogenic composition or a DIVA vaccine according to any one of clauses 2, 3, 5, 6 and 8 to 83 while said mother is pregnant with said young food producing animal and/or said young food producing animal is to be vaccinated with a therapeutically effective amount of said immunogenic composition or DIVA vaccine within three weeks of age.

92. The immunogenic composition or DIVA vaccine according to any one of clauses 2, 3, 5, 6 and 8 to 83 for use in a method for immunizing a food producing animal, the method comprising administering to the food producing animal a therapeutically effective amount of said immunogenic composition or DIVA vaccine.

93. The immunogenic composition or DIVA vaccine according to any one of clauses 2, 3, 5, 6 and 8 to 83 for use in a method for the treatment or prophylaxis of clinical signs caused by influenza A virus in a food producing animal of need, the method comprising administering to the food producing animal a therapeutically effective amount of said immunogenic composition or DIVA vaccine.

94. The immunogenic composition or DIVA vaccine according to any one of clauses 2, 3, 5, 6 and 8 to 83 for use in a method of reducing the virus titers in lungs in a food producing animal of need, in comparison to a food producing animal of a non-immunized control group of the same species, the method comprising administering to the food producing animal a therapeutically effective amount of said immunogenic composition or DIVA vaccine.

95. The immunogenic composition or a DIVA vaccine according to any one of clauses 2, 3, 5, 6 and 8 to 83 for use in a method of vaccinating a food producing animal of need having anti-Swine Influenza A virus antibodies, the method comprising administering to the food producing animal a therapeutically effective amount of said immunogenic composition or DIVA vaccine.

96. The immunogenic composition or a DIVA vaccine according to any one of clauses 2, 3, 5, 6 and 8 to 83 for use in a method of providing maternally derived immunity against Influenza A virus in a young food producing animal comprising administering to the mother of said young food producing animal a therapeutically effective amount of said immunogenic composition or DIVA vaccine while said mother is pregnant with said young food producing animal.

97. The immunogenic composition or a DIVA vaccine according to any one of clauses 2, 3, 5, 6 and 8 to 83 for use in a method of providing increased protection against Influenza A virus infection in a young food producing animal of need, wherein (a) the mother of said young food producing animal is to be vaccinated with a therapeutically effective amount of an immunogenic composition or DIVA vaccine according to any one of clauses 2, 3, 5, 6 and 8 to 83 while said mother is pregnant with said young food producing animal and/or (b) said young food producing animal is to be vaccinated with a therapeutically effective amount of said immunogenic composition or DIVA vaccine within three weeks of age.

98. The method or use of any one of clauses 86 to 97, wherein the food producing animal is swine, piglet or sow.

99. The method or use of any one of clauses 86 to 98, wherein the Influenza A virus is swine Influenza A virus.

100. The method or use of any one of clauses 86 to 99, wherein the immunogenic composition or DIVA vaccine is administered once.

101. The method or use of any one of clauses 86 to 100, wherein the immunogenic composition or DIVA vaccine is administered to the food producing animal within the first six weeks of age, within the first two weeks of age, within the first week of age or within the first day of age.

102. The method or use of any one of clauses 86 to 101, wherein the immunogenic composition or DIVA vaccine is administered at two doses.

103. The method or use of clause 102, wherein the immunogenic composition or DIVA vaccine is administered to the food producing animal within the first week of age and a second time within the second, third or fourth week of age.

104. The method or use of any one of clauses 86 to 103, wherein said immunogenic composition or DIVA vaccine is administered intramuscular or intranasal.

105. The method or use of any one of clauses 86 to 88 and 92 to 94 and 98 to 104, wherein the food producing animal is anti-Swine Influenza A virus antibody negative.

106. The method or use of any one of clauses 86 to 104, wherein the food producing animal is anti-Swine Influenza A virus antibody positive.

107. The method or use of any one of clauses 86 to 106, wherein the immunogenic composition or DIVA vaccine comprises $1\times10^4$ to $1\times10^7$ $TCID_{50}$ of the EHV vector.

108. The method or use of any one of clauses 86 to 107, wherein said method results in an improvement in an efficacy parameter selected from the group consisting of: a reduction in weight loss, a lower virus load in lungs, a reduction in lung lesions, a reduced and/or shortened shedding of virus, a reduced rectal temperature, reduced clinical symptoms (in particular respiratory symptoms), increased induction of (neutralizing) anti-Swine Influenza A virus antibodies, increased stimulation of T-cells against Swine Influenza A virus, increased stimulation of B-cells against Swine Influenza A virus, and a reduction of proinflammatory cytokines, e.g. IL1β, in lungs, or combinations thereof, in comparison to a food producing animal of a non-immunized control group of the same species.

109. The method or use of any one of clauses 86 to 108, wherein the treatment or prophylaxis results in shortening of the virus load phase as compared to a food producing animal of a non-treated control group of the same species.

110. The method or use of any one of clauses 86 to 109, wherein the treatment or prophylaxis results in a reduction of the shedding of the Influenza A virus from day 1 after challenge (infection).

111. The method or use of any one of clauses 86 to 110, wherein the immunogenic composition or DIVA vaccine protects against a homologous and/or heterologous challenge with an Influenza A virus.

112. The method or use of any one of clauses 86 to 111, wherein the immunogenic composition or DIVA vaccine protects against a challenge with an Influenza A virus of serotypes H1 and/or H3.

Swiss Type and Other Wordings

113. The EHV vector, the immunogenic composition or the DIVA vaccine of any one of clauses 2, 3, 5, 6 and 8 to 83 for therapeutic use.

114. The EHV vector, the immunogenic composition or the DIVA vaccine of any one of clauses 2, 3, 5, 6 and 8 to 83 for use as an immunogen or vaccine.

115. The EHV vector, the immunogenic composition or the DIVA vaccine of any one of clauses 2, 3, 5, 6 and 8 to 83 for use as a medicament.

116. Use of the EHV vector, the immunogenic composition or the DIVA vaccine of any one of clauses 2, 3, 5, 6 and 8 to 83 for the manufacture of a medicament.

117. Use of the EHV vector, the immunogenic composition or the DIVA vaccine of any one of clauses 2, 3, 5, 6 and 8 to 83 for the treatment and/or prophylaxis of Swine Influenza A virus infections in a food producing animal.

DIVA

118. A method of differentiating food producing animals infected with Swine Influenza A virus from food producing animals vaccinated with the immunogenic composition or the DIVA vaccine of anyone of clauses 2, 3, 5, 6 and 8 to 83, comprising (a) obtaining a sample from an food producing animal, and (b) analyzing said sample in an immuno test and/or genomic analytical test.

119. The method according to clause 118, wherein the immuno test comprises testing whether the sample comprises antibodies specifically recognizing the N (neuraminidase) protein or NP (nucleoprotein) protein of swine influenza.

120. The method according to clause 118 or 119, wherein the food producing animal is infected with Swine Influenza A virus if antibodies specifically recognizing the N (neuraminidase) protein or NP (nucleoprotein) protein of swine influenza have been detected.

121. The method according to clause 118, wherein the genomic analytical test comprises testing whether the sample comprises Swine Influenza A virus specific sequences encoding N (neuraminidase) and/or NP (nucleoprotein).

122. The method according to clause 118 or 121, wherein the food producing animal is infected with Swine Influenza A virus if Swine Influenza A virus specific sequences encoding N (neuraminidase) and/or NP (nucleoprotein) have been detected.

123. The method according to any one of clause 118 to 122, wherein the immuno test is an EIA (enzyme immunoassay) or ELISA (enzyme linked immunosorbent assay), or, wherein the genomic analytical test is a PCR (polymerase chain reaction), RT-PCR (reverse transcriptase polymerase chain reaction) or real time PCR (polymerase chain reaction).

124. The method according to any one of clause 118 to 123, wherein the food producing animal is swine.

125. The method according to any one of clause 118 to 124, wherein the sample is a serum sample.

126. The method according to any one of clause 118 to 125, wherein the ELISA is the ELISA is an indirect ELISA, Sandwich ELISA, a competitive ELISA or blocking ELISA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Plasmid map and nucleotide sequence of transfer plasmid pU-mC70-BGH

FIG. 3. qPCR results of a promoter kinetics experiment. The graph in 3, A shows the kinetics of the transcription of orf72, encoding for the essential glycoprotein D. These data were used to normalize the data of the transcription kinetics of mCherry (graph in 3, B).

FIG. 5. Plasmid map and nucleotide sequence of transfer vector pU70-p455-71 K71

FIG. 6. Plasmid map and nucleotide sequence of the transfer plasmid pU70-p455-H3-71 K71 for insertion of the expression cassette p455-H3-71 into orf70 of EHV-1 RacH, H3=open reading frame encoding for Influenza A virus hemagglutinin H3, 71pA=new polyA sequence as described in invention disclosure EM P2016-022, I-SceI=cleavage site for the restriction endonuclease I-SceI, promoter aph=prokaryotic Kanamycin resistance gene promoter, Kana=Kanamycine resistance gene, 3' end ORF70=recombination region downstream of insertion site, ORI=origin of replication of the plasmid, $AP_r$=Ampicillin resistance gene of the plasmid, upstream orf70=recombination region upstream of insertion site p455=new promoter p455, bp=base pairs.

FIG. 10. Virus Titers: Mean lung titers of groups one and three days after challenge for individual animals (A) or for group means (B). Titers are given as tissue culture infectious dose 50 of Swine IAV per g lung homogenate, respectively. Titers were determined as means of values determined for the left and right lungs per animal, respectively, and investigating a homogenate per lung that was derived from a pool of three lung samples, respectively. Negative control group (neg. ctrl.), challenge control group (chall. ctrl.), animals vaccinated once with RacH-SE-70-p455-H3 (1×EHV-1), vaccinated twice with RacH-SE-70-p455-H3 (2×EHV-1), or twice with commercially available inactivated Swine IAV vaccine (2× Inact.).

FIG. 11. Plasmid map and nucleotide sequence of transfer vector pU-1-3-p430-BGHKBGH.

FIG. 12. Plasmid map and nucleotide sequence of the transfer plasmid pU1/3-p430-H1av-BGH_K_BGH for insertion of the expression cassette p430-H1av-BGH into orf1/3 of EHV-1 RacH. H1av=open reading frame encoding for Influenza A virus hemagglutinin H1, BGHpA=bovine growth hormone polyA sequence, promoter aph=prokaryotic Kanamycin resistance gene promoter, Kana=Kanamycine resistance gene, Flank B=recombination region downstream of insertion site, Flank A=recombination region upstream of insertion site, p430=new promoter p430, bp=base pairs.

FIG. 22. Schematic map of transfer plasmid pU1/3-p430-H1hu-BGHKBGH.

FIG. 23: Schematic map of transfer plasmid pU70-p455-H1pdm-71 K71.

Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GraphPad Prism® for Windows software 7.02, GraphPad Software, Inc., La Jolla, Calif. 92037, USA, using standard software settings, respectively.

Figure 30:
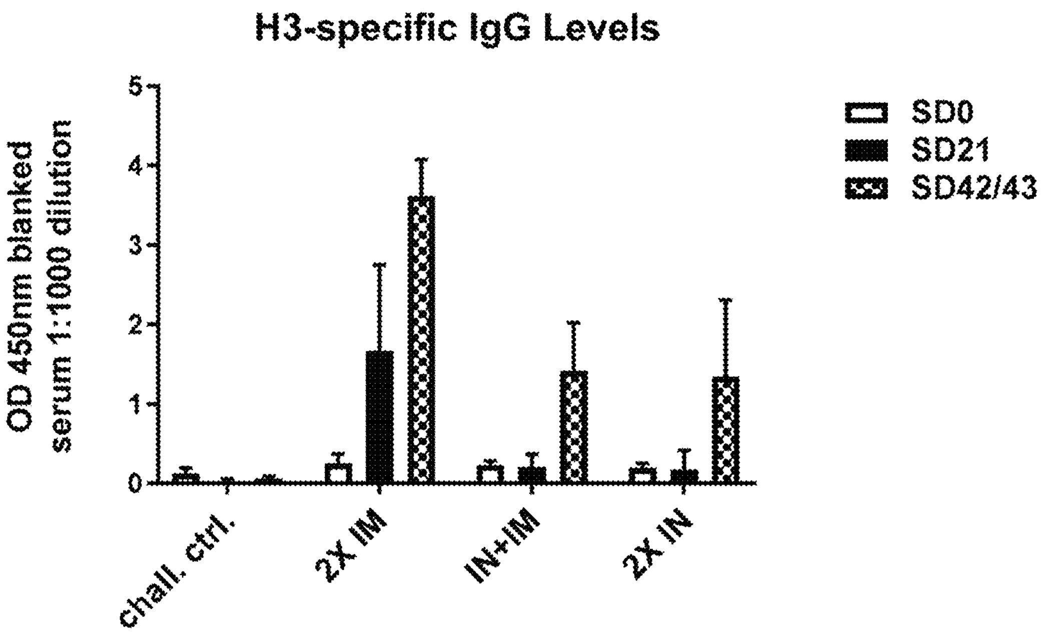

FIG. 30: Results from an enzyme-linked immunosorbent assay (ELISA) specific for swine immunoglobulin G (IgG) directed against a recombinantly expressed swine IAV hemagglutinin H3 antigen being homologous to the H3 expressed by vaccine strain rEHV-1 RacH-SE_B. For the test, each well was coated with 100 ng of recombinantly expressed H3. Samples were measured pairwise, sample means calculated from pairwise measurements, and group values were calculated from sample means, respectively. chall. ctrl., challenge control group (served as negative control); 2×IM, group vaccinated two times intramuscularly; IN+IM, group vaccinated first intranasally and second intramuscularly; 2×IN, group vaccinated two times intranasally. Error bars indicate standard deviations. Study days (SD) are indicated in the legend to the right of the graph.

Figure 31:
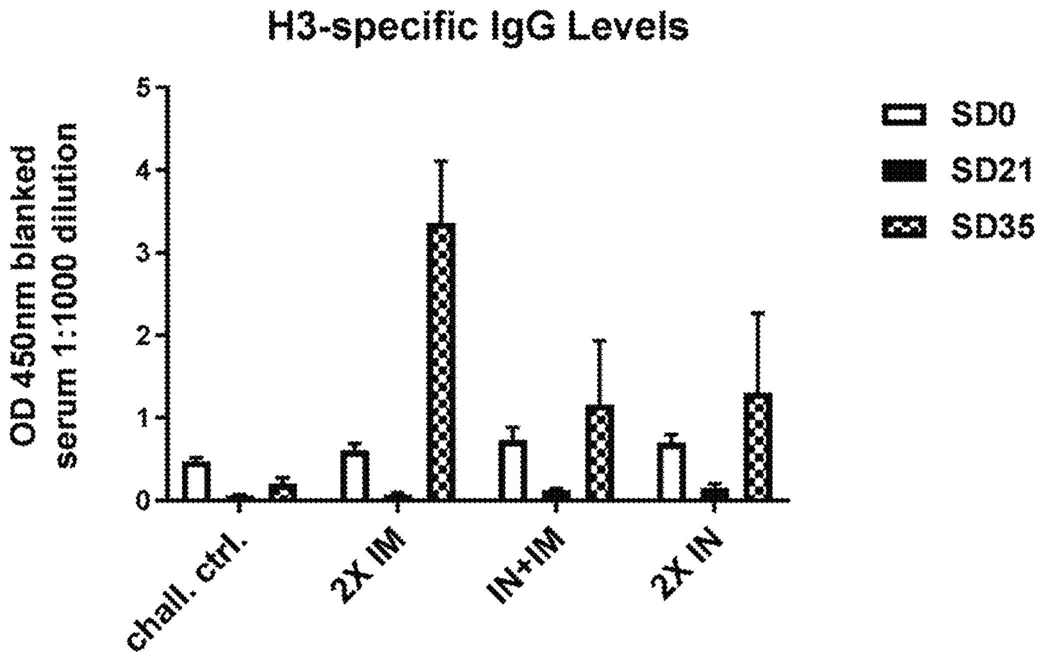

FIG. 31: Results from an enzyme-linked immunosorbent assay (ELISA) specific for swine immunoglobulin G (IgG) directed against a recombinantly expressed swine IAV hemagglutinin H3 antigen being homologous to the H3 expressed by vaccine strain rEHV-1 RacH-SE_B. For the test, each well was coated with 100 ng of recombinantly expressed H3. Samples were measured pairwise, sample means calculated from pairwise measurements, and group values were calculated from sample means, respectively. chall. ctrl., challenge control group (served as negative control); 2×IM, group vaccinated two times intramuscularly; IN+IM, group vaccinated first intranasally and second intramuscularly; 2×IN, group vaccinated two times intranasally. Error bars indicate standard deviations. Study days (SD) are indicated in the legend to the right of the graph.

Figure 32:
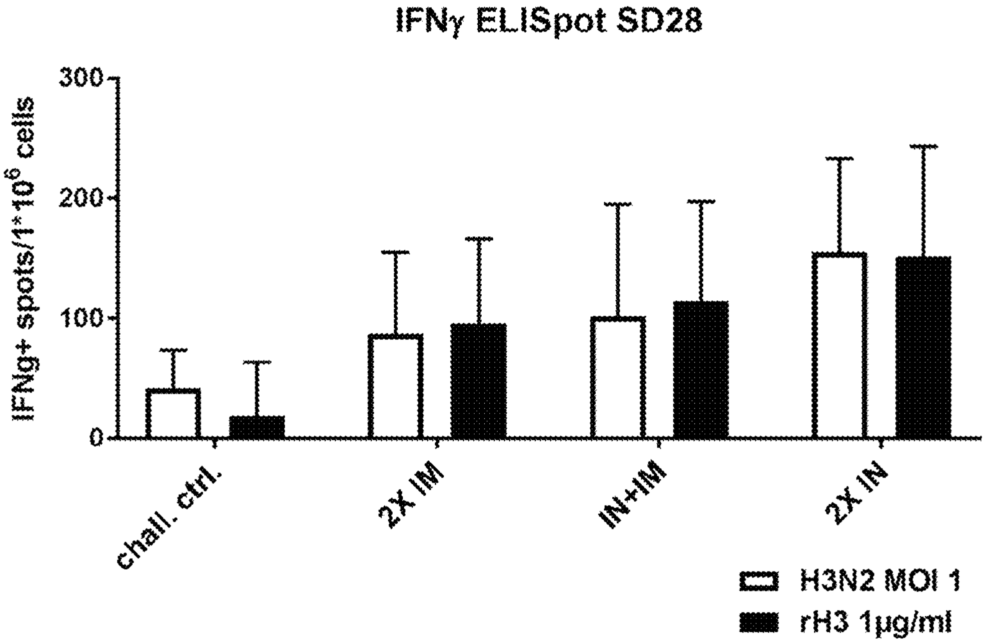

FIG. 32: Results from interferon gamma-specific enzyme-linked immunosorbent spot assay (IFNγ ELISpot). Peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 μg/ml (rH3 1 μg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively. chall. ctrl., challenge control group (served as negative control); 2×IM, group vaccinated two times intramuscularly; IN+IM, group vaccinated first intranasally and second intramuscularly; 2×IN, group vaccinated two times intranasally. Error bars indicate standard deviations.

Figure 33:
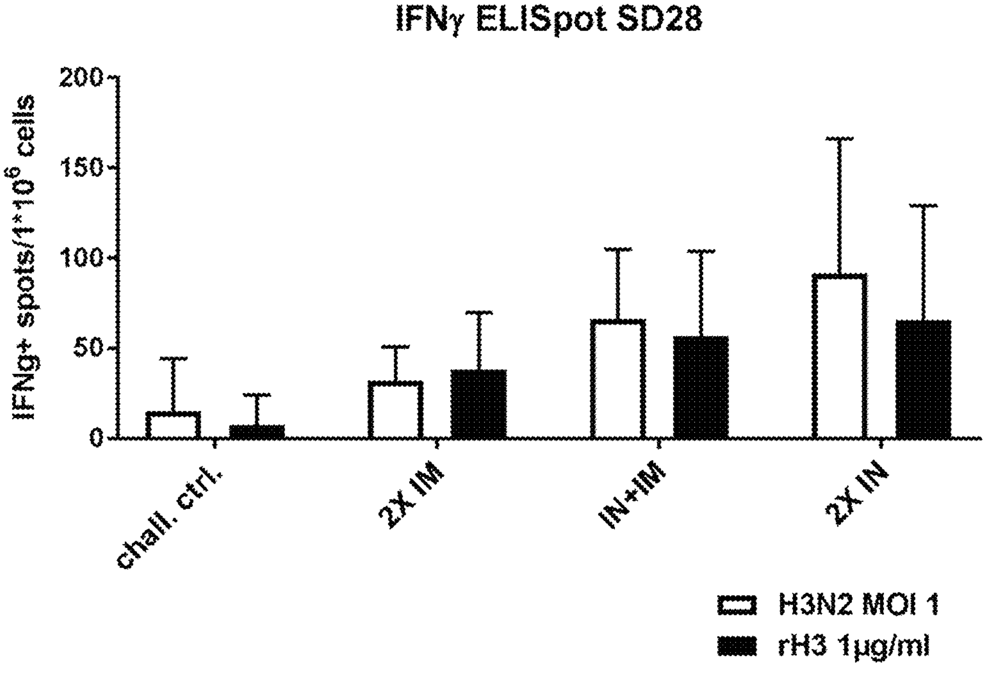

FIG. 33: Results from interferon gamma-specific enzyme-linked immunosorbent spot assay (IFNγ ELISpot). Peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 μg/ml (rH3 1 μg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively. chall. ctrl., challenge control group (served as negative control); 2×IM, group vaccinated two times intramuscularly; IN+IM, group vaccinated first intranasally and second intramuscularly; 2×IN, group vaccinated two times intranasally. Error bars indicate standard deviations.

Figure 34:
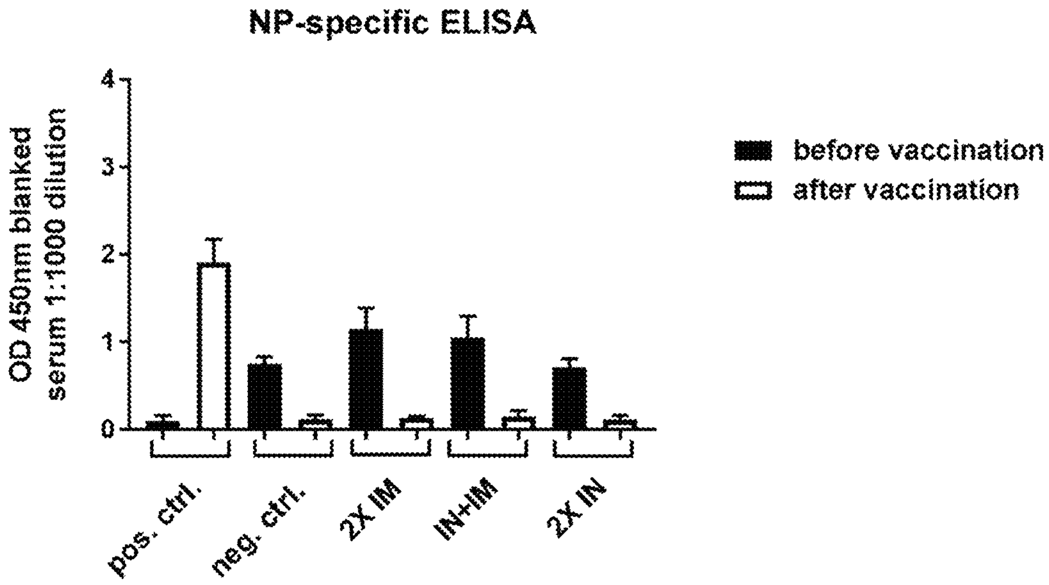

FIG. 34: Results from an enzyme-linked immunosorbent assay (ELISA) specific for swine immunoglobulin G (IgG) directed against a recombinantly expressed swine IAV nucleoprotein (NP). For the test, each well was coated with 100 ng of recombinantly expressed NP. Samples were measured pairwise, sample means calculated from pairwise measurements, and group values were calculated from sample means, respectively. pos. ctrl., positive control group; neg. ctrl., negative control group; 2×IM, group vaccinated two times intramuscularly;IN+IM, group vaccinated first intranasally and second intramuscularly; 2×IN, group vaccinated two times intranasally. Error bars indicate standard deviations. Study days (SD) are indicated in the legend to the right of the graph.

SEQUENCES OVERVIEW

The following sequences are detailed and disclosed hereby in the present invention:

Promoters:

SEQ ID NO: 1 EHV-4 600 bp desoxyribonucleic acid sequence 4pgG600

SEQ ID NO: 2 EHV-4 600 bp desoxyribonucleic acid sequence 4pMCP600

SEQ ID NO: 3 EHV-4 430 bp desoxyribonucleic acid sequence p430

SEQ ID NO: 4 EHV-4 449 bp desoxyribonucleic acid sequence p455

SEQ ID NO: 5 primer no 1130 specific for orf72

SEQ ID NO: 6 primer no 1131 specific for orf72

SEQ ID NO: 7 primer no. 1079 specific for mCherry

SEQ ID NO: 8 primer no. 1080 specific for mCherry

Insertion site:

SEQ ID NO: 9 Artificial sequence nucleic acid PCR primer 1017 for the orf70 insertion region SEQ ID NO: 10 Artificial sequence nucleic acid PCR primer 1018 for the orf70 insertion region SEQ ID NO: 11 Artificial sequence nucleic acid PCR primer 1007 for the orf1/3 insertion region SEQ ID NO: 12 Artificial sequence nucleic acid PCR primer 1008 for the orf1/3 insertion region SEQ ID NO: 13 left (Up70) flanking region (417 bp)

SEQ ID NO: 14 right (Up71 ) flanking region (431 bp)

SEQ ID NO: 15 flanking region left (up orf70) in the wild-type EHV-1 strain ab4 (Genbank accession number AY665713.1), located at nucleotides 127264-127680

SEQ ID NO: 16 flanking region right (up orf71 ) in the wild-type EHV-1 strain ab4 (Genbank accession number AY665713.1), located at nucleotides 128484-128913

SEQ ID NO: 17 truncated flanking region in the RED system: left (Up70) flanking region (283 bp)=identical to the 3' 283 bp of the 417 bp "classical" flanking region SEQ ID NO: 18 truncated flanking region in the RED system: right (Up71 ) flanking region (144 bp)=identical to the 5' 144 bp of the 431 bp "classical" flanking region SEQ ID NO: 19 Deleted portion in the wild-type ab4 (Genbank accession number AY665713.1) genome sequence, nt 127681-128482

SEQ ID NO: 20 Deleted portion in the RacH genome sequence (no nt numbers available because complete genome sequence not known)

Plasmid/Vector Sequences:

SEQ ID NO: 21 Nucleotide sequence of transfer plasmid pU-mC70-BGH

SEQ ID NO.: 22 Nucleotide sequence of transfer vector pU70-p455-71 K71

SEQ ID NO.: 23 Nucleotide sequence of transfer plasmid pU70-p455-H3-71 K71

SEQ ID NO.: 24 Nucleotide sequence of transfer vector pU-1-3-p430-BGHKBGH

SEQ ID NO.: 25 Nucleotide sequence of transfer plasmid pU1-3-p430-H1av-BGHKBGH

Hemagglutinin Sequences

SEQ ID NO:26 hemagglutinin [Influenza A virus (A/swine/Italy/116114/2010(H1N2))] GenBank: ADR01746.1 H1pdm SEQ ID NO:27 hemagglutinin [Influenza A virus (A/swine/Italy/7680/2001(H3N2))] GenBank: ABS50302.2 H3:

SEQ ID NO:28 hemagglutinin [Influenza A virus (A/swine/Gent/132/2005(H1N1))] GenBank: AFR76623.1 H1av:

SEQ ID NO:29 hemagglutinin [Influenza A virus (A/swine/Italy/4675/2003(H1N2))] GenBank: ADK98476.1* H1hu

*Amino acid 531 (X, stop codon, was changed to I):

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Establishment of the New Insertion Site ORF70

Figure 1A:
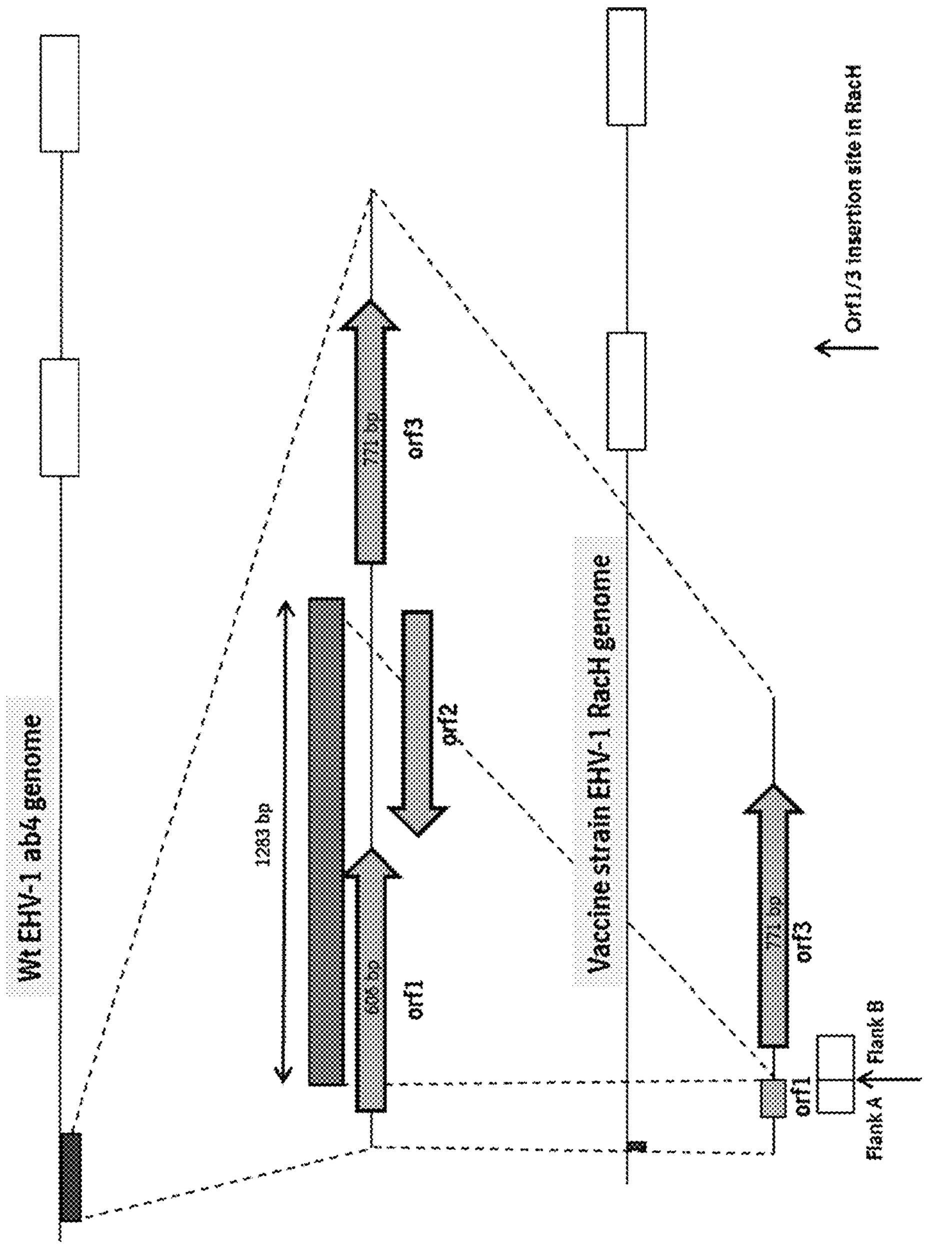
FIG. 1A Schematic illustration comparing the orf1/3 regions of wild-type (wt) EHV-1 strain ab4 and attenuated vaccine strain EHV-1 RacH FIG. 1B. Schematic drawing of the orf70 insertion site: UL=long unique segment, US=short unique segment, IR=inner inverted repeat, TR=terminal inverted repeat, gG=glycoprotein G, gpII=glycoprotein II, orf=open reading frame, bp=base pairs.
Figure 1B:
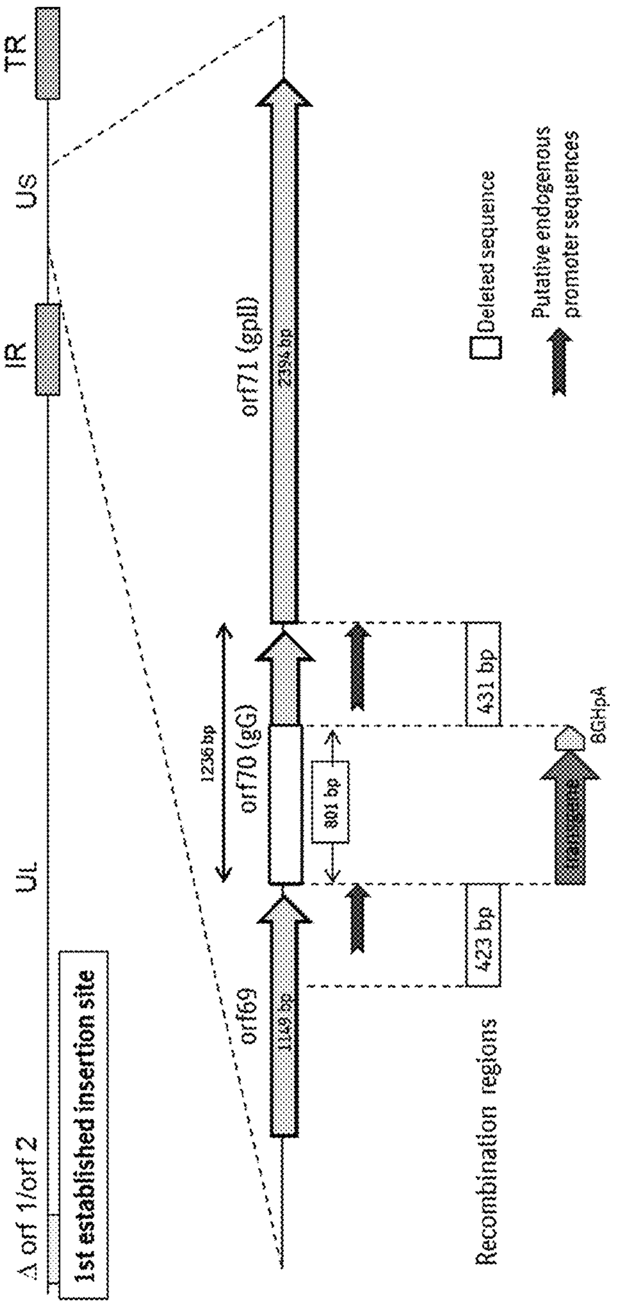

In order to augment the capabilities of the EHV-1 vector the inventors sought to find a way to express two different transgenes from one vector backbone without coupling two transgenes by RNA-virus-derived functions under control of one promoter. The inventors hypothesized that the herpesvirus genome would tolerate the use of two independent transgene insertion sites in parallel. To determine whether the EHV-1 ORF70 was a suitable transgene insertion site, 801 basepairs of the 5' end of orf70 (1236 bp) were replaced with an expression cassette coding for the autofluorescent mCherry protein (Shaner et al. 2004) by classical homologous recombination (FIG. 1B). A map of the plasmid pU-mC70-BGH is in FIG. 2 (SEQUENCE ID NO. 21). The DNA fragment used for homologous recombination was excised from pU-mC70-BGH with XbaI. The gel-purified fragment was co-transfected with viral genomic DNA of EHV-1 RacH into RK13 cells. Efficient rescue of recombinant vector virus and efficient replication in cultured cells were shown by live fluorescence and virus titrations (not shown). Deletion of two thirds of orf70 had the additional benefit that expression of glycoprotein G encoded by orf70 was abolished. Glycoprotein G of EHV-1 was shown to be a non-structural, secreted chemokine binding protein counter-acting the host's immune response (Drummer et al., 1998; Bryant et al., 2003). Since a vector vaccine is intended to stimulate the vaccine's immune response, removal of this particular immunosuppressive function of the viral vector might additionally improve performance of the viral vector platform EHV-1 RacH-SE.

Example 2

Identification and Construction of New Promoters

The strategy to identify suitable promoter sequences was as follows: 600 bp fragments of the EHV-4 sequence upstream of two known orfs were analyzed first by aligning them with the respective sequence fragments of the EHV-1 genome. The genes chosen were orf42 encoding the major capsid protein (MCP), and orf70 encoding glycoprotein G (gG). The major capsid protein is one of the most abundant constituents of the virion and needed for assembly of capsids in the cell nucleus as soon as newly synthesized viral DNA is ready for packaging. Its promoter is therefore expected to be active during early and late times in the viral replication cycle. For glycoprotein G it is known that its gene (orf70) is active also during early and late times in the replication cycle (Colle et al. 1995, Drummer et al. 1998). Sequence identity was 82.2% for the putative MCP-promoter and 82.3% for the putative gG-promoter. These differences were considered large enough to prevent homologous recombination on the one hand, and small enough to allow for transcriptional activation during EHV-1 replication on the other hand. In order to test for promoter activity, the 600 bp DNA fragments 4pgG600

(SEQ ID NO: 1)

```
GCAGACTTTGGAGCAGCACAATTTCCGGTTGTGGACCCCATGGACCTTG
GTTTGGCTGGTACCGTGGAAACTAACGCTCCGGAAGTTTTGGCCAGAGCA
AAATACAATTCGAAGGTAGACATATGGAGCGCCGGAATAGTTCTGTTTGA
AATGCTCGCATATCCATCAACTCTATTTGAGGACCCGCCGAGTACCCCAC
AAGAGTATGTAAAAAGCTGTCATTCTCAACTACTGAGAATAATATCAAAG
CTAAAGATAAACCCTGAGGAGTTTCCACGGGAACCAGAGTCTAGGCTCGT
GCGCGGATACATCGAATACGCCAGCCTAGAGCGTAAGCCACATACGCGCT
ATCCTTGCTTCCAGCGCGTGAACCTACACATTGACGGGGAATTTTTGATC
CATAAAATGCTAGCGTTCAATGCTGCGATGCGCCCATCCGCAGAAGAGTT
GTTGTCCTACCCAATGTTTATGAATCTGTAGGATGACTAACAGATTTGGG
GTGGAGACGGCGTGGGCGATACTGTATAAAGTTGTACTACTTACCAGCCC
AGTCAGTGTGCTGTAGTGCCACCACCTGTAAAGCTGTGATAAGCTGCAGT
T
```

and 4pMCP600

(SEQ ID NO: 2)

```
AGCTGGGGGAGTTTGTACTATAGTGTATTACATGCGGCTTGCAATAACT
GCCTGGTTTATGTTTCGCAACATTCAAGCAGACATGCTACCGCTAAACA
```

-continued

```
CTTTGCAACAATTTTTTATTGGGTGTTTGGCCTTTGGTAGAACTGTCGC
GTTTTTGGTGGTAGCATATACTACCTTATTTATACGCTCCGAGCTGTTT
TTCAGCATGCTAGCACCCAACGCCGAGCGAGAGTATATAACTCCCATCA
TTGCCCACAAGCTTATGCCACTTATTAGCGTCCGCTCTGCCGTTTGCTT
AGTCATAATATCTACCGCCGTTTACGCAGCAGACGCTATCTGCGACACA
ATTGGATTTGCGATACCGCGCATGTGGATGTGTATTTTAATGAGATCAA
CCTCCATGAAGCGTAACTAGGGGGCCTCCCACTGAGGCACTACCGGCTT
AGCAGCTGACTAACACAGTATAAAACGTGAGAAGAAATCAGTCTCATGC
GCCATTAGCGCTAGGCTAGTTAGCGTGGAGGACCGGAGCGCTACCGCCA
GCAGTTTCATCCGCCTGGTTACGGGTTTGTTAACACCTACCGGTGTTTT
ACCGCTACCATA
```

were synthesized and cloned upstream of a reporter gene encoding the autofluorescent protein mCherry (Shaner et al., 2004). As transcription termination signal and mRNA stabilizing function the bovine growth hormone polyadenylation sequence (BGHpA; Goodwin & Rottman, 1992) was cloned directly downstream at the 3' end of the reporter gene.

To be used as a positive control the CMV promoter was amplified from the commercially available plasmid pcDNA3.1 (Invitrogen) and cloned upstream of the mCherry reporter gene, here also the BGHpA was added at the 3' end of the reporter gene. Cell cultures were transfected with the three plasmids (pBlu-4pgGmCherry, pBlu-4pMCPmCherry, and pBlu-CMVmCherry) and inspected by fluorescence microscopy for mCherry fluorescence. Strong activity of the CMV promoter was obvious at different times after transfection. The 4pgG600 promoter was also active after transfection, activity of the 4pMCP600 promoter was also detectable, but weak in comparison with the 4pgG600 promoter and even more so when compared with the CMV-promoter even three days after transfection.

In order to investigate the effect of viral gene products on promoter activity, cell cultures transfected with either pBlu-4pgG600-mCherry or pBlu-4pMCP600-mCherry were superinfected one day after transfection with the green fluorescent EHV-1 RacHI-EF. The viral gene products obviously transactivated the 4pMCP600 promoter to significantly higher activity than in the absence of EHV-1 RacHI-EF replication. The effect was also present in cell cultures transfected with pBlu-4pgG600-mCherry and superinfected with EHV-1 RacHI-EF, albeit not so drastic since the initial activity in the absence of viral replication was higher than observed for pBlu-4pMCP600-mCherry. Still, for both 600 bp promoters a transactivating effect of viral replication on their activities in cell cultures was demonstrated.

This effect might be explained if the 600 bp sequences contain repressor elements, which are normally located upstream of the activator elements. Consequently, a shorter promoter might be more active in the absence of viral gene products. To test this both EHV-4 promoter sequences were truncated to approximately 75% of their original lengths and tested again.

In particular the 600 bp promoters were truncated to 430 bp for 4pgG, new name: p430:

(SEQ ID NO: 3)

```
TCTATTTGAGGACCCGCCGAGTACCCCACAAGAGTATGTAAAAAGCTGTC
ATTCTCAACTACTGAGAATAATATCAAAGCTAAAGATAAACCCTGAGGAG
TTTCCACGGGAACCAGAGTCTAGGCTCGTGCGCGGATACATCGAATACGC
CAGCCTAGAGCGTAAGCCACATACGCGCTATCCTTGCTTCCAGCGCGTGA
ACCTACACATTGACGGGGAATTTTTGATCCATAAAATGCTAGCGTTCAAT
GCTGCGATGCGCCCATCCGCAGAAGAGTTGTTGTCCTACCCAATGTTTAT
GAATCTGTAGGATGACTAACAGATTTGGGGTGGAGACGGCGTGGGCGATA
CTGTATAAAGTTGTACTACTTACCAGCCCAGTCAGTGTGCTGTAGTGCCA
CCACCTGTAAAGCTGTGATAAGCTGCAGTT
```

and to 449 bp for 4pMCP, new name: p455:

(SEQ ID NO: 4)

```
TTGGTGGTAGCATATACTACCTTATTTATACGCTCCGAGCTGTTTTTCAG
CATGCTAGCACCCAACGCCGAGCGAGAGTATATAACTCCCATCATTGCCC
ACAAGCTTATGCCACTTATTAGCGTCCGCTCTGCCGTTTGCTTAGTCATA
ATATCTACCGCCGTTTACGCAGCAGACGCTATCTGCGACACAATTGGATT
TGCGATACCGCGCATGTGGATGTGTATTTTAATGAGATCAACCTCCATGA
AGCGTAACTAGGGGGCCTCCCACTGAGGCACTACCGGCTTAGCAGCTGAC
TAACACAGTATAAAACGTGAGAAGAAATCAGTCTCATGCGCCATTAGCGC
TAGGCTAGTTAGCGTGGAGGACCGGAGCGCTACCGCCAGCAGTTTCATCC
GCCTGGTTACGGGTTTGTTAACACCTACCGGTGTTTTACCGCTACCATA.
```

mCherry-reporter plasmids containing the shortened promoters were transfected in cell cultures and inspected by fluorescence microscopy. While the p430 activity was comparable to that of the 600 bp version (4pgG600), the activity of the p455 was significantly increased over the activity of the 4pMCP600. This result was in accordance with the results of the transfection/superinfection experiments using the 600 bp versions of the two promoters, namely, that presence of EHV-1 replication in the same cell provided a mechanism of transactivation of the 4pMCP600 promoter increasing its activity strongly while the transactivation of the 4pgG600 promoter was visible but less pronounced.

In addition to two new promoters also a new polyA sequence was needed for expression from the new orf70 insertion site. The element is called 71 pA. Its nucleotide sequence was synthesized and cloned downstream of the mCherry orf in a transfer plasmid containing the p455 targeted for the orf70 insertion site in pRacH-SE.

Next, rEHV-1 RacH-SE were generated to assay promoter activities in the background of viral replication (Table 1). The two EHV-4 promoters (p430 and p455), the CMV promoter and the mouse cytomegalovirus IE1 promoter (MCMV) were used to direct expression of mCherry in combination with a BGH polyA signal to increase mRNA stability. The MCMV IE1 promoter (enhancer) as described by Dorsch-Häsler et al. (1985) was synthesized and cloned in a plasmid vector from which it was subcloned into the transfer plasmid. In addition, the p455 was also cloned into the new insertion site in orf70 driving expression of mCherry in combination with the new polyA signal 71 pA. As another control rEHV-1 RacHmC70 was included in the experiments. Cells infected with this recombinant virus express mCherry under control of the endogenous gG promoter (egGp) (Table 1)

TABLE 1

| | Orf1/3 insertion site | | | Orf70 insertion site | | |
|---|---|---|---|---|---|---|
| name | promoter | reporter | polyA | Promoter | reporter | polyA |
| 1/3-CMV-mC | HCMV IE1 | mCherry | BGH | none | none | none |
| 1/3-MCMV-mC | MCMV IE1 | mCherry | BGH | none | none | none |
| 1/3-p455-mC | p455 | mCherry | BGH | none | none | none |
| 1/3-p430-mC | p430 | mCherry | BGH | none | none | none |
| 70-egGp-mC | none | none | none | endogenous gG | mCherry | BGH |
| 70-p455-mC | none | none | none | p455 | mCherry | 71pA |

VERO or PK/WRL cells were infected with all six mCherry expressing viruses at a m.o.i. (multiplicity of infection) of 1. Infected cells were collected at 0, 4, 8, and 12 hours p.i. and total RNA was prepared. Viral and cellular genomic DNA contaminating the RNA preparations was destroyed by DNAse I digestion. Integrity of the RNA and removal of viral DNA was shown by reverse transcription with and without addition of reverse transcriptase followed by PCR with a primer pair specific for orf72 (primers no 1130/1131, (TGTCTACCTTCAAGCTTATG (SEQ ID NO:5)/CTAGCGCAGTCGCGTTG (SEQ ID NO:6)) encoding the essential structural glycoprotein D of EHV-1. The expected 196 bp PCR product was amplified only from reverse transcribed samples (cDNA) where reverse transcriptase had been added, specifically the samples prepared at t1=4 h p.i., t2=8 h p.i., and t3=12 h p.i., not from the samples prepared at t0=0 h p.i. All samples where reverse transcriptase had not been added to the reaction did not produce any PCR product as expected. Thus it was shown that the samples (cDNA) that would be used as templates for qPCR did not contain viral genomic DNA.

The cDNAs obtained from the reverse transcription with added enzyme were then analyzed by qPCR using a primer pair specific for mCherry (primers no. 1079/1080, (GCGAGGAGGATAACATGG (SEQ ID NO:7)/ACCCTTGGTCACCTTCAG (SEQ ID NO:8)) and the orf72 primer pair 1130/1131 (TGTCTACCTTCAAGCTTATG (SEQ ID NO:5)/CTAGCGCAGTCGCGTTG (SEQ ID NO:6)). Ct (cycle threshold) values for the orf72 qPCR were used to assess comparability of the different virus infections run in parallel and to normalize the Ct values for the mCherry qPCR. Thus, transcription of mCherry was quantified relative to the time after infection and to the different viruses (FIG. 3).

As shown FIG. 3A Ct values for orf72 transcripts were nearly identical for the six different viruses at the four different times after infection. Ideally all six viruses would produce identical values at the times investigated and only one line would be visible. Nearly identical lines confirmed sufficient quality of the experiment, also the 12 h p.i. (post-infection) time results are valid because the decrease as compared to 8 h p.i. indicates a further increase in the number of transcripts which is only possible when the replication has not yet passed its maximum. The statistical average of each time p.i. was calculated. The value of each virus at a certain time was divided by the average calculated for that time and used as a factor which with the Ct values of the mCherry qPCR were normalized to make them directly comparable. Normalized Ct values of the mCherry qPCR are graphically shown in the right graph in FIG. 3*b*. Divergence of the lines indicates differences in the numbers of mCherry transcripts produced in the different virus-infected cells.

Figure 4:
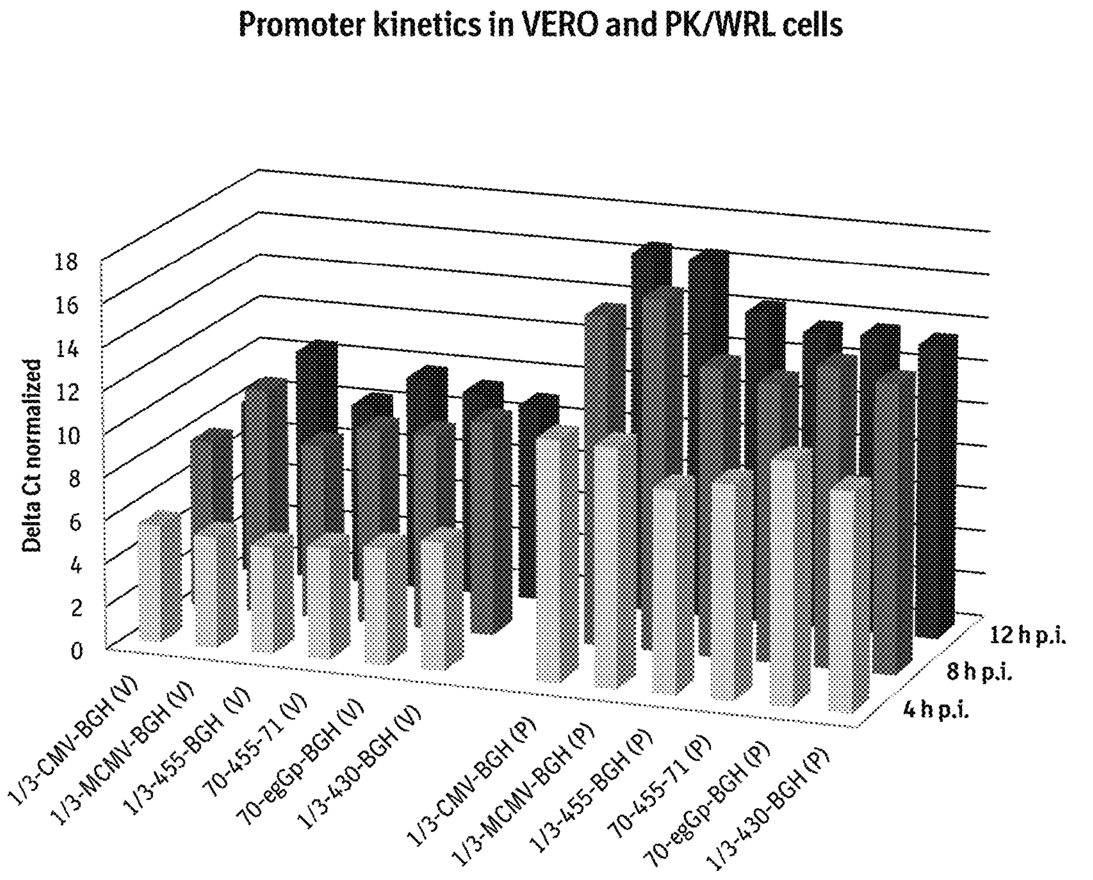
FIG. 4. qPCR results of two independent promoter kinetics experiments: Positive correlation of transcription activity and value depicted. Normalized Ct values of mCherry qPCR results at the different times after infection were subtracted from the corresponding average Ct value at t=0. Two experiments in two different cell lines are shown.

In a different type of graph two experiments, one using VERO-EU cells (V) and one using PK/WRL cells (P) were combined (FIG. 4). Quality of the RNA preparations and the viral replication over time was confirmed as described above by reverse transcription with and without reverse transcriptase followed by PCR with the orf72 primers. qPCR Ct values obtained for mCherry were normalized as described above on the basis of the qPCR Ct values for orf72. Normalized Ct values of t1=4 h p.i.; t2=8 h p.i., and t3=12 h p.i. were subtracted from the normalized Ct values at t0 (Delta normalized Ct) resulting in a positive correlation with transcription activity.

Although the two experiments in VERO (V) or PK/WRL (P) cells cannot directly be compared, the higher expression levels in PK/WRL cells most likely reflect the superior permissivity of PK/WRL cells for EHV-1 replication which routinely results in ten times higher titers of infectious virus. While activities of the EHV-derived promoters p430, p455 and egGp are almost the same at the respective times p.i. for the used cell line, irrespective of their insertion site or the used poly A (BGH or 71 pA), activities of the CMV- and MCMV promoters are higher in the PK/WRL cells. In VERO-EU cells, only the MCMV promoter was shown to have higher activity, the CMV promoter was not superior to the EHV-promoters.

From these experiments it was concluded that the EHV-4 promoters p430 and p455 were suitable to be used in the EHV-1 RacH backbone to drive expression of inserted transgenes from both the orf1/3 and the orf70 insertion sites.

Example 3

Use of the New p455 Promoter in Recombinant EHV-1 Vector Vaccines and Construction of a Recombinant Virus The p455 Promoter:

For a first animal experiment an Influenza hemagglutinin subtype H3 from a swine origin Influenza A virus (A/swine/Italy/7680/2001(H3N2), GenBank accession no.: ABS50302.2), SEQ ID NO:27 was used. Its coding sequence was synthesized and subcloned into transfer vector pU70-p455-71 K71 (FIG. 5) generating the transfer vector pU70-p455-H3-71 K71 , placing H3 under control of the new p455 promoter and the new 71 pA polyadenylation signal and framing the cassette with the recombination regions for insertion into orf70 (FIG. 6).

Figure 7:
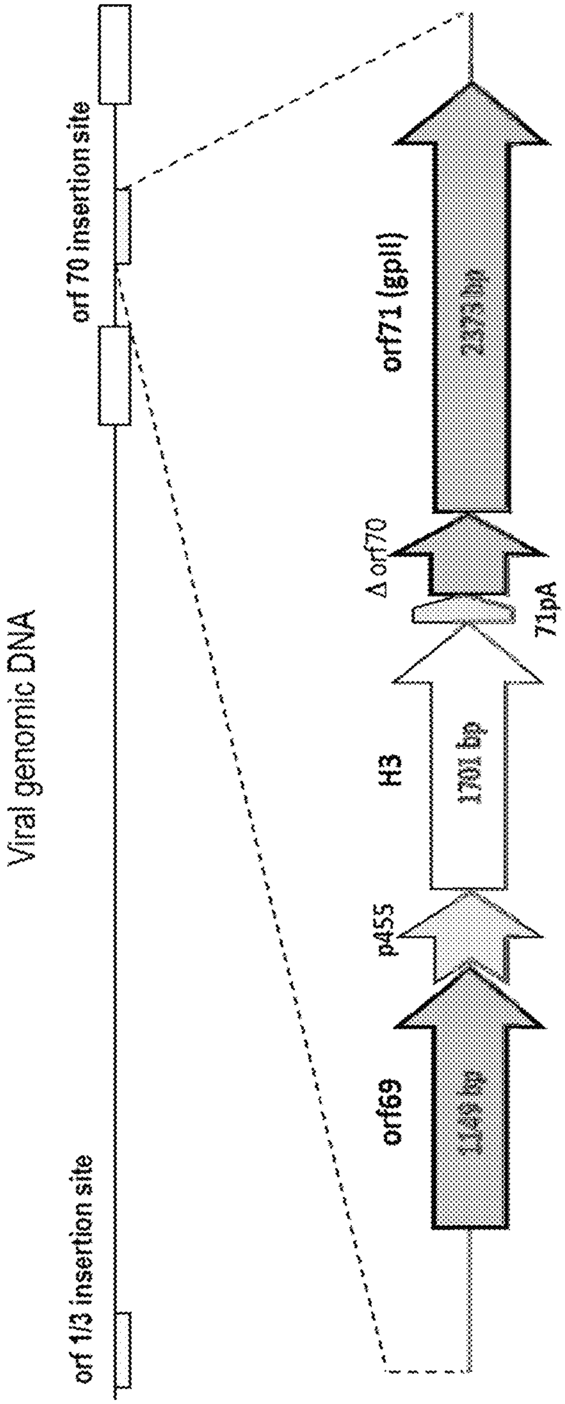
FIG. 7. Schematic illustration of the genome of rEHV-1 RacH-SE-70-p455-H3 with the orf70 insertion region enlarged. orf69: open reading frame number 69 upstream of the insertion site in orf70; p455: new promoter described herein, see e.g. example 1; H3: transgene Influenza Virus hemagglutinin; 71 pA: new polyadenylation sequence; Δorf70: remainder of orf70 containing the promoter for orf71 , which encodes the structural viral glycoprotein II (gpII).

By en passant mutagenesis using the RED recombination system (Tischer et al. 2006) the expression cassette p455-H3-71 was inserted in orf70 of pRacH-SE to generate pRacH-SE70-p455-H3 (FIG. 7).

Figure 8:
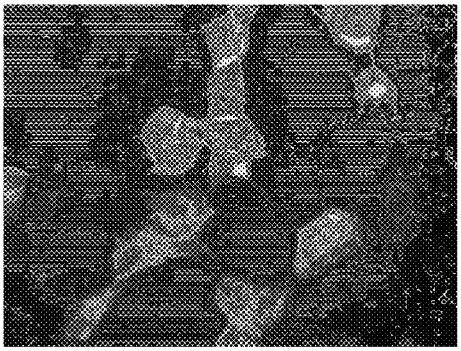
FIG. 8. Indirect immunofluorescence assay: Indirect immunofluorescence assay of VERO-cells infected with rEHV-1 RacH-SE-70-p455-H3 24 h p.i. cells were fixed with ethanol and air-dried. Using a commercial monoclonal antibody against H3 as primary antibody and a FITC-conjugated rabbit-anti mouse IgG as secondary antibody, H3 was shown in cells infected with the recombinant EHV-1 RacHSE-70-p455-H3 by fluorescence microscopy.

PK/WRL cells were transfected with pRacH-SE70-p455-H3, recombinant virus rEHV-1 RacH-SE70-p455-H3 was rescued and plaque-purified twice. Correct insertion of the expression cassette was verified by sequencing of a high-fidelity PCR product of the insertion region. Expression of the transgene in infected cells was analyzed by indirect immunofluorescence assay (IFA, FIG. 8).

Restoration of orf71 encoding EHV-1 gpII was confirmed by IFA (not shown) and Western blot (FIG. 9) using a monoclonal antibody Ai2G7 (owned by BI). Appearance of trimers of H3 on the plasma membrane of infected cells was assayed by a hemadsorption test using chicken erythrocytes (not shown). Peak titers determined as $TCID_{50}$/ml in PK/WRL cells were in the same range as titers of the parental virus rEHV-1 RacH-SE which indicates that transgene expression had no detrimental effect on viral replication (not shown). This was confirmed by passaging of rEHV-1 RacH-SE70-p455-H3 in PK/WRL cells up to passage 20 (P20) after rescue. At P5, P10, P15, and P20 the virus was characterized by titration, sequencing, and Western blot (FIG. 9), at P10 and P20 additionally by IFA, and HA expression and genetic stability of the HA encoding insert along with the promoter and polyA sequences were confirmed.

Figure 9:
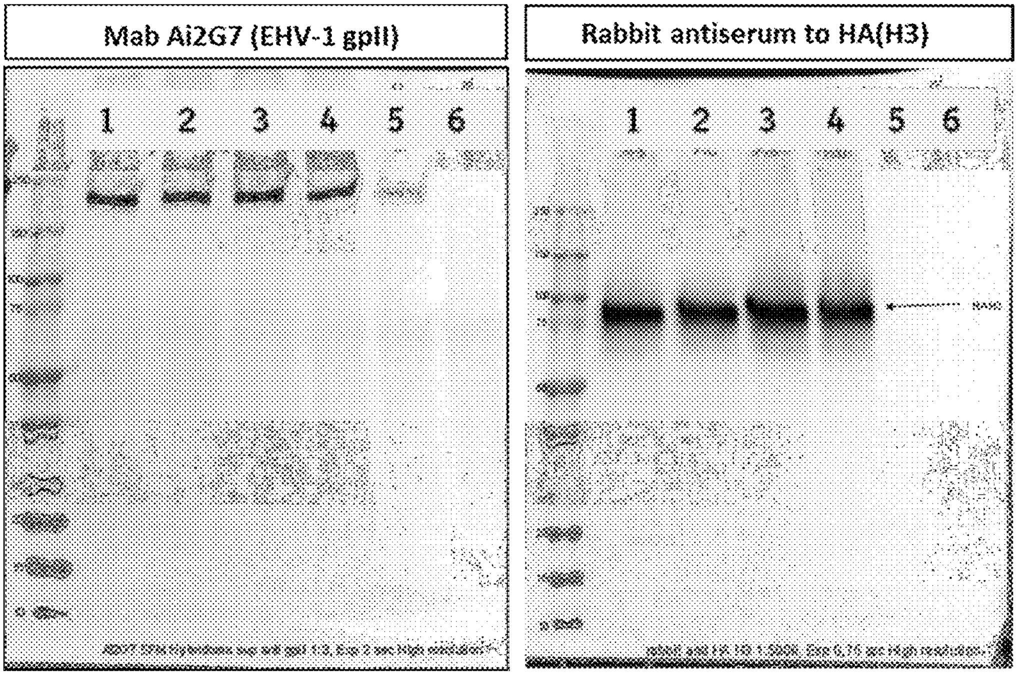
FIG. 9. Western blot: Western blot of cells infected with different passages of rEHV-1 RacH-SE-70-p455-H3 or a control rEHV-1 RacH-SE or mock-infected. The blot on the left was incubated with a monoclonal antibody Ai2G7 directed to gpII of EHV-1. The replica blot on the right was incubated with a commercial rabbit hyperimmune serum against Influenza A hemagglutinin H3 (PA5-34930). 1: rEHV-1 RacH-SE-70-p455-H3 P5 infected cells, 2: rEHV-1 RacH-SE-70-p455-H3 P10 infected cells, 3: rEHV-1 RacH-SE-70-p455-H3 P15 infected cells, 4: rEHV-1 RacH-SE-70-p455-H3 P20 infected cells, 5: rEHV-1 RacH-mC70 infected cells.

The two blots shown in FIG. 9 are replicas that were incubated with either the monoclonal antibody Ai2G7 (left) that specifically detects EHV-1 glycoprotein II (gpII) or with a commercial polyclonal antibody from rabbit (PA5-34930) raised against Influenza hemagglutinin subtype H3 (right). gpII was detected in all cell cultures infected with recombinant EHV-1 as expected. Full-length H3 was detected in all cells infected with the different passages of rEHV-1 RacH-SE-70-p455-H3 as expected. Specificity of the H3-antiserum was shown in the same Western blot, see lane gG430mC. Here only the gpII mab produced a reaction, as expected, while the anti-H3 antibody did not bind in the respective replica lane.

By double immunofluorescence assay (dIFA) of viral plaques in cells infected with P20 using a monoclonal anti-H3 antibody and a horse anti-EHV antiserum, it was confirmed that virtually all EHV-1 induced plaques also express H3 (not shown). All tests confirmed stability of the recombinant EHV-1 RacH-SE-70-p455-H3.

Example 4

Proof of Concept Animal Study (POC I) Using the p455 Promoter and Assessment of the Serological Response Test Animals: Inclusion Criteria and Experimental Design:

Five groups of ten piglets born from Influenza A-naive sows were included in the POC-I study as summarized in table 2.

TABLE 2

| Group | | No. of animals | Route | Dose |
|---|---|---|---|---|
| | Vaccine Treatment | | | |
| 1 | 1x NaCl;<br>1x EHV1 vector vaccine | 10 | i.m. | 2 ml NaCl;<br>2 ml EHV1, 1.00 × 107 TCID50 |
| 2 | 2x EHV1 vector vaccine | 10 | i.m. | 2× 2 ml EHV1, 1.00 × 107 TCID50 |
| 3 | 2x NaCl | 10 | i.m. | 2× 2 ml NaCl |
| 4 | 2x Inactivated vaccine | 10 | i.m. | 2× 2 ml Inact. |
| 5 | 2x NaCl | 10 | i.m. | 2× 2 ml NaCl |
| | Challenge Treatment | | | |
| 1 | H3N2 INFLUENZA A VIRUS FROM SWINE | 10 | Intratracheal | 8 ml; 1.00 × 107 TCID50/ml |
| 2 | H3N2 INFLUENZA A VIRUS FROM SWINE | 10 | Intratracheal | 8 ml; 1.00 × 107 TCID50/ml |
| 3 | H3N2 INFLUENZA A VIRUS FROM SWINE | 10 | Intratracheal | 8 ml; 1.00 × 107 TCID50/ml |
| 4 | H3N2 INFLUENZA A VIRUS FROM SWINE | 10 | Intratracheal | 8 ml; 1.00 × 107 TCID50/ml |
| 5 | cell culture medium (Negative Control) | 10 | Intratracheal | 8 ml |

An infectious dose of $1\times10^7$ $TCID_{50}$ of rEHV-1 RacH-70-p455-H3 (EHV-1) was applied either once at five weeks of age or twice at two and five weeks of age. For comparison commercially available inactivated vaccine (Inact) was applied twice at two and five weeks of age. All piglets were free of maternally derived antibodies in order not to abolish the effect of the inactivated vaccine (Inact). Two groups were not vaccinated but received injections with physiological sodium chloride solution (NaCl) to serve as challenge control or strict negative control, respectively. 21 days after the second vaccination all groups except the strict negative control group were challenged with $1\times10^7$ $TCID_{50}$ of a heterologous Influenza A (IAV) strain (H3N2 INFLUENZA A VIRUS FROM SWINE R452-14, challenge isolate owned by BI). While in the non-vaccinated challenge control group (Chall ctrl) all pigs had high influenza virus titers in their lungs at one and three days after challenge infection, all pigs in the strict negative control group (neg ctrl) and the group that had been vaccinated twice (EHV 2×) with rEHV-1 RacH-SE-70-p455-H3 were negative for IAV at both days. In the group vaccinated twice with the inactivated control vaccine (Inact 2×), one of five animals had a low IAV titer at day three after challenge. In the group vaccinated once (EHV 1×) 21 days prior to challenge with rEHV-1 RacH-SE-70-455-H3, two of five animals had low IAV titers in their lungs one day after challenge infection and one of five at three days after challenge. (FIG. 10).

Two vaccinations with $1\times10^7$ $TCID_{50}$ of rEHV-1 RacH-SE-70-p455-H3 completely protected pigs against challenge infection with a heterologous IAV, subtype H3N2. It was demonstrated that the EHV-1 vector RacH-SE is suitable for vaccination of pigs and that the new promoter 455 is functional in driving immunogenic expression of IAV hemagglutinin in vaccinated pigs.

Example 5

Use of the New p430 Promoter in Recombinant EHV-1 Vector Vaccines and Construction of a Recombinant Virus The p430 Promoter:

The newly identified p430 promoter was used to drive expression of another Influenza hemagglutinin from an H1N1 virus ((A/swine/Gent/132/2005(H1N1), GenBank accession no.: AFR76623.1), SEQ ID NO:28. Since the hemagglutinin gene in this virus isolate is from a Swine IAV of the "avian" type IAV it will be referred to as H1av. H1av was synthesized and subcloned in a transfer vector for the orf1/3 insertion region, pU1/3-p430-BGH_K_BGH (FIG. 11) to generate pU1/3-p430-H1av-BGH_K_GH. Expression of H1av was placed under control of the p430 promoter and the bovine growth hormone (BGH) polyA signal (FIG. 12).

Figure 13:
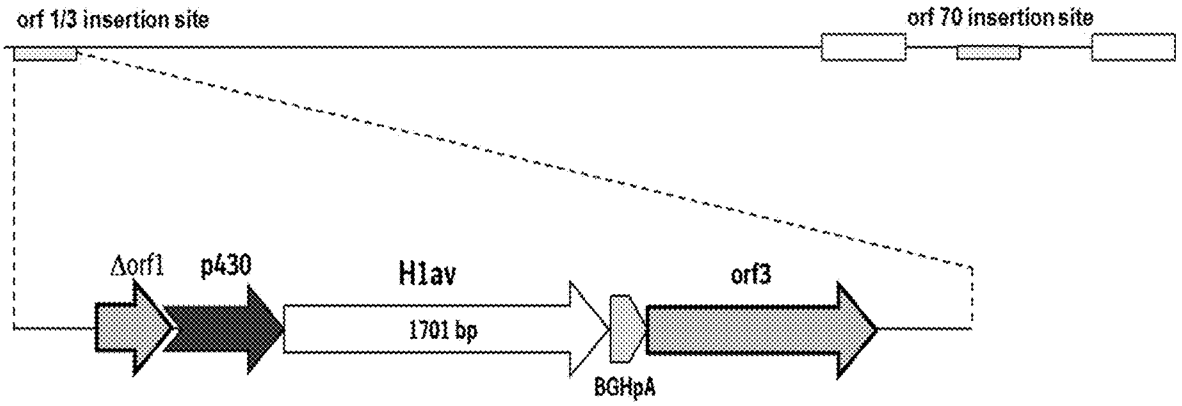
FIG. 13. Schematic illustration of the genome of rEHV-1 RacH-SE-1/3-p430-H1av with the orf1/3 insertion region enlarged. Δorf1: Remaining portion of open reading frame 1 upstream of the insertion site; p430: new promoter described herein, see e.g. example 1; H1av: transgene Influenza Virus hemagglutinin; BGHpA: bovine growth hormone polyadenylation sequence; orf3: open reading frame 3 downstream of insertion site.

By en passant mutagenesis using the RED recombination system (Tischer et al. 2006) the expression cassette p430-H1av-BGH was inserted in orf1/3 of pRacH-SE to generate pRacH-SE1/3-p430-H1av (FIG. 13).

Figure 14:
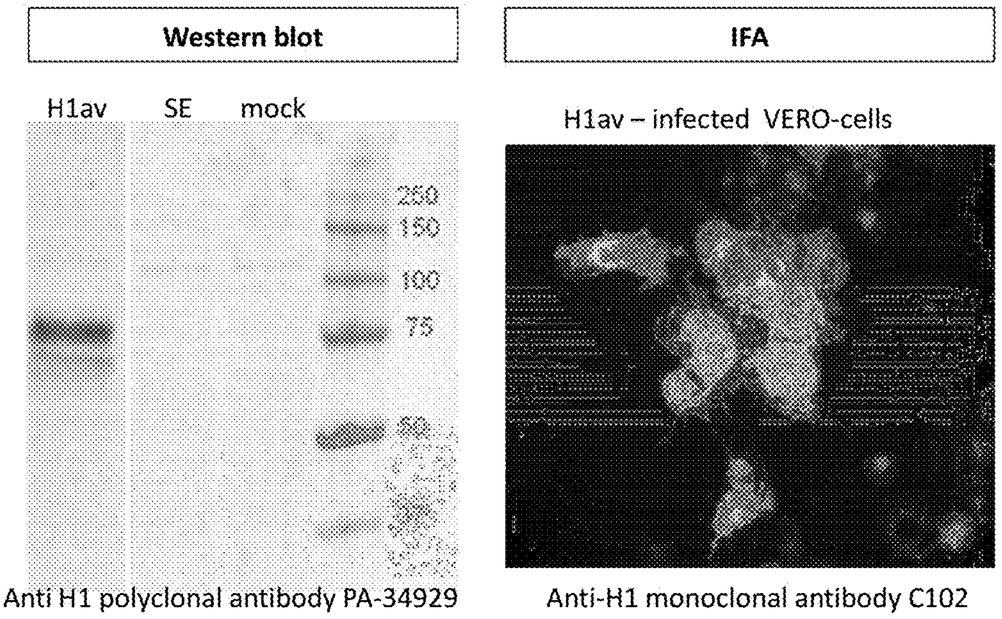
FIG. 14. Western blot and immunofluorescence of cells infected with rEHV-1 RacH-SE-1/3-p430-H1av showing expression of the transgene. H1av=rEHV-1 RacH-SE1/3-p430-H1av, SE=rEHV-RacH-SE (control), mock=uninfected cells (control).

PK/WRL cells were transfected with pRacH-SE1/3-p430-H1av, recombinant virus rEHV-1 RacH-SE1/3-p430-H1av was rescued and plaque-purified twice. Correct insertion of the expression cassette was verified by sequencing of a high-fidelity PCR product of the insertion region. Expression of the transgene in infected cells was analyzed by indirect immunofluorescence assay (IFA) and Western blot using commercially available monoclonal and polyclonal antibodies (FIG. 14). Restoration of orf71 encoding EHV-1 gpII was confirmed by IFA and Western blot using a monoclonal antibody Ai2G7 (owned by BI), (not shown). Correct processing and transport of H1av and localization in the plasma membrane of infected cells was assayed by a hemadsorption test using chicken erythrocytes (not shown). Peak titers determined as TCID50/ml in PK/WRL cells were in the same range as titers of the parental virus RacH-SE which indicates that transgene expression had no detrimental effect on viral replication (not shown).

Specific detection of a broad band migrating at 75 kDa by antibody PA-34929 is in concordance with the expected appearance of the recombinant HA glycoprotein as predicted from its sequence. Apparent staining of cellular membranes with the monoclonal antibody C102 is in line with the subcellular localization as expected (FIG. 14).

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst33342 and appear as tiny blue specks by fluorescence microscopy, Compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus infection.

The clear phenotype of hemadsorption of infected cells supports the findings of the Western blots and immunofluorescence assays showing efficient expression of the transgenic proteins and suggesting formation of functional HA trimers on the cell surface of EHV-1 vector infected cells.

Example 6

Use of the Two New Promoters p455 and p430 in Recombinant EHV-1 Vector Vaccines in Two Insertion Sites in Parallel To show that the two new promoters can be used in parallel a recombinant EHV-1 RacH was generated expressing two different hemagglutinins of two different Influenza A virus subtypes.

Specificity and lack of cross-reactivity of the polyclonal commercial antibodies to H3 (PA5-34930) and H1 (PA5-34929) was verified by Western blots of infected cells infected with single-insert viruses rEHV-1 RacH-SE-70-p455-H3 and rEHV-1 RacH-SE-1/3-p430-H1av (not shown).

Figure 15:
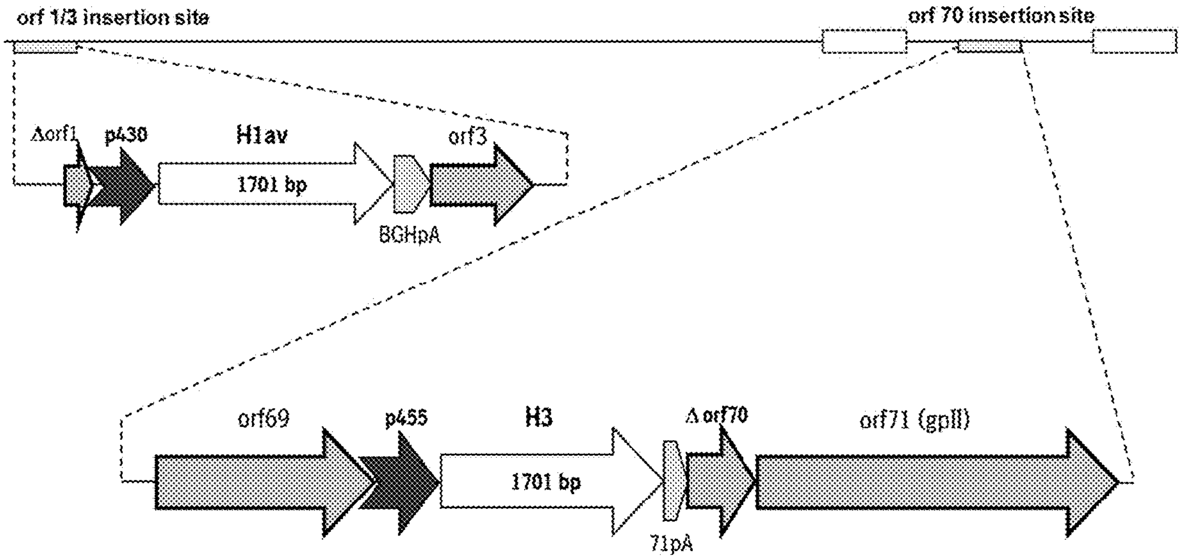
FIG. 15. Schematic illustration of the genome of rEHV-1 RacH-SE-1/3-p430-H1av-70-p455-H3 (rEHV-1-RacH-SE B) with the two insertion regions enlarged. Δorf1: Remaining portion of open reading frame 1 upstream of the insertion site; p430: new promoter; H1av: transgene Influenza Virus hemagglutinin; BGHpA: bovine growth hormone polyadenylation sequence; orf3: open reading frame 3 downstream of insertion site., orf69: open reading frame 69 upstream of the insertion site in orf70; p455: new promoter; H3: transgene Influenza Virus hemagglutinin; 71 pA: new polyadenylation sequence; Δorf70: remainder of orf70 containing the promoter for orf71 , which encodes the structural viral glycoprotein II (gpII).

Starting with the recombinant BAC pRacH-SE-70-p455-H3, the expression cassette p430-H1av-BGH as assembled in the transfer vector pU1/3-p430-H1av-BGHKBGH (FIG. 12) was inserted into the orf1/3 insertion site by two-step RED recombination to generate pRacH-SE-1/3-p430-H1av-70-p455-H3. PK/WRL cells were transfected with pRacH-SE1/3-p430-H1av-70-p455-H3, and recombinant virus rEHV-1 RacH-SE1/3-p430-H1av-70-p455-H3 was rescued and plaque-purified twice (FIG. 15).

Figure 16:
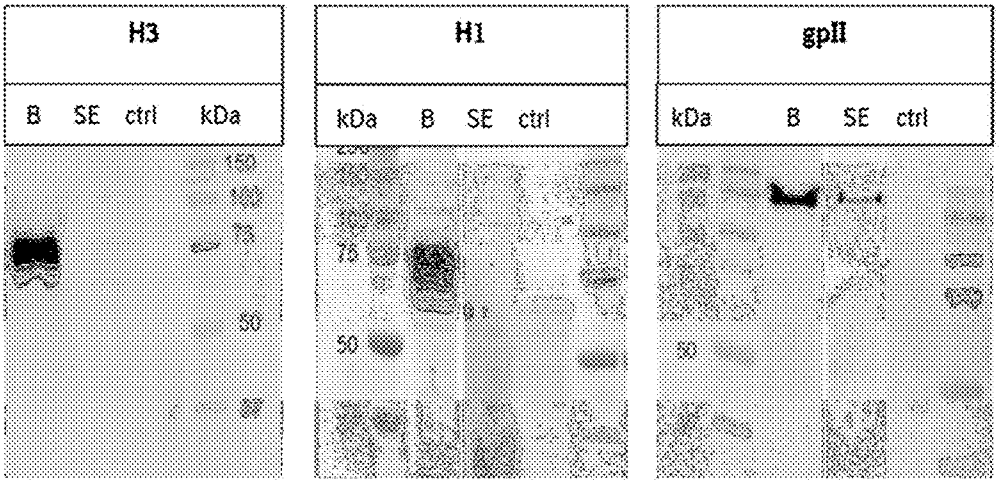
FIG. 16. Western blot: Western blot of cells infected with rEHV-1 RacH-SE-1/3-p430-H1av-70-p455-H3 (B), empty vector rEHV-1 RacH-SE (SE), or mock-infected (ctrl). Replica blots were incubated with either a commercial rabbit hyperimmune serum to H3 (H3), a commercial rabbit hyperimmune serum (PA 34929) to H1 (H1), or a monoclonal antibody Ai2G7 to EHV-1 gpII (gpII).

The short designation for this recombinant virus is rEHV-1 RacH-SE_B. Correct insertion of the expression cassette was verified by sequencing of high-fidelity PCR products of the insertion regions together with flanking sequences. Expression of the transgenes in infected cells was analyzed by indirect immunofluorescence assay (IFA, not shown) and Western blot using commercially available monoclonal and polyclonal antibodies (FIG. 16). Restoration of orf71 encoding EHV-1 gpII was confirmed by IFA (not shown) and Western blot using a monoclonal antibody Ai2G7 (owned by BI), (FIG. 16).

As shown in FIG. 16 both transgenes H3 and H1av were expressed in parallel in cell cultures infected with the dual insert recombinant rEHV-1 RacH-SE-1/3-p430-H1av-70-p455-H3. Transgene expression was stable and did not impair viral titers tested until passage 11 in PK/WRL cells (not shown).

The two new promoters p430 and p455 were shown to be functional in the context of rEHV1-RacH replication in cell cultures. Activity levels during the viral replication cycle appear to be very similar as deduced from in vitro promoter kinetic experiments. These properties allow creation of recombinant vector vaccines based on EHV-1 RacH or other vector platforms expressing two different antigens in parallel with similar efficiency. If a vaccine target consists of two different pathogens application of the two new promoters in two insertion sites combined with two polyadenylation sequences can reduce cost of goods significantly and represents a clear advantage over a vector expressing only one antigenic component.

Example 7

Generation, In Vitro Characterization and In Vivo Testing of a Monovalent Ehv-1 Vectored Influenza a Virus Vaccine (H3 Vaccine) for Swine Swine IAV Influenza virus hemagglutinin of serotype H3 (SEQ ID NO 27) (A/swine/Italy/7680/2001(H3N2), GenBank accession no.: ABS50302.2) was chosen as antigen to be tested for vaccination study in pigs. This new vaccine against swine IAV provides a DIVA feature, e.g. by detection of antibodies against Swine IAV proteins NP or NA in animals that were infected by Swine IAV field strains but not in animals only vaccinated with the vaccine described here since it only expresses one Swine IAV HA protein. Its coding sequence was synthesized and subcloned generating the transfer vector pU70-p455-H3-71 K71 , placing H3 under control of the new p455 promoter and the new 71 pA polyadenylation signal and framing the cassette with the recombination regions for insertion into orf70 (FIG. 1B).

By en-passant mutagenesis using the RED recombination system the expression cassette p455-H3-71 was inserted in orf70 of pRacH-SE to generate pRacH-SE70-p455-H3.

PK/WRL cells were transfected with pRacH-SE70-p455-H3, recombinant virus rEHV-1 RacH-SE70-p455-H3 was rescued and plaque-purified twice (FIG. 7).

Correct insertion of the expression cassette was verified by sequencing of a high-fidelity PCR product of the insertion region. Expression of the transgene in infected cells was analyzed by indirect immunofluorescence assay (IFA, FIG. 8) and Western blot (FIG. 9) using commercially available monoclonal and polyclonal antibodies.

Restoration of orf71 encoding EHV-1 gpII was confirmed by IFA (not shown) and Western blot (FIG. 9) using a monoclonal antibody Ai2G7 (owned by BI). Appearance of trimers of H3 on the plasma membrane of infected cells was assayed by a hemadsorption test using chicken erythrocytes (not shown). Peak titers determined as $TCID_{50}$/ml in PK/WRL cells were in the same range as titers of the parental virus RacH-SE which indicates that transgene expression had no detrimental effect on viral replication (not shown). This was confirmed by passaging of rEHV-1 RacH-SE70-p455-H3 in PK/WRL cells up to passage 20 (P20) after rescue. At P5, P10, P15, and P20 the virus was characterized by titration, sequencing, and Western blot (FIG. 9), at P10 and P20 additionally by IFA, and HA expression and genetic stability of the HA encoding insert along with the promoter and polyA sequences were confirmed.

The two blots shown in FIG. 9 are replicas that were incubated with either the monoclonal antibody Ai2G7 (left) that specifically detects EHV-1 glycoprotein II (gpII) or with a commercial polyclonal antibody from rabbit (PA5-34930) raised against Influenza hemagglutinin subtype H3 (right). gpII was detected in all cell cultures infected with recombinant EHV-1 as expected. Full-length H3 was detected in all cells infected with the different passages of rEHV-1 RacH-SE-70-p455-H3 as expected. Specificity of the H3-antiserum was also shown by Western blots of cells infected with other recombinant EHV-1 RacH-SE expressing Influenza hemagglutinins from H1 subtype viruses, see, FIG. 16.

By double immunofluorescence assay (dIFA) of viral plaques in cells infected with P20 using a monoclonal anti-H3 antibody and a horse anti-EHV antiserum, it was confirmed that virtually all EHV-1 induced plaques also express H3 (not shown). All tests confirmed stability of the recombinant EHV-1 RacH-SE-70-p455-H3.

To investigate its properties as a vectored vaccine in young piglets, rEHV-1 RacH-SE-70-p455-H3 was tested in a vaccination-challenge study. In detail, piglets without maternally derived immunity against Swine IAV (no maternal antibodies) were vaccinated twice with cell culture supernatant containing RacH-SE-70-p455-H3 at a dose of 1×10^7 TCID50 intramuscularly at an age of two and five weeks (two-shot vaccination, 2×EHV-1), or at an age of five weeks only (one-shot vaccination, 1×EHV-1). A non-vaccinated group served as negative control and a group of animals that were vaccinated at two and five weeks of age with a commercially available inactivated Swine IAV vaccine according to the manufacturer's instructions (but for the time points of vaccination) served as positive control (killed). At an age of 8 weeks, all animals but the negative control were challenged by an intratracheally applied dosage of 1×10^7 TCID50 of an H3N2 Swine IAV challenge strain (European field virus isolate R452-14 whose H3 is being heterologous to the H3 vaccine antigen used in RacH-SE-70-p455-H3). Non-vaccinated and unchallenged animals served as negative control, while non-vaccinated but challenged animals served as challenge control. At and after vaccinations and before and after challenge, body temperatures were measured and blood samples were taken at different time points. One day after challenge, half of the animals per group were killed and the lungs were scored for lesions typical for Swine IAV infection, three lung samples per left and right lung were taken per animal, respectively, to determine infectious Swine IAV titers in lung homogenates, and bronchi alveolar lavage fluid (BALF) was sampled. The same procedure was performed with the remaining half on animals per group three days after challenge.

Figure 17:
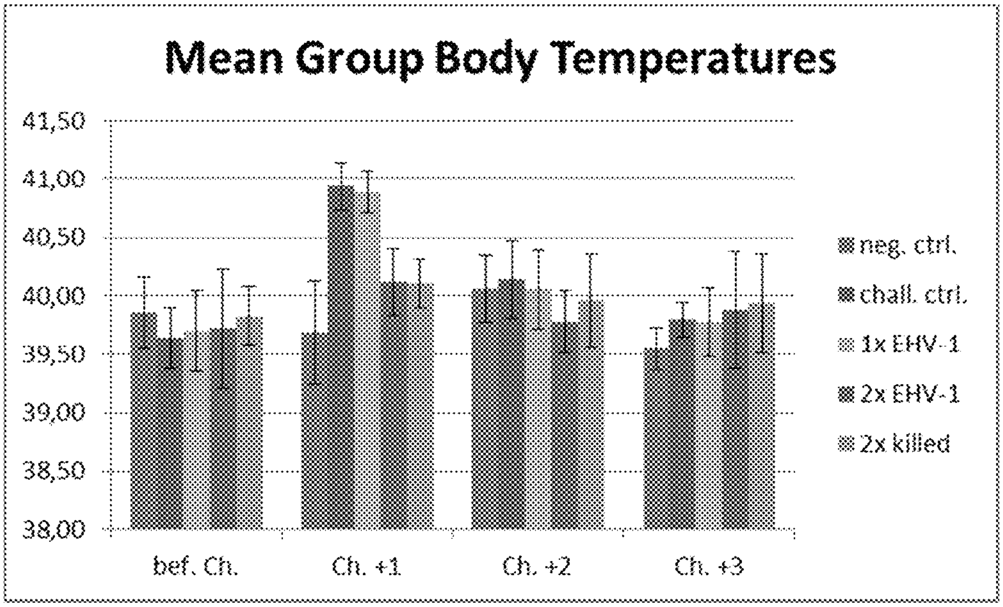
FIG. 17. Mean body temperatures of groups before and at 1, 2, and 3 days after challenge. Error bars, standard deviations. From left to right per study day: negative control group (neg. ctrl.), challenge control group (chall. ctrl.), animals vaccinated once with RacH-SE-70-p455-H3 (1×EHV-1), vaccinated twice with RacH-SE-70-p455-H3 (2×EHV-1), or twice with inactivated Swine IAV vaccine (2× killed).

When investigating the body temperature rise after Swine IAV challenge virus application, non-vaccinated animals showed a body temperature increase of about 1° C. 1 day after challenge. This body temperature increase 1 day after challenge was prevented for the group vaccinated twice with the RacH-SE-70-p455-H3 vaccine (FIG. 17).

Figure 18:
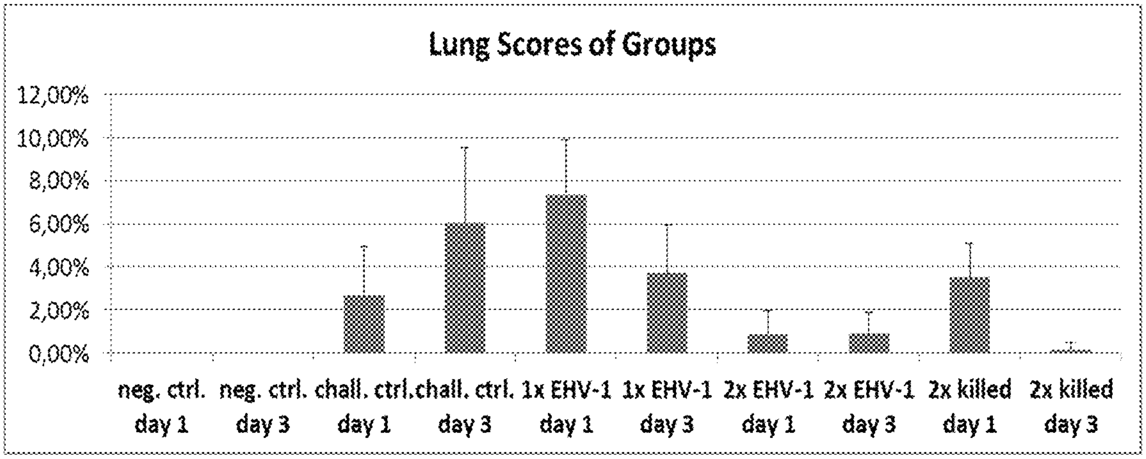
FIG. 18. Mean lung scores of groups one and three days after challenge. Error bars, standard deviations. Negative control group (neg. ctrl.), challenge control group (chall. ctrl.), animals vaccinated once with RacH-SE-70-p455-H3 (1×EHV-1), vaccinated twice with RacH-SE-70-p455-H3 (2×EHV-1), or twice with inactivated Swine IAV vaccine (2× killed).

Assessment of the lung scores from animals killed at 1 or 3 days after Swine IAV challenge virus application revealed that the negative control showed no lung lesions typical for Swine IAV infection, the challenge control showed lung lesions in the mean range of 6-7%, and that regarding the group mean values lung lesion scores were strongly reduced to one to less than 4% for the group vaccinated twice with the RacH-SE-70-p455-H3 vaccine (FIG. 18).

The mean Swine IAV lung titers from animals killed at 1 or 3 days after Swine IAV challenge virus application showed that the negative control showed no Swine IAV in lung samples, whereas the challenge control showed virus titers per g lung tissue in the range of more than 5 (day 3) to more than 7 logs (day 1). In stark contrast, the group mean values were strongly reduced to about two logs or less for the group vaccinated once with the RacH-SE-70-p455-H3 vaccine and reduced to undetectable levels for the group vaccinated twice with the RacH-SE-70-p455-H3 vaccine (FIG. 10).

Figure 19:
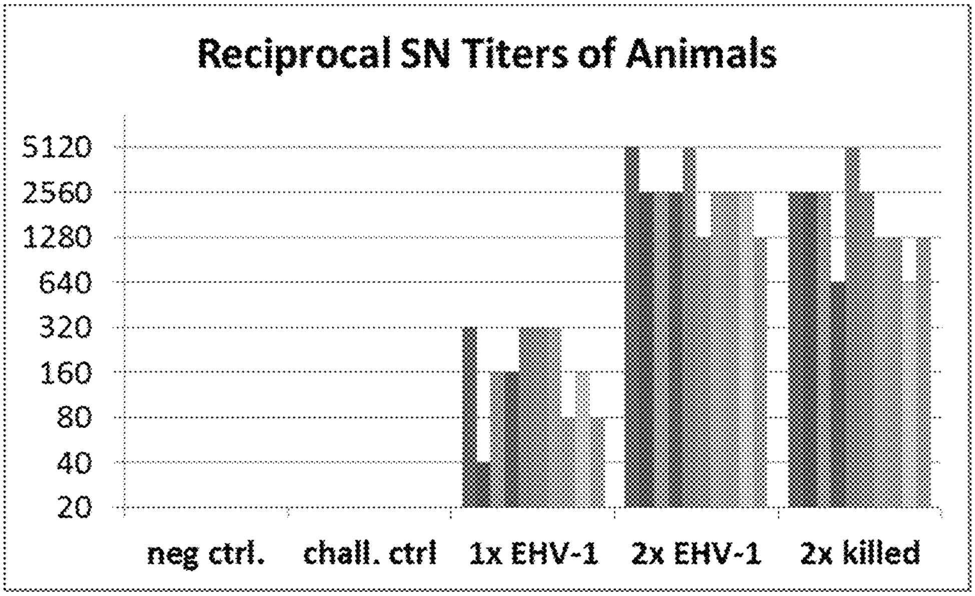
FIG. 19. Reciprocal serum neutralization (SN) titers of animal sera against Swine IAV H3 challenge strain R452-14 collected at day of challenge. 20, detection limit. Negative control group (neg. ctrl.), challenge control group (chall. ctrl.), animals vaccinated once with RacH-SE-70-p455-H3 (1×EHV-1), vaccinated twice with RacH-SE-70-p455-H3 (2×EHV-1), or twice with inactivated Swine IAV vaccine (2× killed).

When testing the induction of Swine IAV neutralizing antibodies after vaccination, sera from animals vaccinated once with the RacH-SE-70-p455-H3 vaccine showed reciprocal neutralization titers in the range of about 160 three weeks after first vaccination and sera from animals vaccinated twice with the RacH-SE-70-p455-H3 vaccine showed neutralizing titers of about 2560 three weeks after $2^{nd}$ vaccination, while sera from the non-vaccinated groups had no detectable Swine IAV neutralizing antibody levels (FIG. 19).

Figure 20:
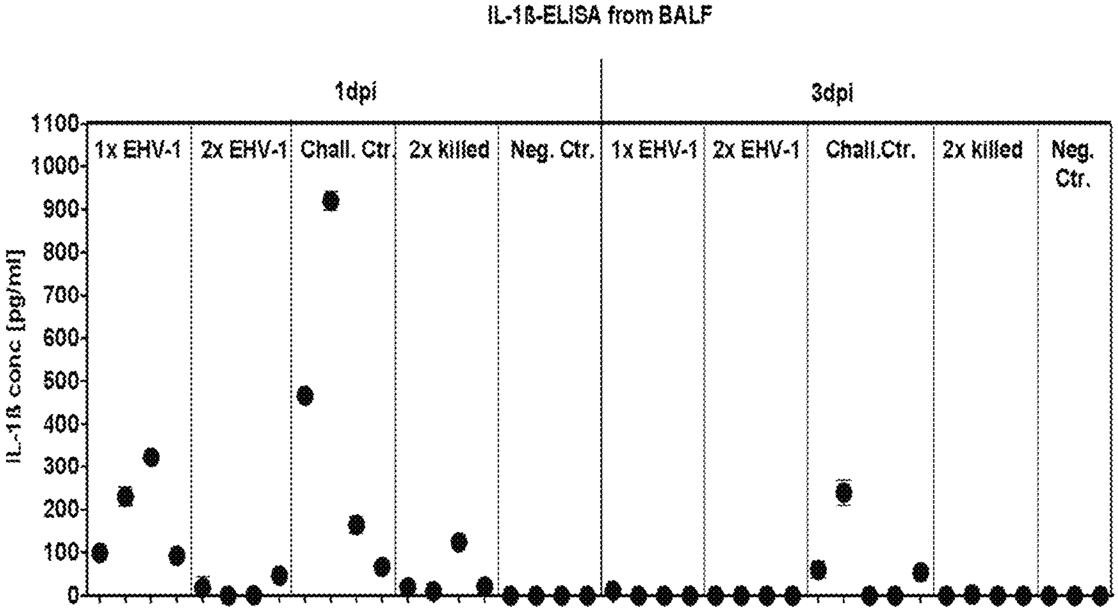
FIG. 20. Results from IL-1β from BALF taken one or two days after Swine IAV challenge application. Each dot represents the value determined per one animal. Negative control group (Neg. Ctr.), challenge control group (Chall. Ctr.), animals vaccinated once with RacH-SE-70-p455-H3 (1×EHV-1), vaccinated twice with RacH-SE-70-p455-H3 (2×EHV-1), or twice with inactivated Swine IAV vaccine (2× killed).

When determining the amounts of pro-inflammatory cytokine IL-1β in BALF from animals 1 or 3 days after Swine IAV challenge, IL-1β levels of more than 100 pg/ml up to 900 pg/ml were detectable in three of four animals tested at day 1, whereas these levels were reduced to 100-300 pg/ml IL-1β for BALFs from animals vaccinated once with the RacH-SE-70-p455-H3 vaccine and even further reduced to levels of 0 to less than 100 pg/ml IL-1β for all animals vaccinated twice with the RacH-SE-70-p455-H3 vaccine (FIG. 20). This shows that vaccination with the RacH-SE-70-p455-H3 vaccine had effectively prevented induction of the pro-inflammatory cytokine IL-1β after Swine IAV infection.

Figure 21:
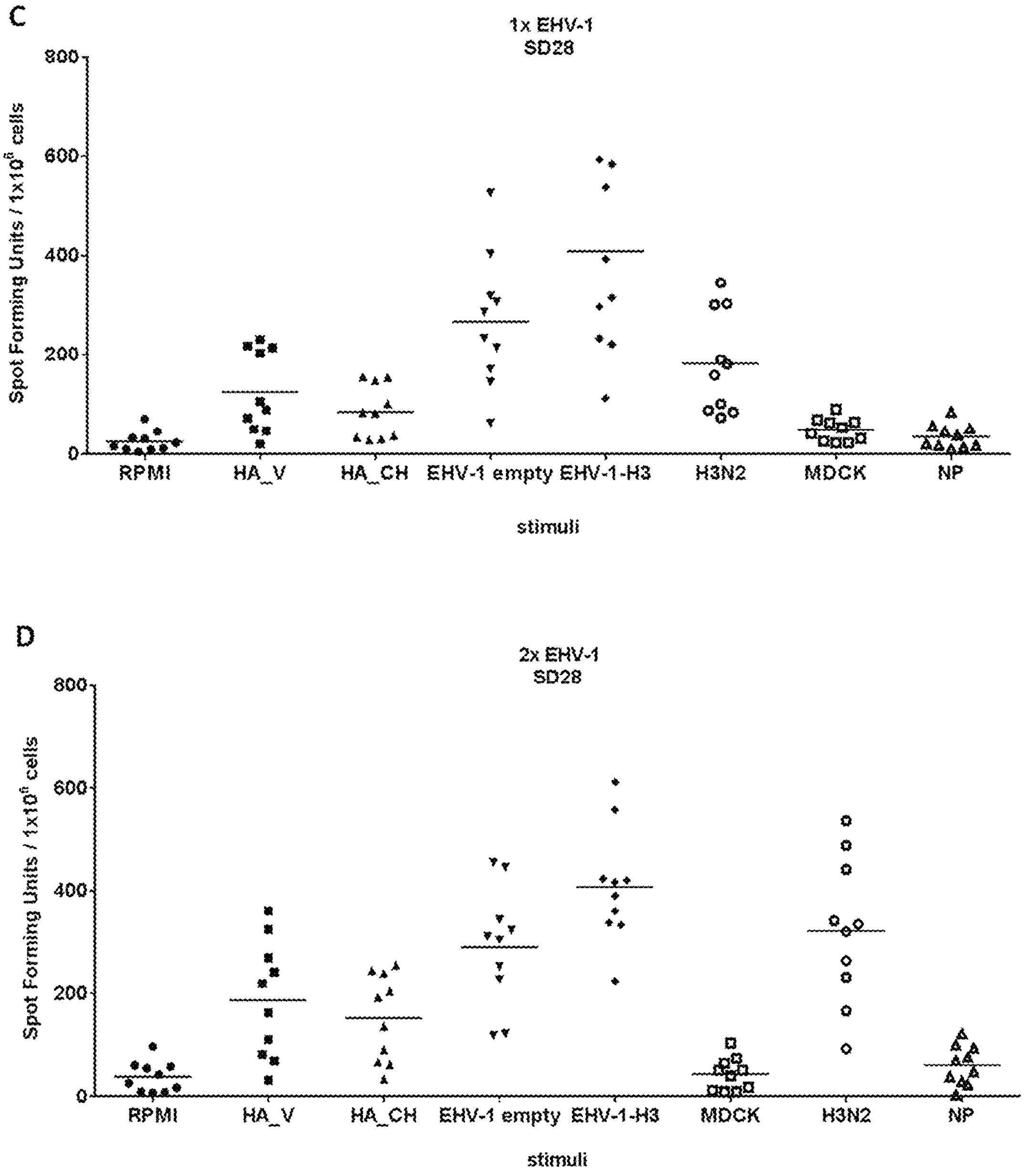
FIG. 21. Results from IFNγ-ELISpots of PBMCs restimulated 7 days after 2nd vaccination. (A), unvaccinated control group; (B), vaccinated twice with inactivated Swine IAV vaccine; (C), vaccinated once with rEHV-1 RacH-SE-70-p455-H3; (D), vaccinated twice with rEHV-1 RacH-SE-70-p455-H3. For animals vaccinated only once with rEHV-1 RacH-SE-70-p455-H3 restimulation corresponds to 7 days after 1st vaccination. Each dot represents the value determined per one animal for the given time point and after restimulation with the specific stimulus. For restimulation, recombinantly expressed Swine IAV HA corresponding to the H3 vaccine antigen in rEHV-1 RacH-SE-70-p455-H3 (HA_V), recombinantly expressed Swine IAV HA corresponding to the H3 of challenge strain R452-14 (HA_CH), the media to dilute HA_V and HA_CH (RPMI), empty EHV-1 vector RacH-SE (EHV-1 empty), vaccine RacH-SE-70-p455-H3 (EHV-1-H3), Swine IAV H3N2 challenge strain R452-14 (H3N2), cell supernatant from non-infected cells used to grow R452-14 (MDCK), or recombinantly expressed Swine IAV nucleoprotein (NP) were used.

When testing restimulation of peripheral blood mononuclear cells (PBMCs) sampled at study day 28 and using different stimuli, stimulation of PBMCs from non-vaccinated animals showed less than 75/1×10^6 counts in IFNγ-ELISpot irrespective of the stimuli used (FIG. 21, A). PBMCs of animals that had received the inactivated vaccine twice (killed) showed about 150/1×10^6 counts when they were restimulated with recombinant Swine IAV nucleoprotein NP and about 3000/1×10^6 counts in IFNγ-ELISpot when they were restimulated with Swine IAV H3N2 challenge strain R452-14, but showed no restimulation of PBMCs (levels of 75/1×10^6 counts or lower) when recombinant Swine IAV HAs or EHV-1 viruses were used (FIG. 21, B). In contrast, animals vaccinated once or twice with RacH-SE-70-p455-H3 vaccine also showed about 200 (1×EHV-1) to 300 (2×EHV-1)/1×10^6 counts in IFNγ-ELISpot when they were restimulated with Swine IAV H3N2 challenge strain R452-14, but no restimulation of PBMCs (levels of 75/1×10^6 counts or lower) when recombinant Swine IAV NP was used (FIGS. 21 C and D). When EHV-1 viruses were used for restimulation, animals vaccinated once or twice with RacH-SE-70-p455-H3 vaccine showed about 300/1×10^6 counts in IFNγ-ELISpot when they were restimulated with empty EHV-1 vaccine RacH-SE, and this value was further increased to more than 400/1×10^6 counts when RacH-SE-70-p455-H3 vaccine expressing a Swine IAV H3 was used, respectively (FIGS. 21 C and D). Accordingly, when recombinant Swine IAV HAs were used for restimulation, only animals vaccinated once or twice with RacH-SE-70-p455-H3 vaccine showed about 100-150 (1×EHV-1) to 150-200 (2×EHV-1)/1×10^6 counts in IFNγ-ELISpot (FIGS. 21 C and D).

Example 8

Generation, In Vitro Characterization and In Vivo Testing of a Tetravalent Ehv-1 Vectored Influenza A Virus Vaccine for Swine As described below, in the described invention the four above-described Swine IAV hemagglutinin (HA) antigens derived from H1N2, H3N2, H1N1 avian, and H1N1 pandemic Swine IAV sub-/serotypes are expressed by two recombinant EHV-1 vector viruses. This new tetravalent vaccine against swine IAV provides a DIVA feature, e.g. by detection of antibodies against Swine IAV proteins NP or NA in animals that were infected by Swine IAV field strains but not in animals only vaccinated with the vaccine described here since it only expresses the Swine IAV HA proteins.

The new tetravalent Swine IAV vaccine was characterized in vitro and is tested in vivo for its efficacy against Swine IAV.

The newly identified p430 promoter was used to drive expression of Swine IAV H1N1 ((A/swine/Gent/132/2005 (H1N1), GenBank accession no.: AFR76623.1). Since the hemagglutinin gene in this virus isolate originated from an avian IAV it will be referred to as H1av. H1av was synthesized and subcloned in a transfer vector for the orf1/3 insertion region to generate pU1/3-p430-H1av-BGH K_BGH. Expression of H1av was placed under control of the p430 promoter and the bovine growth hormone (BGH) polyA signal and framed with the recombination regions for insertion into orf1/3 (FIG. 12).

By en-passant mutagenesis using the RED recombination system the expression cassette p430-H1av-BGH was inserted in orf1/3 of pRacH-SE to generate pRacH-SE1/3-p430-H1av. PK/WRL cells were transfected with pRacH-SE1/3-p430-H1av, recombinant virus rEHV-1 RacH-SE1/3-p430-H1av (FIG. 13) was rescued and plaque-purified twice. Correct insertion of the expression cassette was verified by sequencing of a high-fidelity PCR product of the insertion region. Expression of the transgene in infected cells was analyzed by indirect immunofluorescence assay (IFA) and Western blot using commercially available monoclonal and polyclonal antibodies (FIG. 14). Restoration of orf71 encoding EHV-1 gpII was confirmed by IFA and Western blot using a monoclonal antibody Ai2G7 (owned by BI), (not shown). Correct processing and transport of H1av and localization in the plasma membrane of infected cells was assayed by a hemadsorption test using chicken erythrocytes (not shown). Peak titers determined as TCID50/ml in PK/WRL cells were in the same range as titers of the parental virus RacH-SE which indicates that transgene expression had no detrimental effect on viral replication (not shown).

Specific detection of a broad band migrating at 75 kDa by antibody PA-34929 is in concordance with the expected appearance of the recombinant HA glycoprotein as predicted from its sequence. Apparent staining of cellular membranes with the monoclonal antibody C102 is in line with the subcellular localization as expected.

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst 33342 and appear as tiny blue specks by fluorescence microscopy, compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus replication. The phenotype of hemadsorption of infected cells supports the findings of the Western blots and immunofluorescence assays (for H1av, FIG. 14) showing efficient expression of the transgenic proteins and suggesting formation of functional HA trimers on the cell surface of EHV-1 vector infected cells.

Specificity and lack of cross-reactivity of the polyclonal commercial antibodies to H3 (PA5-34930) and H1 (PA5-34929) was verified by Western blots of infected cells infected with single-insert viruses rEHV-1 RacH-SE-70-p455-H3 and rEHV-1 RacH-SE-1/3-p430-H1av (not shown).

Next, a recombinant EHV-1 RacH-SE was generated expressing two different hemagglutinins of two different Influenza A virus sub-/serotypes.

Starting with the recombinant BAC pRacH-SE-70-p455-H3, the expression cassette p430-H1av-BGH as assembled in the transfer vector pU1/3-p430-H1av-BGH_K_BGH (FIG. 12) was inserted into the orf1/3 insertion site by two-step RED recombination to generate pRacH-SE-1/3-p430-H1av-70-p455-H3. PK/WRL cells were transfected with pRacH-SE1/3-p430-H1av-70-p455-H3, and recombinant virus rEHV-1 RacH-SE1/3-p430-H1av-70-p455-H3 was rescued and plaque-purified twice. The short designation for this recombinant virus is rEHV-1 RacH-SE B (FIG. 15). Correct insertion of the expression cassette was verified by sequencing of high-fidelity PCR products of the insertion regions together with flanking sequences.

Expression of the transgenes in infected cells was analyzed by indirect immunofluorescence assay (IFA, not shown) and Western blot using commercially available monoclonal and polyclonal antibodies (FIG. 16). Restoration of orf71 encoding EHV-1 gpII was confirmed by IFA (not shown) and Western blot using a monoclonal antibody Ai2G7 (owned by BI), (FIG. 16).

Both transgenes H3 and H1av were expressed in parallel in cell cultures infected with the dual insert recombinant rEHV-1 RacH-SE_B. Transgene expression was stable and did not impair viral titers tested until passage 11 in PK/WRL cells.

The enhanced EHV-1 vector with two insertion sites and two new promoters was shown to express two Influenza virus hemagglutinins in parallel. Subcellular localization as determined by IFA and mobility in SDS-PAGE as determined by Western blot corresponded to authentic hemagglutinins expressed in Influenza A virus infected cells known from the literature.

Next, a second double-insert rEHV-1 RacH expressing hemagglutinins H1hu, SEQ ID NO:29, (A/swine/Italy/4675/2003(H1N2); GenBank accession no. ADK98476.1) and H1pdm, SEQ ID NO:26, (A/swine/Italy/116114/2010 (H1N2); GenBank accession no. ADR01746.1) was generated.

The coding sequence of H1hu was synthesized and subcloned in a transfer vector for the orf1/3 insertion region to generate pU1/3-p430-H1hu-BGHKBGH. Expression of H1hu was placed under control of the p430 promoter and the bovine growth hormone (BGH) polyA signal and framed with the recombination regions for insertion into orf1/3 (FIG. 22).

The coding sequence of H1pdm was synthesized and subcloned generating the transfer vector pU70-p455-H1pdm-71 K71 , placing H1pdm under control of the new p455 promoter and the new 71 pA polyadenylation signal and framing the cassette with the recombination regions for insertion into orf70 (FIG. 23).

Figure 24:
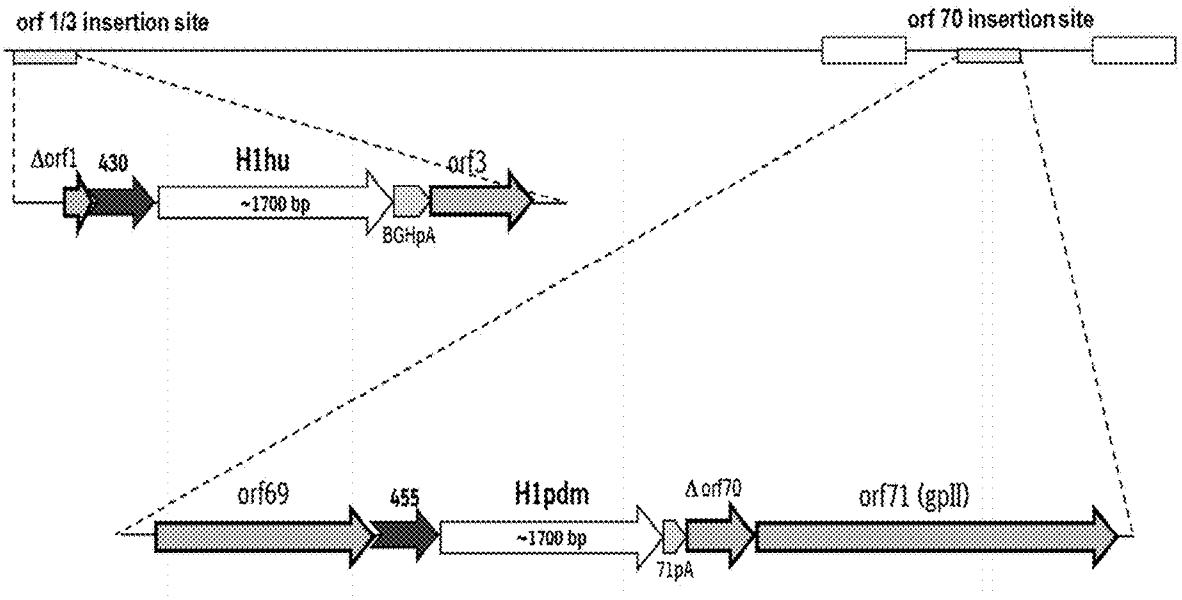
FIG. 24: The linear double-stranded DNA genome of rEHV-1 RacH-SE-1/3-p430-H1hu-70-p455-H1pdm (rEHV-1 RacH-SE_D) with the orf1/3 and orf70 insertion regions enlarged.

Subsequently, the expression cassettes p430-H1av-BGH and p455-H1pdm-71 were inserted into pRacH-SE by en-passant mutagenesis using the RED recombination system, generating pRacH-SE-1/3-p430-H1hu first. Using this modified BAC as the target, p455-H1pdm-71 was inserted by en passant mutagenesis using the RED recombination system, generating pRacH-SE-1/3-p430-H1hu-70-p455-H1pdm. pRacH-SE-1/3-p430-H1hu-70-p455-H1pdm was transfected in PK/WRL cells and rEHV-1 RacH-SE-1/3-p430-H1hu-70-p455-H1pdm was rescued and plaque purified three times. The short designation of the new recombinant vector virus is rEHV-1 RacH-SE_D (FIG. 24).

Figure 25:
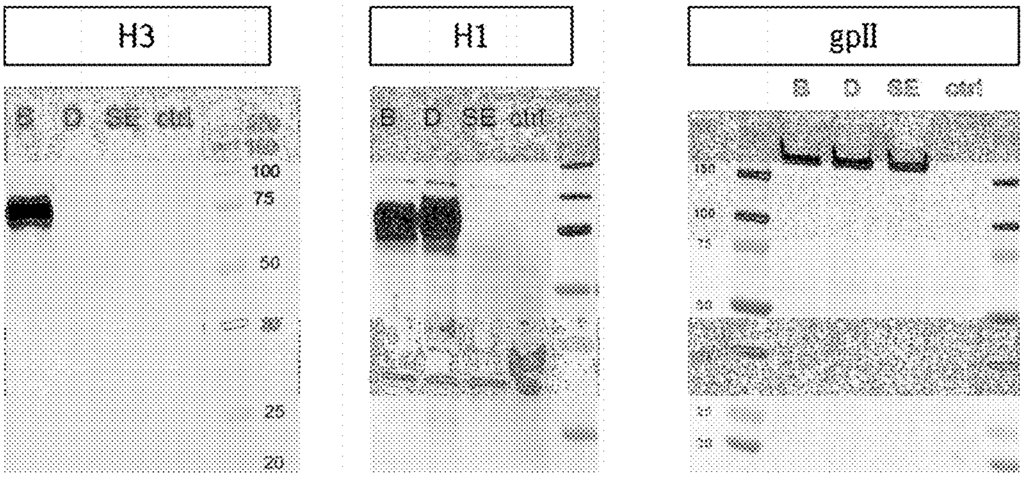
FIG. 25: Western blots of cells infected with rEHV-1 RacH-SE_B, RacH-SE_D, RacH-SE, or uninfected (ctrl). Replica blots were incubated either with a polyclonal rabbit hyperimmune serum directed against H3 (PA5-34930), a polyclonal rabbit hyperimmune serum directed against H1 (PA5-34929), or a monoclonal antibody (Ai2G7) against EHV-1 glycoprotein II (gpII). All antibodies produced the expected patterns confirming expression of the desired antigens H3 and H1 and comparable replication efficiency of the different viruses as judged from the very similar staining of EHV-1 gpII in all infected cells samples.

Expression of the transgenes in infected cells was analyzed by indirect immunofluorescence assay (IFA, not shown) and Western blot using commercially available monoclonal and polyclonal antibodies (FIG. 25). Restoration of orf71 encoding EHV-1 gpII was confirmed by IFA (not shown) and Western blot using a monoclonal antibody Ai2G7 (owned by BI), (FIG. 25).

Genetic and phenotypic stabilities of the recombinant rEHV-1 were shown by passaging in cell culture, determining viral titers every 5 passages. Sequences of the insertion regions were confirmed every ten passages as well as transgene expression by Western blot (not shown). Expression fidelity was assessed by double IFA of plaques under methocel-overlay, counting plaques stained with anti-EHV-antibodies and transgene-specific antibodies (not shown).

To investigate its properties as a vectored vaccine in young piglets, the tetravalent Swine IAV vaccine consisting of rEHV-1 RacH-SE_B and rEHV-1 RacH-SE_D is tested in a vaccination-challenge study. In detail, piglets with maternally derived immunity against Swine IAV (positive for maternal antibodies) are vaccinated twice with rEHV-1 RacH-SE_B and rEHV-1 RacH-SE_D at a dose of 1×10^7 TCID50 per vaccine strain intramuscularly at an age of one and four weeks (two-shot vaccination, 2×EHV-1) or at an age of four weeks only (one-shot vaccination, 1×EHV-1). A non-vaccinated group serves as negative control. At an age of 11 weeks, all animals but the negative control are challenged by an intratracheally applied dosage of 1×10^6 TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals serve as negative control, while non-vaccinated but challenged animals serve as challenge control. At and after vaccinations and before and after challenge, body temperatures are measured and blood samples are taken at different time points. One day after challenge, half of the animals per group are killed and the lungs are scored for lesions typical for Swine IAV infection, three lung samples per left and right lung are taken per animal, respectively, to determine infectious Swine IAV titers in lung homogenates, and bronchi alveolar lavage fluid (BALF) is sampled. The same procedure is performed with the remaining half on animals per group three days after challenge. Sample material and collected data is analyzed to determine, among others, body temperature changes after challenge, clinical signs after Swine IAV infection, lung scores, Swine IAV lung titers, histological changes in lung tissue, Swine IAV serum neutralization titers, cytokine levels in BALF, restimulation of PBMCS as measured by IFNγ-ELISpot, and B-cell activation.

Example 9

Induction of a Neutralizing Antibody Response Against Two Antigens in Mice Vaccinated with a Bivalent Rehv-1 Rach Vector Vaccine The rEHV-1 RacH SE_B (rEHV-1 RacH-SE-1/3-p430-H1av-7-p455-H3_see FIG. 15) was used for immunization of Balb/c mice in order to demonstrate that the expressed transgen RacH SE es are immunogenic in another species than swine and that neutralizing antibodies are induced against either one of the two antigens by intranasal application.

In detail, three groups of five Balb/c mice per group, 3-5 weeks of age, were intranasally inoculated on study days 0 and 21 either with 40 μl of rEHV-1 B (rEHV-1 RacH-SE-1/3-430-H1av-7-455-H3, group 1), or 40 μl of empty vector (rEHV-1 RacH-SE, group 2, vector control), or 40 μl of tissue culture medium (group 3 negative control), respectively. For groups 1 and 2, infectious recombinant EHV-1 dosages were 1×10^5 TCID50/40 μl, respectively. Mice were bled on study days 0 (before 1st inoculation), 7, 14, 21 (before 2nd inoculation), 28, and 35. Serum was prepared from the blood samples and stored frozen at −80° C.

Immunofluorescence Assay for Detection of Antibodies Against the Vector Virus

AI-ST cells were infected at a multiplicity of infection (MOI) of 0.001 with rEHV-1 RacH-SE1212, a virus rescued from the empty vector BAC pRacH-SE1.2. 24 hours p.i. distinctive plaques were observed and cells were processed for indirect immunofluorescence assay (IFA). Sera of all three groups of the final bleeds (obtained 14 days after the second vaccination) diluted 1:50 in PBS were tested. As positive control serum from an EHV-1 vaccinated horse was used in a dilution of 1:500. Secondary antibodies were commercially available FITC-conjugated rabbit anti-mouse IgG for the mice sera and Cy5-conjugated goat-anti horse IgG for the horse serum and used at 1:200 dilution. Antibody binding was evaluated by fluorescence microscopy. All vaccinated mice had developed antibodies reactive in IFA with rEHV-1 RacH-SE-infected cells. Uninfected cells were not bound by any of the tested sera. Sera from the negative control group of mice did not show any specific binding neither to infected nor to uninfected cells. Data are summarized in the table below.

TABLE 3

Fluorescence microscopy results of IFA for anti-EHV-1 antibodies

| Treatment | Mouse number | ID in experiment | dilution | Uninfected cells | Infected cells |
|---|---|---|---|---|---|
| Group 3 (Negative control) | 1 | 1 | 1:50 | neg | neg |
| | 2 | 2 | 1:50 | neg | neg |
| | 3 | 3 | 1:50 | neg | neg |
| | 4 | 4 | 1:50 | neg | neg |
| | 5 | 5 | 1:50 | neg | neg |
| Group 2 (Empty vector) | 1 | 6 | 1:50 | neg | pos |
| | 2 | 7 | 1:50 | neg | pos |
| | 3 | 8 | 1:50 | neg | pos |
| | 4 | 9 | 1:50 | neg | pos |
| | 5 | 10 | 1:50 | neg | pos |
| Group 1 (rEHV-1 RacH SE B) | 1 | 11 | 1:50 | neg | pos |
| | 2 | 12 | 1:50 | neg | pos |
| | 3 | 13 | 1:50 | neg | pos |
| | 4 | 14 | 1:50 | neg | pos |
| | 5 | 15 | 1:50 | neg | pos |

TABLE 3-continued

Fluorescence microscopy results of IFA for anti-EHV-1 antibodies

| Treatment | Mouse number | ID in experiment | dilution | Uninfected cells | Infected cells |
|---|---|---|---|---|---|
| Control antibody | Specific for | | | | |
| Horse serum | EHV-1 | 22 | 1:500 | neg | pos |
| Secondary antibodies | Specific for | | | | |
| FITC-goat anti- | mouse | 23 | 1:200 | neg | neg |
| Cy5 goat anti- | horse | 24 | 1:200 | neg | neg |

From this it can be concluded that inoculation of the rEHV-1 into the nostrils of the mice resulted in infection and viral replication, so that the mice immune systems were stimulated to produce anti-EHV-1 antibodies.

Virus Neutralization Tests

In order to show induction of protective immunity against the expressed transgenes originating either from Influenza A virus (IAV) (A/swine/Italy/7680/2001(H3N2)) or (A/swine/Gent/132/2005(H1N1)) the mice sera were tested for neutralizing activity against the respective viruses (Allwinn et al. 2010; Trombetta et al. 2014). IAV used for neutralization tests were isolates from pigs in Germany from 2014, specifically A/swine/Germany/AR452/2014 (H3N2) and A/swine/Germany/AR1181/2014 (H1N1). As these are heterologous from the strains the vaccine targets were derived from, any neutralization of these viruses by the mouse sera will be indicative of broad and efficient induction of protective immunity by the rEHV-1 vaccination.

As a negative control serum, a serum from a pig which had been shown to be negative for Influenza virus antibodies was used.

Influenza A Virus Neutralization Tests (VNT):

MDCK cells for virus neutralization as well as back-titration in 96-well plates were incubated for two days at 37° C./5% $CO_2$ prior to use. The respective IAV stocks H3N2 and H1 avN1 were thawed on ice and diluted in MEM containing Gentamycin and the double concentration of trypsin (MEM/Genta/2× trypsin).

Sera tested were from the final bleeds of group 1 (rEHV-1 RacH SE B), group 2 (empty vector), a positive control (serum from a pig vaccinated with inactivated multivalent IAV vaccine, and a negative control.

Sera were heat inactivated and in two and three independent tests, respectively, serially 1:2 diluted starting at 1:16 up to 1:4096. IAV was diluted to approximately 100 TCID50/neutralization reaction. Neutralization reactions were incubated for 2 hours at 37° C., 5% $CO_2$. Back-titration of used virus was done in quadruplicate. Growth medium was removed and MDCK-cells were washed with medium containing Gentamycin and trypsin before adding the neutralization reactions or the virus dilutions of the back-titrations. VNT and titration plates were incubated at 37° C./5% $CO_2$ for 1 h after addition of neutralization reaction or virus dilutions to the MDCK-cells, respectively. Thereafter inocula were removed and cells were overlaid with fresh medium containing Gentamycin and trypsin. Five days p.i. CPE was monitored and documented. Actually used virus titer in the test was calculated as TCID50/ml according to Reed and Munch and dilutions at which the tested sera prevented induction of Influenza virus-typical CPE were reported, see tables below.

TABLE 4

| Results Influenza H1avN1 VNT | | | | | | | | |
|---|---|---|---|---|---|---|---|---|
| | H1avN1 | | | | | | | |
| | VNT#1 | | VNT#2 | | VNT#3 | | | |
| mouse | 146 TCID50/well Reciprocal neutralizing dilution | capacity | 32 TCID50/well Reciprocal neutralizing dilution | capacity | 181 TCID50/well Reciprocal neutralizing dilution | capacity | Average neutralizing capacity | SD (standard deviation) |
| rEHV-1 RacH SE B-1 | 32 | 4672 | 128 | 4096 | 32 | 5792 | 4853 | 862 |
| rEHV-1 RacH SE B-2 | 16 | 2336 | 64 | 2048 | neg | | 2192 | 204 |
| rEHV-1 RacH SE B-3 | 32 | 4672 | 128 | 4096 | 16 | 2896 | 3888 | 906 |
| rEHV-1 RacH SE B-4 | 128 | 18688 | 512 | 16384 | 64 | 11584 | 15552 | 3624 |
| rEHV-1 RacH SE B-5 | 32 | 4672 | 256 | 8192 | 16 | 2896 | 5253 | 2695 |
| Empty vector-1 | n.d. | n/a | neg | n/a | neg | n/a | n/a | n/a |
| Empty vector-2 | n.d. | n/a | neg | n/a | neg | n/a | n/a | n/a |
| Empty vector-3 | n.d. | n/a | neg | n/a | neg | n/a | n/a | n/a |
| Empty vector-4 | neg | n/a | neg | n/a | neg | n/a | n/a | n/a |
| Empty vector-5 | n.d. | n/a | neg | n/a | neg | n/a | n/a | n/a |
| Pos control pig serum | 32 | n/a | n.d | n/a | n.d | n/a | n/a | n/a |

TABLE 5

| Results Influenza H3N2 VNT | | | | | | | | |
|---|---|---|---|---|---|---|---|---|
| | H3N2 | | | | | | | |
| | VNT#1 | | VNT#2 | | VNT#3 | | | |
| mouse | 16 TCID50/well Reciprocal neutralizing dilution | capacity | 24 TCID50/well Reciprocal neutralizing dilution | capacity | 15 TCID50/well Reciprocal neutralizing dilution | capacity | Average neutralizing capacity | SD (standard deviation) |
| rEHV-1 RacH SE B-1 | 4096 | 65536 | 1024 | 24576 | 2048 | 30720 | 40277 | 22089 |
| rEHV-1 RacH SE B-2 | 1024 | 16384 | 512 | 12288 | 128 | 1920 | 10197 | 7455 |
| rEHV-1 RacH SE B-3 | 1024 | 16384 | 512 | 12288 | 256 | 3840 | 10837 | 6397 |
| rEHV-1 RacH SE B-4 | 256 | 4096 | 256 | 6144 | 64 | 960 | 3733 | 2611 |
| rEHV-1 RacH SE B-5 | 256 | 4096 | 128 | 3072 | 64 | 960 | 2709 | 1599 |
| Empty vector-1 | neg | n/a | neg | n/a | neg | n/a | n/a | n/a |

TABLE 5-continued

| Results Influenza H3N2 VNT | | | | | | | | |
|---|---|---|---|---|---|---|---|---|
| | H3N2 | | | | | | | |
| | VNT#1 | | VNT#2 | | VNT#3 | | | |
| mouse | 16 TCID50/well Reciprocal neutralizing dilution | capacity | 24 TCID50/well Reciprocal neutralizing dilution | capacity | 15 TCID50/well Reciprocal neutralizing dilution | capacity | Average neutralizing capacity | SD (standard deviation) |
| Empty vector-2 | neg | n/a | neg | n/a | neg | n/a | n/a | n/a |
| Empty vector-3 | neg | n/a | neg | n/a | neg | n/a | n/a | n/a |

Figure 26:
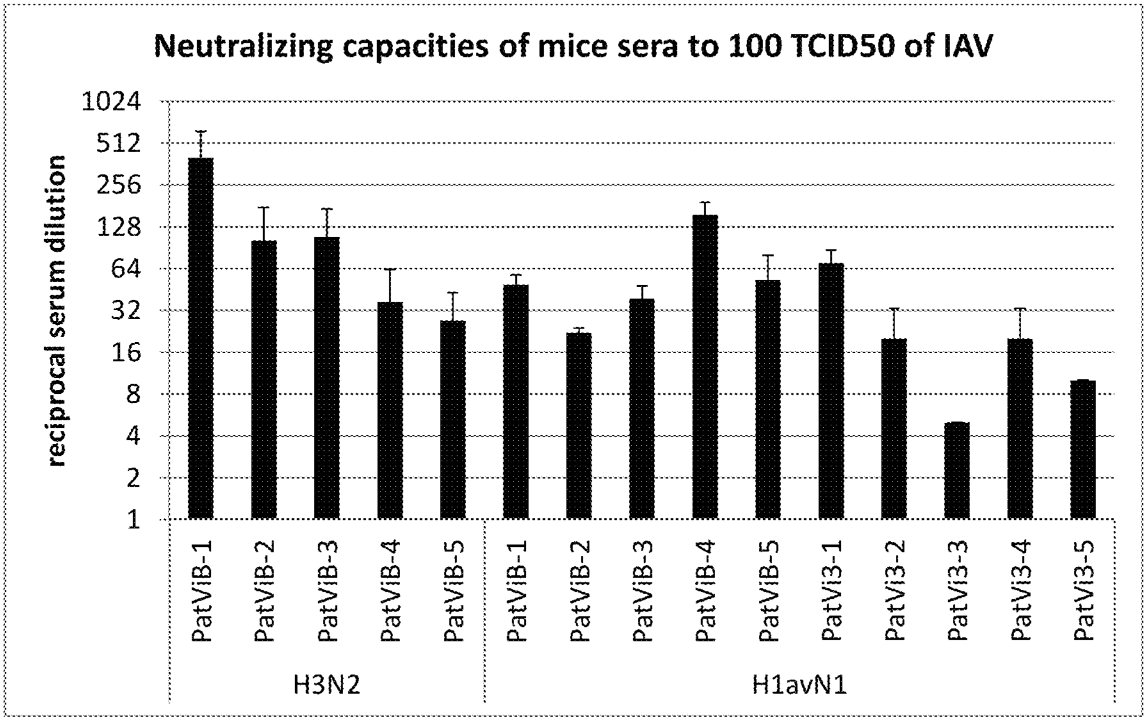
FIG. 26: Graphical representation of average neutralizing capacities of mice sera against Influenza A viruses (A/swine/Italy/7680/2001(H3N2)) or (A/swine/Gent/132/2005 (H1N1)). Neutralizing capacity was calculated by multiplication of the reciprocal serum dilution and the respective titer that was neutralized by it. Averages of three tests were then divided by 100 to reflect neutralization of 100 TCID50. Error bars indicate standard deviation.

In order to compare results of independent tests neutralizing capacity was calculated by multiplication of the reciprocal serum dilution and the respective titer that was neutralized by it. Averages of three tests were then divided by 100 to reflect neutralization of 100 TCID50 (Tables 3, 4 and 5). Data are summarized and shown graphically in FIG. 26.

All mice vaccinated with rEHV-1 RacH SE B had developed neutralizing antibodies against the respective IAV, heterologous strains of subtypes H3N2 and H1avN1. Thus, twofold intranasal application of rEHV-1 RacH-SE expressing hemagglutinins of IAV from the orf70 insertion site under control of the p455 promoter (H3) and in parallel from the orf1/3 insertion site under control of the p430 promoter (H1av), successfully stimulated protective immune response in BALB/c mice.

It can be concluded that the vector rEHV-1 RacH-SE can be used for parallel expression of two different transgenes to stimulate immune response after intranasal vaccination.

Example 10

Efficacy of Tetravalent Swine IAV Vaccine Consisting of rEHV-1 RacH-SE_B and rEHV-1 RacH-SE_D Against Swine IAV H3N2 Challenge in Piglets To investigate its properties as a vectored vaccine in young piglets, the tetravalent Swine IAV vaccine consisting of rEHV-1 RacH-SE_B (rEHV-1 RacH-SE-1/3-p430-H1av-70-p455-H3, see FIG. 15) and rEHV-1 RacH-SE_D (rEHV-1 RacH-SE-1/3-p430-H1hu-70-p455-H1pdm, see FIG. 24) was tested in a second vaccination-challenge study.

In this second study, piglets from unvaccinated sows and tested serologically negative for swine IAV-specific antibodies by use of an H3-specific ELISA (FIG. 30) and by virus neutralization test (data not shown) at the time of first vaccination were vaccinated twice with the tetravalent vaccine consisting of rEHV-1 RacH-SE_B and rEHV-1 RacH-SE_D. Animals were vaccinated the first time in their first week of life (study day 0, SD0) and the second time in their fourth week of life (study day 21, SD21), respectively, either intramuscularly and then intramuscularly (2×IM), or first intranasally and then intramuscularly (IN+IM), or twice intranasally (2×IN), at a dose of 1×10^7 TCID50 in a 2 ml dose per vaccine strain, animal, and vaccination, respectively. A non-vaccinated group served as negative control and another non-vaccinated group served as challenge control. In their seventh week of life (study days 69 or 70, SD42/43), all animals but the negative control were challenged by an intratracheally applied dosage of 2×10^7 TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals served as negative control (neg. ctrl.), while non-vaccinated but challenged animals served as challenge control (chall. ctrl.). At and after vaccinations and before challenge, blood samples were taken at different time points.

Figure 27:
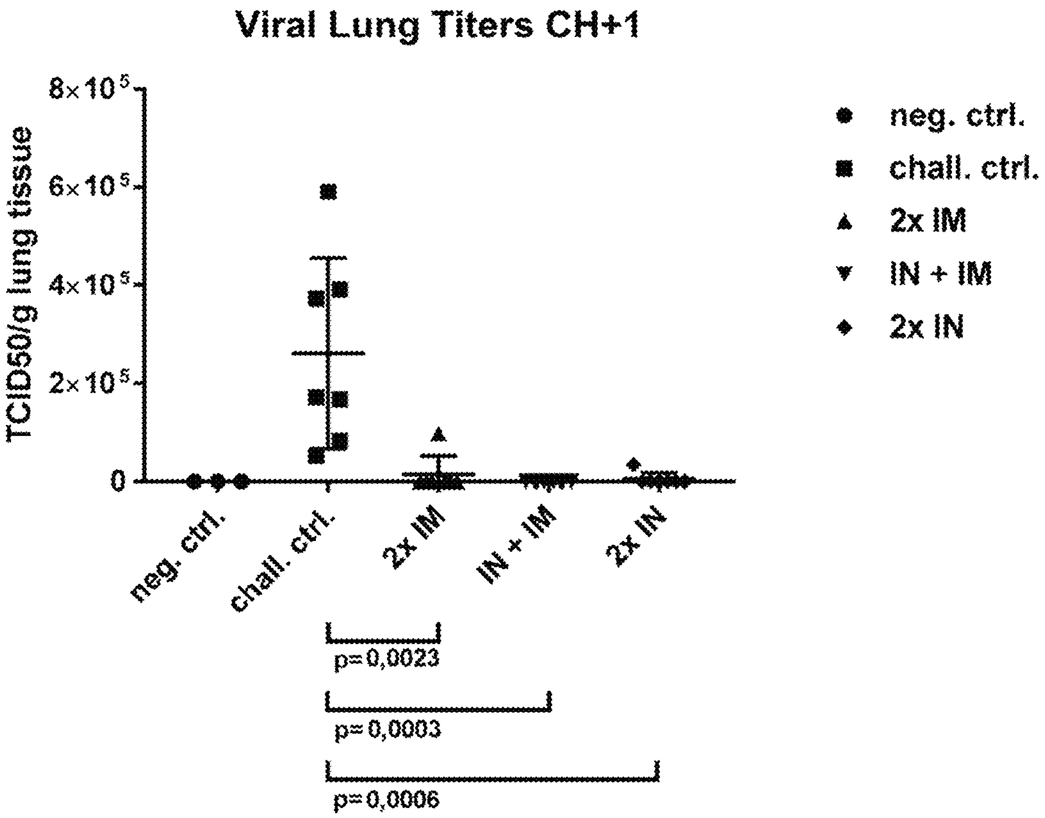
FIG. 27: Swine IAV lung titers determined as TCID50/g lung tissue for animals killed one day after challenge. neg. ctrl., negative control group; chall. ctrl., challenge control group; 2×IM, group vaccinated two times intramuscularly; IN+IM, group vaccinated first intranasally and second intramuscularly; 2×IN, group vaccinated two times intranasally. Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GRAPHPAD PRISM® for Windows software 7.02, GraphPad Software, Inc., La Jolla, Calif. 92037, USA, using standard software settings, respectively.
Figure 28:
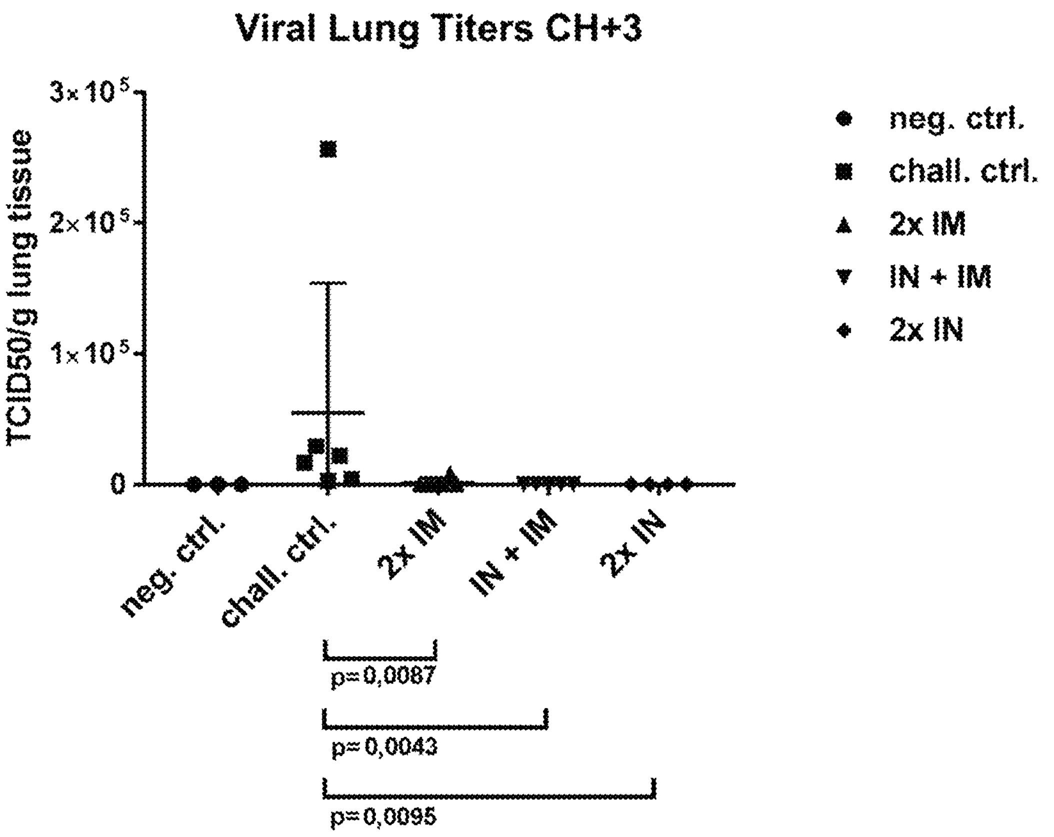
FIG. 28: Swine IAV lung titers determined as TCID50/g lung tissue for animals killed three days after challenge. neg. ctrl., negative control group; chall. ctrl., challenge control group; 2×IM, group vaccinated two times intramuscularly; IN+IM, group vaccinated first intranasally and second intramuscularly; 2×IN, group vaccinated two times intranasally. Data points indicate means obtained for individual animals. Middle horizontal lines indicate group means, respectively. Upper and lower horizontal lines indicate standard deviations, respectively. p values for pairwise statistical comparisons of groups are given below and were calculated by t-test using the Mann-Whitney test and GraphPad Prism® for Windows software 7.02, GraphPad Software, Inc., La Jolla, Calif. 92037, USA, using standard software settings, respectively.

One day after challenge, half of the animals per group were killed and three lung samples per left and per right lung were taken per animal, respectively. Then, infectious swine IAV titers per gram lung homogenate were determined for each animal as an average of the left and right lungs per animal that each were obtained from homogenates of the pooled three samples per left or right lung and that were normalized to the total weight of the three samples of the left or the right lung, respectively. The same procedure was performed with the remaining half of animals per group three days after challenge. For all vaccinated groups, the medians of titers of infectious swine IAV obtained from individual animals in the group were statistically significantly reduced for samples taken at day one after challenge (CH+1) when compared to the challenge control group, while all animals from the negative control group showed no infectious swine IAV virus titers in their lung homogenates (FIG. 27). Moreover, for all vaccinated groups, the medians of titers of infectious swine IAV obtained from individual animals in the group were statistically significantly reduced for samples taken at day 3 after challenge (CH+3) when compared to the challenge control group, while all animals from the negative control group showed no infectious swine IAV virus titers in their lung homogenates (FIG. 28). Thus, vaccination with the tetravalent swine IAV vaccine consisting of rEHV-1 RacH-SE_B and rEHV-1 RacH-SE_D statistically significantly reduced the swine IAV lung loads at one and three days after challenge with a heterologous swine IAV H3N2 strain in piglets, respectively. Consequently, the vaccine described here is efficacious against swine IAV in pigs.

Moreover, serum taken from study animals at study day 0 (SD0, before first vaccination), at study day 21 (SD21, before second vaccination), and at study days 42 or 43 (SD42/43, before application of challenge material) was analyzed by an enzyme-linked immunosorbent assay (ELISA) specific for swine immunoglobulin G (IgG) directed against a recombinantly expressed swine IAV H3 antigen being homologous to the H3 expressed by vaccine strain rEHV-1 RacH-SE_B. While mean OD values of sera from the negative control group gave only very low values for all time points measured, sera from vaccinated groups demonstrated a strong increase of OD values after two intramuscular applications (2×IM; SD21 and SD42/43), after first intranasal and then intramuscular application (IN+IM; SD42/43), and after two intranasal applications (2×IN; SD42/43); FIG. 30. Thus, vaccination with the tetravalent swine IAV vaccine consisting of rEHV-1 RacH-SE_B and rEHV-1 RacH-SE_D elicited a serological immune response in piglets against the swine IAV hemagglutinin H3 expressed by vaccine strain rEHV-1 RacH-SE_B, respectively.

In addition, peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 μg/ml (rH3 1 μg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively (FIG. 32). While restimulated PBMCs from the challenge control group (served as negative control for this test, animals were not vaccinated) showed mean spots per group of below 45 after either of the restimulations, restimulated PBMCs from vaccinated animals showed mean spots per group of above 85 after two intramuscular applications, of more than 100 spots after first intranasal and then intramuscular application (IN+IM), and of more than 150 spots after two intranasal applications (2×IN), after either of the restimulations, respectively (FIG. 32). Thus, vaccination with the tetravalent swine IAV vaccine consisting of rEHV-1 RacH-SE_B and rEHV-1 RacH-SE_D elicited a cellular immune response in piglets both against the swine IAV hemagglutinin H3 expressed by vaccine strain rEHV-1 RacH-SE_B and against the swine IAV H3N2 R452-14 used for heterologous challenge virus infection, respectively.

Thus, vaccination of piglets with tetravalent Swine IAV vaccine consisting of rEHV-1 RacH-SE_B and rEHV-1 RacH-SE_D induced a detectable serological and cellular immune response in piglets and demonstrated vaccine efficacy by statistically significantly reducing swine IAV loads in lung homogenates one and three days after heterologous swine IAV challenge.

Example 11

Efficacy of Tetravalent Swine IAV Vaccine Consisting of rEHV-1 RacH-SE_B and rEHV-1 RacH-SE_D Against Swine IAV H3N2 Challenge in Piglets with Maternally Derived Antibodies To investigate its properties as a vectored vaccine in young piglets, the tetravalent Swine IAV vaccine consisting of rEHV-1 RacH-SE_B and rEHV-1 RacH-SE_D was tested in a third vaccination-challenge study.

In this third study, piglets born by and colostrum- and milk-fed by sows that were vaccinated twice during pregnancy with a commercially available inactivated vaccine against swine IAV were used. Piglets were tested serologically positive for swine IAV-specific antibodies by use of a H3-specific ELISA (FIG. 31) and by use of a commercially available swine IAV-specific antibody ELISA (IDEXX Influenza A (Virus Antibody Test)®; IDEXX, Westbrook, Me. 04092, USA) following the manufacturer's testing recommendations (data not shown) at the time of first vaccination were vaccinated twice with the tetravalent vaccine consisting of rEHV-1 RacH-SE_B and rEHV-1 RacH-SE_D. Animals were vaccinated the first time in their first week of life (study day 0, SD0) and the second time in their fourth week of life (study day 21, SD21), respectively, either intramuscularly and then intramuscularly (2×IM), or first intranasally and then intramuscularly (IN+IM), or twice intranasally (2×IN), at a dose of 1×10^7 TCID50 in a 2 ml dose per vaccine strain, animal, and vaccination, respectively. A non-vaccinated group served as negative control and another non-vaccinated group served as challenge control. In their eleventh week of life (study days 69 or 70, SD69/70), all animals but the negative control were challenged by an intratracheally applied dosage of 2×10^7 TCID50 of an H3N2 Swine IAV challenge strain (European field virus isolate R452-14 whose H3 is being heterologous to the H3 vaccine antigen used in rEHV-1 RacH-SE_B). Non-vaccinated and unchallenged animals served as negative control (neg. ctrl.), while non-vaccinated but challenged animals served as challenge control (chall. ctrl.). At and after vaccinations and before challenge, blood samples were taken at different time points.

Figure 29:
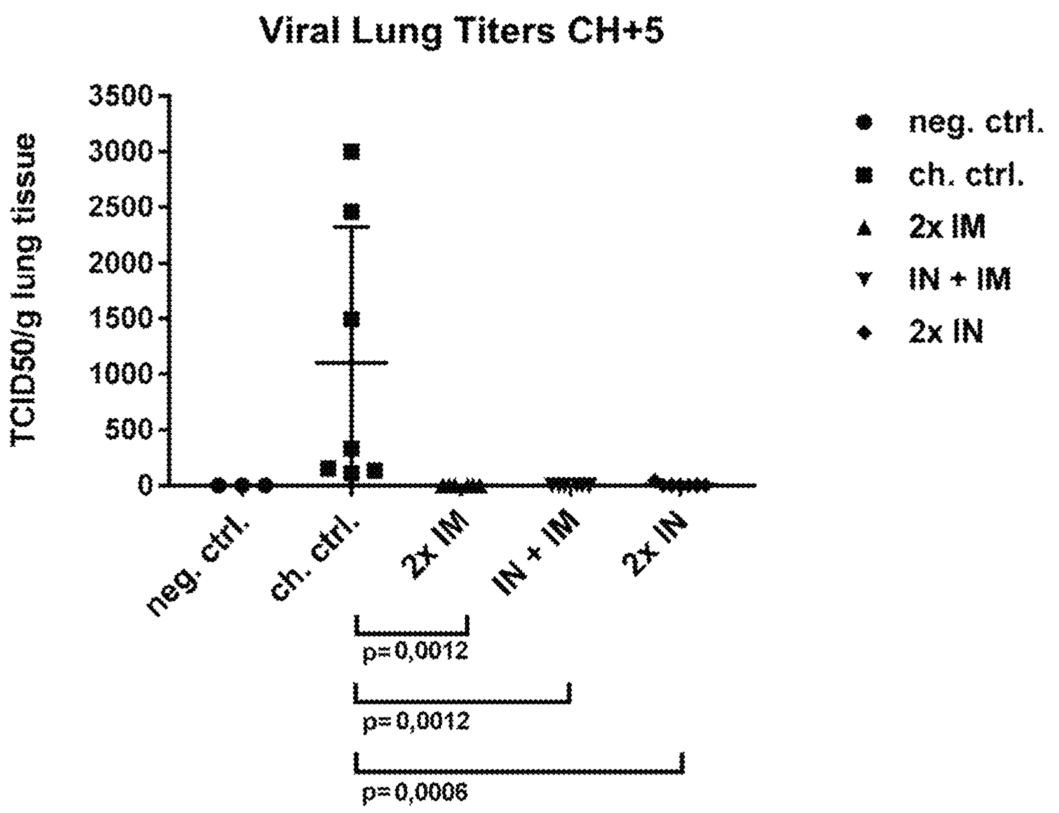
FIG. 29: Swine IAV lung titers determined as TCID50/g lung tissue for animals killed five days after challenge. neg. ctrl., negative control group; chall. ctrl., challenge control group; 2×IM, group vaccinated two times intramuscularly; IN+IM, group vaccinated first intranasally and second intramuscularly; 2×IN, group vaccinated two times intranasally.

Five days after challenge animals were killed and three lung samples per left and per right lung were taken per animal, respectively. Then, infectious swine IAV titers per gram lung homogenate were determined for each animal as an average of the left and right lungs per animal that each were obtained from homogenates of the pooled three samples per left or right lung and that were normalized to the total weight of the three samples of the left or the right lung, respectively. For all vaccinated groups, the medians of titers of infectious swine IAV obtained from individual animals in the group were statistically significantly reduced for samples taken at day five after challenge (CH+5) when compared to the challenge control group, while all animals from the negative control group showed no infectious swine IAV virus titers in their lung homogenates (FIG. 29). Thus, vaccination with the tetravalent swine IAV vaccine consisting of rEHV-1 RacH-SE_B and rEHV-1 RacH-SE_D statistically significantly reduced the swine IAV lung loads at five days after challenge with a heterologous swine IAV H3N2 strain in piglets, respectively. Consequently, the vaccine described here is efficacious against swine IAV in pigs.

Moreover, serum taken from study animals at study day 0 (SD0, before first vaccination), at study day 21 (SD21, before second vaccination), and at study day 35 (SD35, two weeks after second vaccination) was analyzed by an enzyme-linked immunosorbent assay (ELISA) specific for swine immunoglobulin G (IgG) directed against a recombinantly expressed swine IAV H3 antigen being homologous to the H3 expressed by vaccine strain rEHV-1 RacH-SE_B. While mean OD values of sera from the negative control group gave only very low values for SD21 and SD35, sera from vaccinated groups demonstrated a strong increase of OD values after two intramuscular applications (2×IM; SD35), after first intranasal and then intramuscular application (IN+IM; SD35), and after two intranasal applications (2×IN; SD35); FIG. 31. Thus, vaccination with the tetravalent swine IAV vaccine consisting of rEHV-1 RacH-SE_B and rEHV-1 RacH-SE_D elicited a serological immune response in piglets against the swine IAV hemagglutinin H3 expressed by vaccine strain rEHV-1 RacH-SE_B, respectively.

In addition, peripheral blood mononuclear cells (PBMCs) were purified from blood taken from study animals at study day 28 (SD28). The PBMCs then were restimulated either with H3N2 swine IAV challenge strain R452-14 at a multiplicity on infection of 1 (H3N2 MOI 1) or with recombinantly expressed swine IAV H3 antigen being homologous to the H3 expressed by vaccine strain rEHV-1 RacH-SE_B at a concentration of 1 μg/ml (rH3 1 μg/ml). Using the restimulated PBMCs, an interferon gamma-specific enzyme-linked immunosorbent spot assay (IFNγ ELISpot) was performed, and the obtained values normalized to 10^6 cells and calculated as means per group, respectively (FIG. 33). While restimulated PBMCs from the challenge control group (served as negative control for this test, animals were not vaccinated) showed mean spots per group of below 15 after either of the restimulations, restimulated PBMCs from vaccinated animals showed mean spots per group of above 30 after two intramuscular applications, of more than 55 spots after first intranasal and then intramuscular application (IN+IM), and of more than 65 spots after two intranasal applications (2×IN), after either of the restimulations, respectively (FIG. 33). Thus, vaccination with the tetravalent swine IAV vaccine consisting of rEHV-1 RacH-SE_B and rEHV-1 RacH-SE_D elicited a cellular immune response in piglets both against the swine IAV hemagglutinin H3 expressed by vaccine strain rEHV-1 RacH-SE_B and against the swine IAV H3N2 R452-14 used for heterologous challenge virus infection, respectively.

Thus, vaccination of piglets with tetravalent Swine IAV vaccine consisting of rEHV-1 RacH-SE_B and rEHV-1 RacH-SE_D induced a detectable serological and cellular immune response in piglets and demonstrated vaccine efficacy by statistically significantly reducing swine IAV loads in lung homogenates five days after heterologous swine IAV challenge.

Example 12

The Tetravalent Swine IAV Vaccine Consisting of rEHV-1 RacH-SE_B and rEHV-1 RacH-SE_D Provides a Diagnostic Differentiation of Infected from Vaccinated Animals (DIVA) Feature Based on IAV Nucleoprotein (NP)-Specific Antibodies To assess the serological DIVA properties of the tetravalent Swine IAV vaccine consisting of rEHV-1 RacH-SE_B and rEHV-1 RacH-SE_D, piglets born by and colostrum- and milk-fed by sows that were vaccinated twice during pregnancy with a commercially available inactivated vaccine against swine IAV were vaccinated twice with the tetravalent vaccine consisting of rEHV-1 RacH-SE_B and rEHV-1 RacH-SE_D. Animals were vaccinated the first time in their first week of life and the second time in their fourth week of life, respectively, either intramuscularly and then intramuscularly (2×IM), or first intranasally and then intramuscularly (IN+IM), or twice intranasally (2×IN), at a dose of 1×10^7 TCID50 in a 2 ml dose per vaccine strain, animal, and vaccination, respectively. A non-vaccinated group served as negative control (neg. ctrl.). For the 2×IM, IN+IM, 2×IN, and neg. ctrl. groups, five animals per group were used and serum samples were taken before first vaccination (FIG. 34, before vaccination) and 14 days after second vaccination (FIG. 34, after vaccination), respectively. As a positive control, two piglets from unvaccinated sows which were tested negative for IAV specific antibodies before the time point of first vaccination (data not shown and FIG. 34, before vaccination) were vaccinated twice with a commercially available inactivated IAV containing vaccine against swine IAV (pos. ctrl.). The pos. ctrl. piglets were vaccinated for the first time in their second week of life and for the second time in their fifth week of life, respectively, and serum samples were taken before the first vaccination (FIG. 34, before vaccination) and 22 days after second vaccination (FIG. 34, after vaccination), respectively.

The sera described above were tested in an ELISA detecting swine IAV nucleoprotein (NP)-specific IgG (FIG. 34). The serum samples from piglets of vaccinated sows (neg. ctrl., 2×IM, IN+IM, 2×IN groups) all showed mean OD values per group of 0.7 or higher before vaccination, thus demonstrating presence of IAV NP-specific antibodies in these non-vaccinated animals of maternally-derived origin (FIG. 34). In contrast, the mean group value of piglet sera from the pos. ctrl. group was below 0.15 before vaccination, demonstrating absence/very low levels of IAV NP-specific antibodies. At 22 days after second vaccination (FIG. 34, after vaccination) with a commercially available inactivated NP-containing swine IAV vaccine, the mean group value of sera from the pos. ctrl. group increased to more than 1.9, thus demonstrating the strong induction of detectable swine IAV NP-specific IgG in piglets. In contrast, at 14 days after vaccination with the tetravalent swine IAV vaccine consisting of rEHV-1 RacH-SE_B and rEHV-1 RacH-SE_D which does not contain nor express swine IAV NP, the serum samples from piglets of the 2×IM, IN+IM, 2×IN groups and also from the non-vaccinated neg. ctrl. group showed mean OD values per group of below 0.15, respectively, thus demonstrating decline of IAV NP-specific antibody levels present before vaccination to very low levels and that vaccination did not result in a strong induction of detectable swine IAV NP-specific IgG in piglets. Taken together, while the conventional NP-containing inactivated swine IAV vaccine led to a strong induction of detectable NP-specific antibodies in vaccinated piglets, vaccinations with the tetravalent swine IAV vaccine consisting of rEHV-1 RacH-SE_B and rEHV-1 RacH-SE_D did not induce a strong induction of detectable NP-specific antibodies in vaccinated piglets.

The fact that the tetravalent swine IAV vaccine consisting of rEHV-1 RacH-SE_B and rEHV-1 RacH-SE_ D did not induce a strong induction of detectable NP-specific antibodies in vaccinated piglets demonstrated a serological diagnostic marker allowing a differentiation of infected from vaccinated animals (DIVA) and a differentiation of vaccinated animals from animals that were vaccinated with a conventional NP-containing inactivated swine IAV vaccine.

This DIVA feature is exploited for commercial test development accompanying the use of the tetravalent swine IAV vaccine consisting of rEHV-1 RacH-SE_B and rEHV-1 RacH-SE_D and to support eradication measures against swine IAV.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

1. Allwinn R, Geiler J, Berger A, Cinatl J, Doerr H W. 2010. Determination of serum antibodies against swine-origin influenza A virus H1N1/09 by immunofluorescence, haemagglutination inhibition, and by neutralization tests: how is the prevalence rate of protecting antibodies in humans? Med Microbiol Immunol. 199(2):117-21. doi: 10.1007/s00430-010-0143-4. Epub 2010 Feb. 17.
2. Boshart M, Weber F, Jahn G, Dorsch-Häsler K, Fleckenstein B, Schaffner W. 1985. A very strong enhancer is located upstream of an immediate early gene of human cytomegalovirus. Cell 41(2):521-30. A very strong enhancer is located upstream of an immediate early gene of human cytomegalovirus Author links open the overlay panel.
3. Brown, I. H., Chakraverty P., Harris P. A., Alexander D. J. 1995. Disease outbreaks in pigs in Great Britain due to an influenza A virus of H1N2 subtype. Vet Rec., (13): 328-9.
4. Brown I H. The epidemiology and evolution of influenza viruses in pigs. 2000. Vet Microbiol., 74(1-2):29-46
5. Bryant, N. A., Davis-Poynter, N., Vanderplasschen, A., and Alcami, A. 2003. Glycoprotein G isoforms from some alpha herpesviruses function as broad-spectrum chemokine binding proteins. The EMBO Journal Vol. 22 (4): 833-846.
6. Bustin, S. 2000. Absolute quantification of mRNA using real-time reverse transcription polymerase chain reaction assays. Journal of Molecular Endocrinology 25(2): 169-193.
7. Colle, C. F. 3rd, O'Callaghan, D. J. 1995. Transcriptional analyses of the unique short segment of EHV-1 strain Kentucky A. Virus Genes; 9(3):257-68.
8. Dorsch-Häsler, K., Keil, G. M., Weber, F., Jasin, M. Schaffner, W., and Koszinowski, U. H. 1985. A long and complex enhancer activates transcription of the gene coding for the highly abundant immediate early mRNA in murine cytomegalovirus. PNAS Vol. 82: 8325-8329.
9. Drummer, H. E., Studdert, M. J., Crabb, B. S. 1998. Equine herpesvirus-4 glycoprotein G is secreted as a disulphide-linked homodimer and is present as two homodimeric species in the virion. J. Gen. Virol. 79: 1205-1213
10. Goodwin, E. C. & Rottman, F. M. 1992. The 3' flanking sequence of the bovine growth hormone gene contains novel elements required for efficient and accurate polyadenylation. J. Biol. Chem. 267: 16330-16334.
11. Hübert, P. H., Birkenmaier, S., Rziha, H.-J. and Osterrieder, N. (1996), Alterations in the Equine Herpesvirus Type-1 (EHV-1) Strain RacH During Attenuation. Journal of Veterinary Medicine, Series B, 43: 1-14. doi:10.1111/j.1439-0450.1996.tb00282.x
12. Luke, G A and Ryan, M D. 2013. The protein coexpression problem in biotechnology and biomedicine: virus 2A and 2A-like sequences provide a solution. Future Virology, Vol. 8, No. 10, Pages 983-996.
13. Ma, G., Eschbaumer, M., Said, A., Hoffmann, B., Beer, M., Osterrieder, N. 2012. An equine herpesvirus type 1 (EHV-1) expressing VP2 and VP5 of serotype 8 bluetongue virus (BTV-8) induces protection in a murine infection model. PLoS One. 2012; 7(4):e34425. doi: 10.1371/journal.pone.0034425. Epub 2012 Apr. 12
14. Ma, G., Azab, W., Osterrieder, N. 2013. Equine herpesviruses type 1 (EHV-1) and 4 (EHV-4)—masters of co-evolution and a constant threat to equids and beyond. Vet Microbiol. 167(1-2):123-34.
15. Nolan, T. Rebecca E Hands, R. E., and Bustin S. A. 2006. Quantification of mRNA using real-time RT-PCR Nature Protocols 1: 1559-1582
16. Osterrieder, N., Neubauer, A., Brandmüller, C., Kaaden, O. R., and O'Callaghan, D. J. 1996. The equine herpesvirus 1 IR6 protein influences virus growth at elevated temperature and is a major determinant of virulence. Virology 226:243-251.
17. Ptashne, M. 2014. The Chemistry of Regulation of Genes and Other Things The Journal of Biological Chemistry Vol. 289, (9) 5417-5435. Reed, L. J., and Muench, H. 1938. A simple method of estimating fifty percent endpoints. Am. J. Hyg. (27) 3; 493-497.
18. Rajao D S, Sandbulte M R, Gauger P C, Kitikoon P, Platt R, Roth J A, Perez D R, Loving C L, Vincent A L. 2016. Heterologous challenge in the presence of maternally-derived antibodies results in vaccine-associated enhanced respiratory disease in weaned piglets. Virology. 2016 April; 491:79-88.
19. Rosas, C. T., Konig, P., Beer, M., Dubovi, E. J., Tischer, B. K., Osterrieder, N., 2007a. Evaluation of the vaccine potential of an equine herpesvirus type 1 vector expressing bovine viral diarrhea virus structural proteins. J. Gen. Virol. 88 (3), 748-757.
20. Rosas, C. T., B. K. Tischer, G. A. Perkins, B. Wagner, L. B. Goodman, N. Osterrieder. 2007b. Live-attenuated recombinant equine herpesvirus type 1 (EHV-1) induces a neutralizing antibody response against West Nile virus (WNV) Virus Research, 125, pp. 69-78.
21. Rosas, C. T., Van de Walle, G. R., Metzger, S. M., Loelzer, K., Dubovi, E. J., Kim, S. G., Parrish, C. R., Osterrieder, N., 2008. Evaluation of a vectored equine herpesvirus type 1 (EHV-1) vaccine expressing H3 hemagglutinin in the protection of dogs against canine influenza. Vaccine 26 (19), 2335-3234.
22. Said, A., Elke Lange, E., Beer, M. Damiani, A., Osterrieder, N. 2013. Recombinant equine herpesvirus 1 (EHV-1) vaccine protects pigs against challenge with influenza A(H1N1)pmd09 Virus Research 173: 371-376
23. Shaner, N.C., Campbell, R. E., Steinbach, P. A., Giepmans, B. N., Palmer, A. E., Tsien, R, Y. 2004. Improved monomeric red, orange and yellow fluorescent proteins derived from Discosoma sp. red fluorescent protein. Nat Biotechnol. December; 22(12):1567-72. Epub 2004 Nov. 21.
24. Thacker, E. and Janke, B. 2008. Swine Influenza Virus: Zoonotic Potential and Vaccination Strategies for the Control of Avian and Swine Influenzas J Infect Dis. (2008) 197 (Supplement 1): S19-S24 doi:10.1086/524988
25. Tischer, B. K, Smith, G. A., and Osterrieder, N. in: Jeff Braman (ed.), In Vitro Mutagenesis Protocols: Third Edition, Methods in Molecular Biology, vol. 634, DOI 10.1007/978-1-60761-652-8_30, © Springer Science+Business Media, LLC 2010, Chapter 30: En Passant Mutagenesis: A Two Step Markerless Red Recombination System.
26. Tischer, B. K., von Einem, J., Kaufer, B., Osterrieder, N., 2006. Two-step red-mediated recombination for versatile high-efficiency markerless DNA manipulation in *Escherichia coli*. Biotechnol. Tech. 40, 191-197.

27. Trapp, S., von Einem, J., Hofmann, H., Kostler, J., Wild, J., Wagner, R., Beer, M., Osterrieder, N., 2005. Potential of equine herpesvirus 1 as a vector for immunization. J. Virol. 79, 5445-5454.

28. Trombetta C M, Perini D, Mather S, Temperton N, Montomoli E. 2014. Overview of Serological Techniques for Influenza Vaccine Evaluation: Past, Present and Future. Vaccines (Base1) 13; 2(4):707-34. doi: 10.3390/vaccines2040707.

29. Watson S. J., Langat P., Reid S. M., Lam T. T., Cotten M., Kelly M., Van Reeth K., Qiu Y., Simon G., Bonin E., Foni E., Chiapponi C., Larsen L., Hjulsager C., Markowska-Daniel I., Urbaniak K., Dürrwald R., Schlegel M., Huovilainen A., Davidson I., Dán Á., Loeffen W., Edwards S., Bublot M., Vila T., Maldonado J., Valls L.; ESNIP3 Consortium, Brown I. H., Pybus O. G., Kellam P. Molecular Epidemiology and Evolution of Influenza Viruses Circulating within European Swine between 2009 and 2013. 2015, *J Virol*. October; 89(19):9920-31.

What is claimed is:

1. An EHV-1 RacH vector comprising a first and a second exogenous antigen encoding sequence relating to a pathogen infecting food producing animals, wherein the first exogenous antigen encoding sequence is inserted into ORF70, wherein the ORF70 is modified by deleting an approximately 801 bp portion, wherein the deletion corresponds to a sequence having at least 95% sequence homology with SEQ ID NO: 20, and wherein the second exogenous antigen encoding sequences is inserted into an insertion site, and wherein said exogenous antigen encoding sequences are operably linked to promoters.

2. The EHV-1 RacH vector of claim 1, wherein the first and/or the second exogenous antigen encoding sequence is an influenza hemagglutinin encoding sequence.

3. The influenza hemagglutinin encoding sequence of claim 2, wherein the hemagglutinin influenza subtype is H1 and/or H3.

4. The EHV-1 RacH vector of claim 1, wherein the first and/or the second exogenous antigen encoding sequence encodes a hemagglutinin influenza antigen having at least 95% sequence identity with any one of SEQ ID NOs:26, 27, 28, and 29.

5. The EHV-1 RacH vector of claim 1, wherein the insertion site of the second exogenous antigen encoding sequence is ORF1/3 or ORF70.

6. The EHV-1 RacH vector of claim 1, wherein the second exogenous antigen encoding sequence is inserted into ORF1/3.

7. The EHV-1 RacH vector of claim 1, wherein the ORF70 has a partial deletion, truncation, substitution, or modification, and wherein ORF71 remains functional, and wherein the ORF70 gene product glycoprotein G expression has been abolished.

8. The EHV-1 RacH vector of claim 1, wherein the EHV-1 RacH vector comprises at least one flanking region with sequence comprising any one of SEQ ID NOs: 13, 14, 15, 16, 17, and 18.

9. The EHV-1 RacH vector of claim 1, wherein at least one of the promoters is SV40 large T, HCMV and MCMV immediate early gene 1, human elongation factor alpha promoter, baculovirus polyhedrin promoter, or a sequence having at comprising any one of SEQ ID Nos: 1, 2, 3, and 4, or the complementary nucleotide sequences thereof.

10. The EHV-1 RacH vector of claim 1, wherein at least one of the promoters has at least 95% sequence homology with any one of SEQ ID Nos: 1 and 2 or the complementary nucleotide sequences thereof.

11. The EHV-1 RacH vector of claim 1, wherein at least one of the promoters comprises a sequence having at least 95% sequence identity with SEQ ID NO: 3 or its compliment.

12. The EHV-1 RacH vector of claim 1, wherein at least one of the promoters comprises a sequence having at least 95% sequence identity with SEQ ID NO: 4 or its compliment.

13. The EHV-1 RacH vector according to claim 1, wherein the promotors comprise p430 (SEQ ID NO: 3), and p455 (SEQ ID NO: 4).

14. The EHV-1 RacH vector of claim 1, wherein the first and the second exogenous antigen encoding sequences are hemagglutinin influenza encoding sequences.

15. The EHV-1 RacH vector of claim 1, wherein the food producing animals are swine.

16. The EHV-1 RacH vector of claim 1, wherein the pathogen infecting food producing animals is a Swine influenza A virus.

17. The EHV-1 RacH vector of claim 1, wherein the first or the second exogenous antigen encoding sequence is a hemagglutinin influenza A antigen encoding sequence having a swine origin.

18. The EHV-1 RacH vector of claim 1, wherein the first or the second exogenous antigen encoding sequence is a hemagglutinin influenza A antigen encoding sequence having a swine origin, and wherein at least one hemagglutinin influenza A antigen encoding sequence having a swine origin is inserted into ORF70.

19. The EHV-1 RacH vector of claim 1, wherein the second exogenous antigen encoding sequence is inserted into ORF1/3, wherein the first and/or the second exogenous antigen encoding sequence encodes a hemagglutinin influenza antigen having at least 95% sequence identity with any one of SEQ ID NOs:26, 27, 28, and 29, and wherein at the promoters have at least 95% sequence homology with any one of SEQ ID Nos: 1 and 2 or the complementary nucleotide sequences thereof.

20. An immunogenic composition comprising the EHV-1 RacH vector according to claim 1.

21. The immunogenic composition of claim 20, wherein the immunogenic composition is a multivalent vaccine.

22. The immunogenic composition of claim 20, wherein the immunogenic composition is a bivalent vaccine, tetravalent, hexavalent, or heptavalent vaccine.

23. A DIVA vaccine comprising the EHV-1 RacH vector according to claim 1 and a diagnostic marker for differentiating between infected and vaccinated animals.

24. The DIVA vaccine of claim 23, wherein the DIVA vaccine is a multivalent vaccine.

25. The DIVA vaccine of claim 23, wherein the DIVA vaccine is a bivalent vaccine, tetravalent, hexavalent, or heptavalent vaccine.

26. A method for immunizing a food producing animal comprising administering to the food producing animal two or more doses of the immunogenic composition according to claim 20 or the DIVA vaccine according to claim 23.

27. The method of claim 26, wherein the food producing animal is swine.

28. The method of claim 26, wherein said method results in an improvement in at least one efficacy parameter selected from: a reduction in weight loss, a lower virus load in lungs, a reduction in lung lesions, a reduced and/or shortened shedding of virus, a reduced rectal temperature, reduced respiratory symptoms, increased induction of anti-Swine Influenza A virus antibodies, increased induction of neutralizing anti-Swine Influenza A virus antibodies, increased stimulation of T-cells against Swine Influenza A virus, increased stimulation of B-cells against Swine Influenza A virus, and a reduction of pro-inflammatory cytokines, or combinations thereof, in comparison to a food producing animal of a non-immunized control group of the same species, wherein the exogenous antigen encoding sequence encodes viral antigen or a hemagglutinin influenza antigen having at least 95% sequence identity with any one of SEQ ID NOs: 26, 27, 28, and 29.

29. A method for the treatment or prophylaxis of clinical signs caused by swine influenza virus in a food producing animal, the method comprising administering to the food producing animal a therapeutically effective amount of the immunogenic composition according to claim 20 or the DIVA vaccine according to claim 23, wherein the exogenous antigen encoding sequence encodes a hemagglutinin influenza antigen having at least 95% sequence identity with any one of SEQ ID NOs: 26, 27, 28, and 29.

30. A method of reducing the virus titers in lungs in a food producing animal, in comparison to a food producing animal of a non-immunized control group of the same species, the method comprising administering to the food producing animal a therapeutically effective amount of the immunogenic composition according to claim 20 or the DIVA vaccine according to claim 23, wherein the exogenous antigen encoding sequence encodes a viral antigen having at least 95% sequence identity with any one of SEQ ID NOs: 26, 27, 28, and 29.

* * * * *